US012667357B2

(12) United States Patent (10) Patent No.: US 12,667,357 B2
Hopkins et al. (45) Date of Patent: *Jun. 30, 2026

(54) SURGICAL STAPLER WITH CIRCUMFERENTIAL FIRING

(71) Applicant: Applied Medical Resources Corporation, Rancho Santa Margarita, CA (US)

(72) Inventors: Timothy M. Hopkins, Rancho Santa Margarita, CA (US); Atal C. Patel, Mission Viejo, CA (US); Donald L. Gadberry, Capistrano Beach, CA (US); Matthew M. Becerra, Lake Forest, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/941,672

(22) Filed: Nov. 8, 2024

(65) Prior Publication Data

US 2025/0064453 A1 Feb. 27, 2025

Related U.S. Application Data

(63) Continuation of application No. 18/306,878, filed on Apr. 25, 2023, now Pat. No. 12,161,336, which is a (Continued)

(51) Int. Cl.
*A61B 17/10* (2006.01)
*A61B 17/064* (2006.01)
*A61B 17/072* (2006.01)

(52) U.S. Cl.
CPC ........ *A61B 17/105* (2013.01); *A61B 17/0644* (2013.01); *A61B 17/07207* (2013.01);
(Continued)

(58) Field of Classification Search
CPC .............. A61B 17/105; A61B 17/0644; A61B 17/07207
See application file for complete search history.

(56) References Cited

U.S. PATENT DOCUMENTS

| | | | |
|---|---|---|---|
| 2,073,960 A | | 3/1937 | Crosby |
| 2,140,593 A | | 12/1938 | Pankonin |

(Continued)

FOREIGN PATENT DOCUMENTS

| | | | |
|---|---|---|---|
| EP | 0 251 444 A1 | 1/1988 | |
| EP | 0 492 283 A1 | 7/1992 | |

(Continued)

OTHER PUBLICATIONS

European Patent Office, The International Search Report and Written Opinion for International Application No. PCT/US2015/035379, mailed Sep. 15, 2015, entitled "Surgical stapler with circumferential firing," 22 pages.

(Continued)

*Primary Examiner* — Nathaniel C Chukwurah
(74) *Attorney, Agent, or Firm* — John F. Heal

(57) ABSTRACT

A surgical stapler is provided. The stapler employs circumferential channels through which staples are deployed along an arc pathway against an anvil surface. The curved channels allow staples with relatively longer legs to be used in the stapler having a smaller diameter at the jaws. Also, by utilizing a curved path, a much larger staple can be placed in the same diameter device. Specialized curved staples for use with the stapler of the present invention are also provided. To further enable the benefits of the stapler with circumferential channels and method of staple deployment, novel jaw reinforcement structures are provided in the present invention. The jaw reinforcement structures are located towards the center or bladeline of the device instead of around the circumference as in conventional staplers, (Continued)

thereby clearing the outer area near the circumference of the device to provide room for longer staples and staple firing components.

20 Claims, 47 Drawing Sheets

Related U.S. Application Data continuation of application No. 17/241,425, filed on Apr. 27, 2021, now Pat. No. 11,666,336, which is a continuation of application No. 16/275,744, filed on Feb. 14, 2019, now Pat. No. 11,020,117, which is a continuation of application No. 14/933,892, filed on Nov. 5, 2015, now Pat. No. 10,245,038, which is a continuation of application No. PCT/US2015/035379, filed on Jun. 11, 2015.

(60) Provisional application No. 62/010,883, filed on Jun. 11, 2014.

(52) U.S. Cl.
CPC ................. *A61B 2017/0641* (2013.01); *A61B 2017/07271* (2013.01); *A61B 2017/07278* (2013.01)

(56) References Cited

U.S. PATENT DOCUMENTS

| | | | |
|---|---|---|---|
| 2,351,608 A | 6/1944 | Greenwood |
| 2,487,565 A | 11/1949 | Leber et al. |
| 2,641,154 A | 6/1953 | Heller |
| 3,076,373 A | 2/1963 | Matthews |
| 3,077,812 A | 2/1963 | Dietrich |
| 3,080,564 A | 3/1963 | Strekopitov et al. |
| 3,203,220 A | 8/1965 | Kaepernik |
| 3,252,643 A | 5/1966 | Strekopitov et al. |
| 3,273,562 A | 9/1966 | Brown |
| 3,373,646 A | 3/1968 | Ehlert |
| 3,459,187 A | 8/1969 | Pallotta |
| 3,494,533 A | 2/1970 | Green et al. |
| 3,662,939 A | 5/1972 | Bryan |
| 3,675,688 A | 7/1972 | Bryan et al. |
| 3,692,224 A | 9/1972 | Astafiev et al. |
| 4,261,244 A | 4/1981 | Becht et al. |
| 4,281,785 A | 8/1981 | Brooks |
| 4,304,236 A | 12/1981 | Conta et al. |
| 4,312,363 A | 1/1982 | Rothfuss et al. |
| 4,317,451 A | 3/1982 | Cerwin et al. |
| 4,407,286 A | 10/1983 | Noiles et al. |
| 4,434,796 A | 3/1984 | Karapetian et al. |
| 4,442,964 A | 4/1984 | Becht |
| 4,454,875 A | 6/1984 | Pratt et al. |
| 4,522,327 A | 6/1985 | Korthoff et al. |
| 4,527,724 A | 7/1985 | Chow et al. |
| 4,589,582 A | 5/1986 | Bilotti |
| 4,591,085 A | 5/1986 | Di Giovanni |
| 4,606,344 A | 8/1986 | Di Giovanni |
| 4,608,981 A | 9/1986 | Rothfuss et al. |
| 4,610,383 A | 9/1986 | Rothfuss et al. |
| 4,728,020 A | 3/1988 | Green et al. |
| 4,805,823 A | 2/1989 | Rothfuss |
| 4,892,244 A | 1/1990 | Fox et al. |
| 4,923,350 A | 5/1990 | Hinksman et al. |
| 4,941,623 A | 7/1990 | Pruitt |
| 4,955,959 A | 9/1990 | Tompkins et al. |
| 4,978,049 A | 12/1990 | Green |
| 5,031,814 A | 7/1991 | Tompkins et al. |
| 5,065,929 A | 11/1991 | Schulze et al. |
| 5,071,052 A | 12/1991 | Rodak et al. |
| 5,106,008 A | 4/1992 | Tompkins et al. |
| 5,116,349 A | 5/1992 | Aranyi |

| | | | |
|---|---|---|---|
| 5,129,570 A | 7/1992 | Schulze et al. |
| 5,180,092 A | 1/1993 | Crainich |
| 5,201,746 A | 4/1993 | Shichman |
| 5,221,036 A | 6/1993 | Takase |
| 5,236,440 A | 8/1993 | Hlavacek |
| 5,240,163 A | 8/1993 | Stein et al. |
| RE34,519 E | 1/1994 | Fox et al. |
| 5,275,323 A | 1/1994 | Schulze et al. |
| 5,289,963 A | 3/1994 | McGarry et al. |
| D347,474 S | 5/1994 | Olson |
| 5,307,976 A | 5/1994 | Olson et al. |
| 5,308,576 A | 5/1994 | Green et al. |
| 5,326,013 A | 7/1994 | Green et al. |
| 5,350,400 A | 9/1994 | Esposito et al. |
| 5,360,305 A | 11/1994 | Kerrigan |
| 5,364,002 A | 11/1994 | Green et al. |
| 5,366,479 A | 11/1994 | McGarry et al. |
| 5,381,943 A | 1/1995 | Allen et al. |
| 5,389,098 A | 2/1995 | Tsuruta et al. |
| 5,395,034 A | 3/1995 | Allen et al. |
| 5,397,046 A | 3/1995 | Savage et al. |
| 5,413,267 A | 5/1995 | Solyntjes et al. |
| 5,415,334 A | 5/1995 | Williamson, IV et al. |
| 5,415,335 A | 5/1995 | Knodell, Jr. |
| 5,439,155 A | 8/1995 | Viola |
| 5,439,479 A | 8/1995 | Shichman et al. |
| 5,445,304 A | 8/1995 | Plyley et al. |
| 5,447,265 A | 9/1995 | Vidal et al. |
| 5,452,836 A | 9/1995 | Huitema et al. |
| 5,456,401 A | 10/1995 | Green et al. |
| 5,458,279 A | 10/1995 | Plyley |
| 5,462,215 A | 10/1995 | Viola et al. |
| 5,464,144 A | 11/1995 | Guy et al. |
| 5,465,895 A | 11/1995 | Knodel et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,480,089 A | 1/1996 | Blewett |
| 5,485,952 A | 1/1996 | Fontayne |
| 5,487,500 A | 1/1996 | Knodel et al. |
| 5,489,058 A | 2/1996 | Plyley |
| 5,497,933 A | 3/1996 | DeFonzo et al. |
| 5,507,426 A | 4/1996 | Young et al. |
| 5,507,773 A | 4/1996 | Huitema et al. |
| 5,509,596 A | 4/1996 | Green et al. |
| 5,509,920 A | 4/1996 | Phillips et al. |
| 5,529,235 A | 6/1996 | Boiarski et al. |
| 5,547,117 A | 8/1996 | Hamblin et al. |
| 5,553,765 A | 9/1996 | Knodel et al. |
| 5,554,164 A | 9/1996 | Wilson et al. |
| 5,558,266 A | 9/1996 | Green et al. |
| 5,562,241 A | 10/1996 | Knodel et al. |
| 5,562,700 A | 10/1996 | Huitema et al. |
| 5,562,701 A | 10/1996 | Huitema et al. |
| 5,562,702 A | 10/1996 | Huitema et al. |
| 5,564,615 A | 10/1996 | Bishop et al. |
| 5,571,115 A | 11/1996 | Nicholas |
| 5,571,285 A | 11/1996 | Chow et al. |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,581 A | 12/1996 | Conlon et al. |
| 5,597,107 A | 1/1997 | Knodel et al. |
| 5,601,224 A | 2/1997 | Bishop et al. |
| 5,605,272 A | 2/1997 | Witt et al. |
| 5,607,095 A | 3/1997 | Smith et al. |
| 5,615,820 A | 4/1997 | Viola |
| 5,626,587 A | 5/1997 | Bishop et al. |
| 5,630,539 A | 5/1997 | Plyley et al. |
| 5,634,584 A | 6/1997 | Okorocha et al. |
| 5,636,779 A | 6/1997 | Palmer |
| 5,657,921 A | 8/1997 | Young et al. |
| 5,662,258 A | 9/1997 | Knodel et al. |
| 5,662,662 A | 9/1997 | Bishop et al. |
| 5,662,667 A | 9/1997 | Knodel |
| 5,673,840 A | 10/1997 | Schulze et al. |

(56) References Cited

U.S. PATENT DOCUMENTS

| | | | |
|---|---|---|---|
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley |
| 5,680,982 A | 10/1997 | Schulze et al. |
| 5,680,983 A | 10/1997 | Plyley et al. |
| 5,697,542 A | 12/1997 | Knodel et al. |
| 5,697,543 A | 12/1997 | Burdorff |
| 5,704,534 A | 1/1998 | Huitema et al. |
| 5,704,898 A | 1/1998 | Kokish |
| 5,706,998 A | 1/1998 | Blyley et al. |
| 5,709,334 A | 1/1998 | Sorrentino et al. |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,810,240 A | 9/1998 | Robertson |
| 5,814,055 A | 9/1998 | Knodel et al. |
| 5,820,009 A | 10/1998 | Melling et al. |
| 5,829,662 A | 11/1998 | Allen et al. |
| 5,860,995 A | 1/1999 | Berkelaar |
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentino et al. |
| 5,931,847 A | 8/1999 | Bittner et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A | 3/2000 | Mastri et al. |
| 6,053,390 A | 4/2000 | Green et al. |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 | 5/2006 | Mastri et al. |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B2 | 6/2009 | Green et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 | 11/2009 | Viola |
| 7,624,902 B2 | 12/2009 | Marczyk et al. |

(56)  References Cited

U.S. PATENT DOCUMENTS

| | | | |
|---|---|---|---|
| 7,631,793 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |

(56)                References Cited

U.S. PATENT DOCUMENTS

| | | | |
|---|---|---|---|
| 8,292,151 B2 | 10/2012 | Viola |
| 8,292,152 B2 | 10/2012 | Milliman et al. |
| 8,292,153 B2 | 10/2012 | Jankowski |
| 8,292,157 B2 | 10/2012 | Smith et al. |
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,972 B2 | 3/2013 | Kostrzewski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,386,984 B2 | 7/2016 | Aronhalt et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |

(56) References Cited

U.S. PATENT DOCUMENTS

| | | | |
|---|---|---|---|
| 10,245,038 B2 * | 4/2019 | Hopkins ......... A61B 17/07207 |
| 11,020,117 B2 * | 6/2021 | Hopkins ......... A61B 17/07207 |
| 2002/0025243 A1 | 2/2002 | Heck |
| 2002/0029044 A1 | 3/2002 | Monassevitch et al. |
| 2002/0062136 A1 | 5/2002 | Hillstead |
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2004/0138705 A1 | 7/2004 | Heino et al. |
| 2005/0234478 A1 | 10/2005 | Wixey |
| 2006/0097026 A1 | 5/2006 | Shelton, IV |
| 2006/0100644 A1 | 5/2006 | Viola |
| 2006/0180634 A1 | 8/2006 | Shelton, IV et al. |
| 2006/0235442 A1 | 10/2006 | Huitema |
| 2006/0289602 A1 | 12/2006 | Wales et al. |
| 2007/0034664 A1 | 2/2007 | Jiang |
| 2007/0039997 A1 | 2/2007 | Mather et al. |
| 2007/0057014 A1 | 3/2007 | Whitman et al. |
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |
| 2008/0029575 A1 | 2/2008 | Shelton et al. |
| 2008/0041918 A1 | 2/2008 | Holsten et al. |
| 2008/0078807 A1 | 4/2008 | Hess et al. |
| 2008/0083807 A1 | 4/2008 | Beardsley et al. |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0143806 A1 | 6/2009 | Witt et al. |
| 2009/0198272 A1 | 8/2009 | Kerver et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139852 A1 | 6/2011 | Zingman |
| 2011/0147433 A1 | 6/2011 | Shelton, IV et al. |
| 2011/0155784 A1 | 6/2011 | Shelton, IV et al. |
| 2011/0155787 A1 | 6/2011 | Baxter, III et al. |
| 2011/0290851 A1 | 12/2011 | Shelton, IV et al. |
| 2011/0290853 A1 | 12/2011 | Shelton, IV et al. |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0109186 A1 | 5/2012 | Parrott et al. |
| 2012/0168487 A1 | 7/2012 | Holsten et al. |
| 2012/0193396 A1 | 8/2012 | Zemlok et al. |
| 2012/0203247 A1 | 8/2012 | Shelton, IV et al. |
| 2012/0211542 A1 | 8/2012 | Racenet |
| 2012/0239009 A1 | 9/2012 | Mollere et al. |
| 2012/0253298 A1 | 10/2012 | Henderson et al. |
| 2012/0286022 A1 | 11/2012 | Olson et al. |
| 2012/0318844 A1 | 12/2012 | Shelton, IV et al. |
| 2012/0325893 A1 | 12/2012 | Pastorelli et al. |
| 2013/0001270 A1 | 1/2013 | Kostrzewski |
| 2013/0012958 A1 | 1/2013 | Marczyk et al. |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0327809 A1 | 12/2013 | Shelton, IV et al. |
| 2013/0327810 A1 | 12/2013 | Swayze et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0103092 A1 | 4/2014 | Kostrzewski et al. |
| 2014/0103093 A1 | 4/2014 | Koch, Jr. et al. |

(56) References Cited

U.S. PATENT DOCUMENTS

| | | |
|---|---|---|
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |
| 2014/0203063 A1 | 7/2014 | Hessler et al. |
| 2014/0205637 A1 | 7/2014 | Widenhouse et al. |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1 | 9/2014 | Aranyi et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1 | 10/2014 | Shelton, IV et al. |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0289873 A1 | 10/2015 | Shelton, IV et al. |
| 2015/0297221 A1 | 10/2015 | Kerr et al. |
| 2015/0297233 A1 | 10/2015 | Huitema et al. |
| 2015/0380187 A1 | 12/2015 | Zergiebel et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0183948 A1 | 6/2016 | Shelton, IV et al. |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0231633 A1 | 8/2017 | Marczyk et al. |
| 2017/0245856 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1 | 10/2017 | Reed et al. |
| 2017/0290584 A1 | 10/2017 | Jasemian et al. |
| 2019/0261984 A1 | 8/2019 | Nelson et al. |
| 2020/0268381 A1 | 8/2020 | Roberts et al. |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 044 893 A2 | 9/2008 |
| EP | 2 005 902 A2 | 12/2008 |
| EP | 2 090 241 A1 | 8/2009 |
| EP | 2 263 568 A2 | 12/2010 |
| EP | 2 361 562 A1 | 8/2011 |
| EP | 2 462 875 A2 | 6/2012 |
| EP | 2 486 859 A2 | 8/2012 |
| EP | 2 764 833 A2 | 8/2014 |
| EP | 2 772 192 A1 | 9/2014 |
| EP | 2 777 530 A1 | 9/2014 |
| EP | 2 815 705 A1 | 12/2014 |
| EP | 2 923 661 A2 | 3/2015 |
| EP | 2 853 204 A1 | 4/2015 |
| EP | 2 891 462 A1 | 7/2015 |
| EP | 2 926 742 A1 | 10/2015 |
| EP | 2 942 020 A2 | 11/2015 |
| EP | 2 959 841 A1 | 12/2015 |
| EP | 2 959 851 A1 | 12/2015 |
| EP | 3 135 225 A2 | 3/2017 |
| EP | 3 238 639 A2 | 3/2017 |
| EP | 3 338 653 A1 | 6/2018 |
| EP | 3 338 698 A1 | 6/2018 |
| EP | 3 338 702 A1 | 6/2018 |
| JP | 2001-087272 A | 4/2001 |
| RU | 2063710 | 7/1996 |

(56) References Cited

FOREIGN PATENT DOCUMENTS

| WO | WO 83/02247 A1 | 7/1983 |
| WO | WO 94/24947 A1 | 11/1994 |
| WO | WO 02/30296 A2 | 4/2002 |
| WO | WO 02/096327 A2 | 12/2002 |
| WO | WO 2003/094747 A1 | 11/2003 |
| WO | WO 2004/032762 A1 | 4/2004 |
| WO | WO 2012/052729 A1 | 4/2012 |
| WO | WO 2014/139440 A1 | 9/2014 |
| WO | WO 2020/077531 A1 | 4/2020 |

OTHER PUBLICATIONS

The International Bureau of WIPO, International Preliminary Report on Patentabilityfor International Application No. PCT/US2015/035379, entitled "Surgical Stapler with Circumferential Firing," dated Dec. 22, 2016, 14 pgs.

European Patent Office, European Search Report for European Application No. 07784007.2, entitled "Surgical Stapler," dated Jun. 15, 2012, 6 pgs.

Ethicon Endo Surgery, Inc., Contour Curved Cutter Stapler, 2014, 2 pgs.

Justright Surgical, JustRight Surgery, Dec. 31, 2014, 2 pgs.

European Patent Office, The International Search Report and the Written Opinion of the International Searching Authority for International Application No. PCT/US2014/028811, entitled "Surgical Stapler Having Actuation Mechanism with Rotatable Shaft," mailed Aug. 5, 2014, 14 pgs.

European Patent Office, International Search Report and Written Opinion for International Application No. PCT/US2014/028211, entitled "Surgical Stapler with Partial Pockets," mailed Sep. 8, 2014, 17 pgs.

International Searching Authority, U.S., The International Search Report and the Written Opinion of the International Searching authority for international application PCT/US2014/027768, titled "Surgical Stapler with Expandable Jaw", mailed Jul. 25, 2014, 17 pgs.

The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.

The International Bureau of WIPO, International Preliminary Report on Patentability, for International Application No. PCT/US2014/027768, entitled "Surgical Stapler with Expandable Jaw," dated Sep. 24, 2015, 9 pgs.

European Patent Office, International Search Report and Written Opinion for International Application No. PCT/US2015/050103 titled "Surgical Stapler with Self-Adjusting Staple Height" dated Feb. 17, 2016, 18 pgs.

The International Bureau of WIPO, International Preliminary Report on Patentability for International Application No. PCT/US2015/050103, titled "Surgical Stapler With Self-Adjusting Staple Height," dated Mar. 30, 2017, 12 pgs.

European Patent Office, European Search Report for European Application No. EP 14764812.5, entitled "Surgical Stapler Having Actuation Mechanism with Rotatable Shaft," dated Apr. 6, 2017, 6 pgs.

International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.

International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.

International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.

European Patent Office, The International Search Report and the Written Opinion ofthe International Searching Authority for International Application No. PCT/US2017/027269, entitled "Reload Shaft Assembly for Surgical Stapler," mailed Sep. 12, 2017, 22 pgs.

European Patent Office, The International Search Report and the Written Opinion of the International Searching Authority for International Application No. PCT/US2017/027213, entitled "Surgical Stapler Having a Powered Handle," mailed Sep. 13, 2017, 17 pgs.

European Patent Office, The International Search Report and the Written Opinion of the International Searching Authority for International Application No. PCT/US2017/027142, entitled "Surgical Stapler Having Articulation Mechanism," mailed Sep. 14, 2017, 21 pgs.

European Patent Office, The International Search Report and Written Opinion of the International Searching Authority for International Application No. PCT/US2016/045993 titled "Surgical Stapler Having Locking Articulation Joint", mailed Jan. 24, 2017, 20 pgs.

European Patent Office, Partial European Search Report for European Application No. EP 14762896.0, entitled "Surgical Stapler with Expandable Jaw," dated Apr. 10, 2017, 6 pgs.

The International Bureau of WIPO, International Preliminary Report on Patentability, for International Application No. PCT/US2016/045993, entitled "Surgical Stapler Having Locking Articulation Joint," dated Feb. 15, 2018, 13 pgs.

European Patent Office, Extended European Search Report for European Application No. EP 18186558.5, entitled "Surgical Stapler with Partial Pockets," dated Oct. 10, 2018, 9 pgs.

The International Bureau of WIPO, International Preliminary Report on Patentability, for International Application No. PCT/US2017/027142, entitled "Surgical Stapler Having Articulation Mechanism," dated Oct. 25, 2018, 12 pgs.

The International Bureau of WIPO, International Preliminary Report on Patentability, for International Application No. PCT/US2017/027213, entitled "Surgical Stapler Having Powered Handle," dated Oct. 25, 2018, 9 pgs.

The International Bureau of WIPO, International Preliminary Report on Patentability, for International Application No. PCT/US2017/027269, entitled "Reload Shaft Assembly for Surgical Stapler," dated Oct. 25, 2018, 12 pgs.

European Patent Office, Extended European Search Report for European ApplicationNo. EP 18189960.0, entitled "Surgical Stapler with Expandable Jaw," dated Dec. 13, 2018, 6 pgs.

International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.

European Patent Office, The International Search Report and the Written Opinion of the International Searching Authority for International Application No. PCT/US2019/019867, entitled "Surgical Stapler Having a Powered Handle," mailed Jul. 19, 2019, 24 pgs.

European Patent Office, Extended European Search Report for European Application No. EP 19150575.9, entitled "Surgical Stapler Having Actuation Mechanism with Rotatable Shaft," dated Aug. 21, 2019, 5 pgs.

European Patent Office, Extended European Search Report for European Application No. EP 19180055.6, entitled "Surgical Stapler with Circumferential Firing," dated Sep. 20, 2019, 8 pgs.

European Patent Office, The International Search Report and the Written Opinion of the International Searching Authority for International Application No. PCT/US2020/019938, entitled "Surgical Stapling Instrument Having a Two-Position Mechanism," mailed Jun. 18, 2020, 16 pgs.

European Patent Office, Extended European Search Report for European Application No. EP 20157713.7, entitled "Surgical Stapler with Expandable Jaw," dated May 11, 2020, 6 pgs.

International Searching Authority/ EPO, Invitation to Pay Additional Fees for PCTUS2020/025496, entitled "Reload Cover for Surgical Stapling System," dated Jun. 18, 2019, 15 pgs.

European Patent Office, Extended European Search Report for European Application No. EP 20161294.2, entitled "Surgical Stapler with Self-Adjusting Staple Height," dated Jun. 22, 2020, 6 pgs.

European Patent Office, The International Search Report and the Written Opinion of the International Searching Authority for Inter-

(56)                    References Cited

OTHER PUBLICATIONS national Application No. PCT/US2020/025496, entitled "Reload Cover for Surgical Stapling System," mailed Aug. 13, 2020, 20 pgs.
The International Bureau of WIPO, International Preliminary Report on Patentability, for International Application No. PCT/US2019/019867, entitled "Surgical Stapler Having a Powered Handle," dated Sep. 3, 2020, 16 pgs.
European Patent Office, Extended European Search Report for European Application No. EP 20197859.0, entitled "Surgical Stapler with Circumferential Firing," dated Jan. 28, 2021, 13 pgs.
European Patent Office, Extended European Search Report for European Application No. EP 21162419.2, entitled "Surgical Stapler Having Articulation Mechanism," dated Jun. 22, 2021, 10 pgs.
The International Bureau of WIPO, International Preliminary Report on Patentability, for International Application No. PCT/US2020/019938, entitled "Surgical Stapler Having a Two-Position Lockout Mechanism," dated Sep. 10, 2020, 10 pgs.
The International Bureau of WIPO, International Preliminary Report on Patentability, for International Application No. PCT/US2020/025496 entitled "Reload Cover for Surgical System," dated Oct. 14, 2021, 12 pgs.
European Patent Office, Extended European Search Report for European Application No. EP 21173771.3, entitled "Reload Shaft Assembly for Surgical Stapler," dated Aug. 27, 2021, 10 pgs.
European Patent Office, Extended European Search Report for European Application No. EP 21195788.1, entitled "Surgical Stapler with Self-Adjusting Staple Height," dated Dec. 13, 2021, 9 pgs.
International Searching Authority/ EPO, Invitation to Pay Additional Fees and Communication Relating to the Results of the Partial International Search for PCT/US2021/057365, entitled "Surgical Stapler Having a Powered Handle," dated Feb. 23, 2022, 14 pgs.
European Patent Office, The International Search Report and the Written Opinion of the International Searching Authority for International Application No. PCT/US2021/057278, entitled "Actuation Shaft Retention Mechanism for Surgical Stapler" mailed Feb. 23, 2022, 15 pgs.
European Patent Office, The International Search Report and the Written Opinion of the International Searching Authority for International Application No. PCT/US2021/057231, entitled "Material Combinations and Processing Methods for a Surgical Instrument" mailed Feb. 11, 2022, 15 pgs.
European Patent Office, The International Search Report and the Written Opinion of the International Searching Authority for International Application No. PCT/US2021/057365, entitled "Surgical Stapler Having a Powered Handle" mailed Apr. 13, 2022, 21 pgs.
European Patent Office, The International Search Report and the Written Opinion of the International Searching Authority for International Application No. PCT/US2022/012452, entitled "Surgical Stapler Having Shaft Recognition Mechanism" mailed Apr. 13, 2022, 13 pgs.
European Patent Office, Extended European Search Report for European Application No. EP 22196603.9, entitled "Surgical Stapler with Expandable Jaw," dated Dec. 14, 2022, 6 pgs.
European Patent Office, Extended European Search Report for European Application No. EP 22203599.0, entitled "Surgical Stapler Having a Powered Handle," dated Feb. 7, 2023, 7 pgs.
European Patent Office, Extended European Search Report for European Application No. EP 22203464.7, entitled "Surgical Stapler with Partial Pockets," dated Dec. 20, 2022, 9 pgs.
The International Bureau of WIPO, International Preliminary Report on Patentability, for International Application No. PCT/US2021/057231, entitled "Material Combinations and Processing Methods for a Surgical Instrument," dated May 11, 2023, 10 pgs.
The International Bureau of WIPO, International Preliminary Report on Patentability, for International Application No. PCT/US2021/057278, entitled "Actuation Shaft Retention Mechanism for Surgical Stapler," dated May 11, 2023, 10 pgs.
The International Bureau of WIPO, International Preliminary Report on Patentability, for International Application No. PCT/US2021/057365, entitled "Surgical Stapler Having a Powered Handle," dated May 11, 2023, 14 pgs.
The International Bureau of WIPO, International Preliminary Report on Patentability, for International Application No. PCT/US2022/012452, entitled "Surgical Stapler Having Shaft Recognition Mechanism," dated Jul. 27, 2023, 8 pgs.
European Patent Office, Extended European Search Report for European Application No. EP 23185918.2, entitled "Surgical Stapler Having Actuation Mechanism with Rotatable Shaft," dated Sep. 22, 2023, 5 pgs.
European Patent Office, Extended European Search Report for European Application No. EP 23198045.9, entitled "Reload Shaft Assembly for Surgical Stapler," dated Oct. 25, 2023, 12 pgs.
European Patent Office, Partial Extended European Search Report for European Patent Application No. 23198488.1, titled "Surgical Stapler with Self-Adjusting Staple Height," dated Jan. 23, 2024, 8 pgs.

* cited by examiner

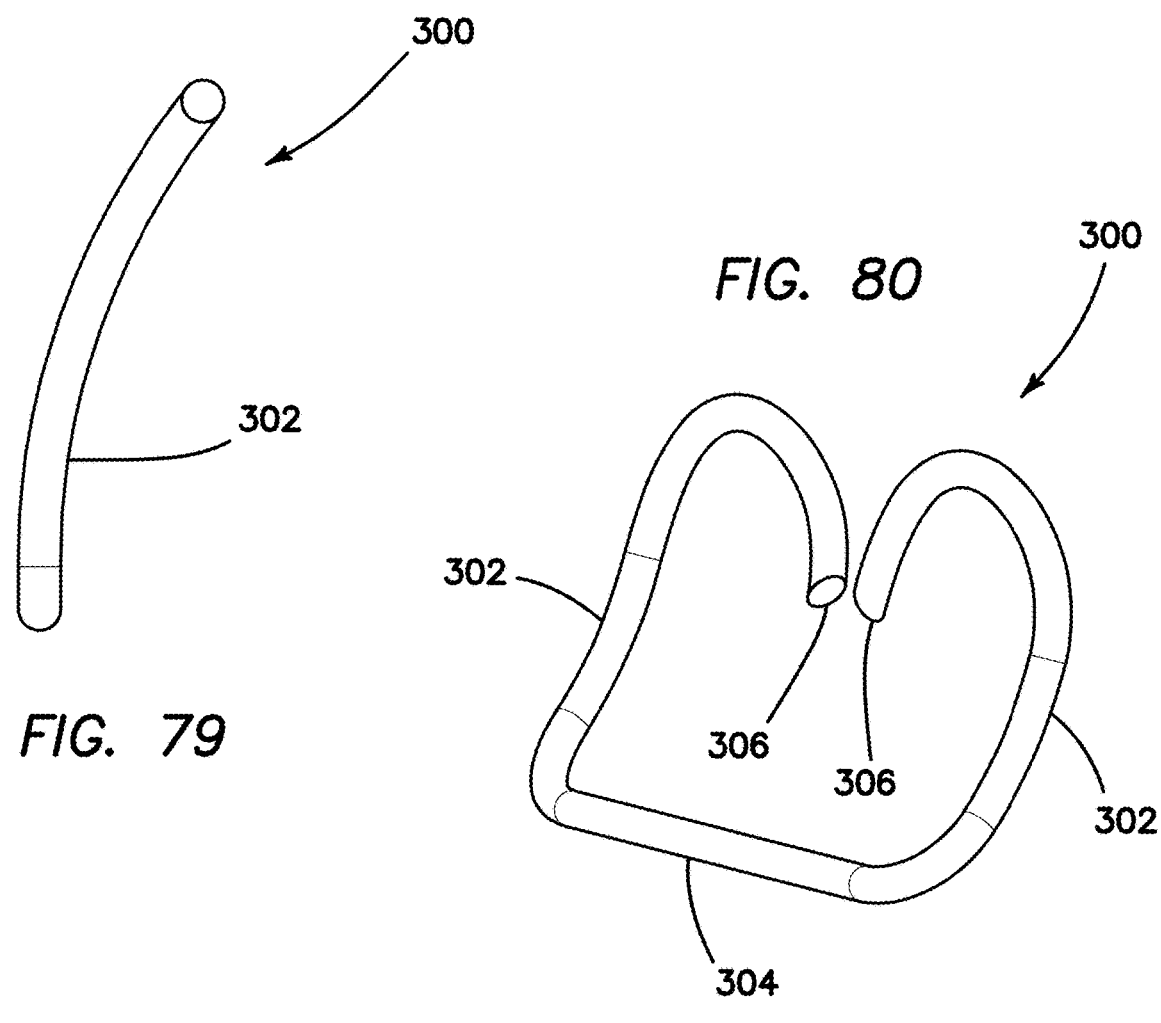
FIG. 79
FIG. 80
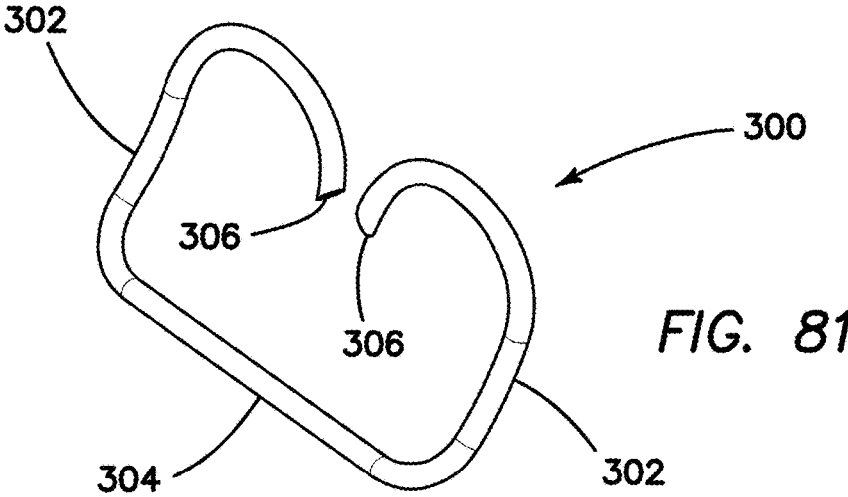
FIG. 81

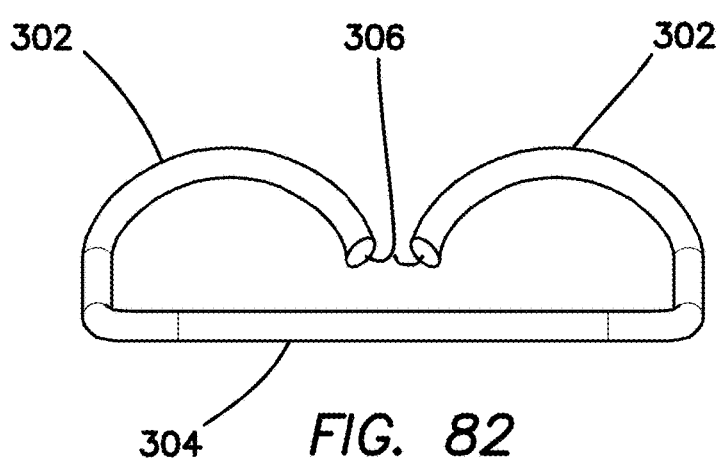
*FIG. 82*
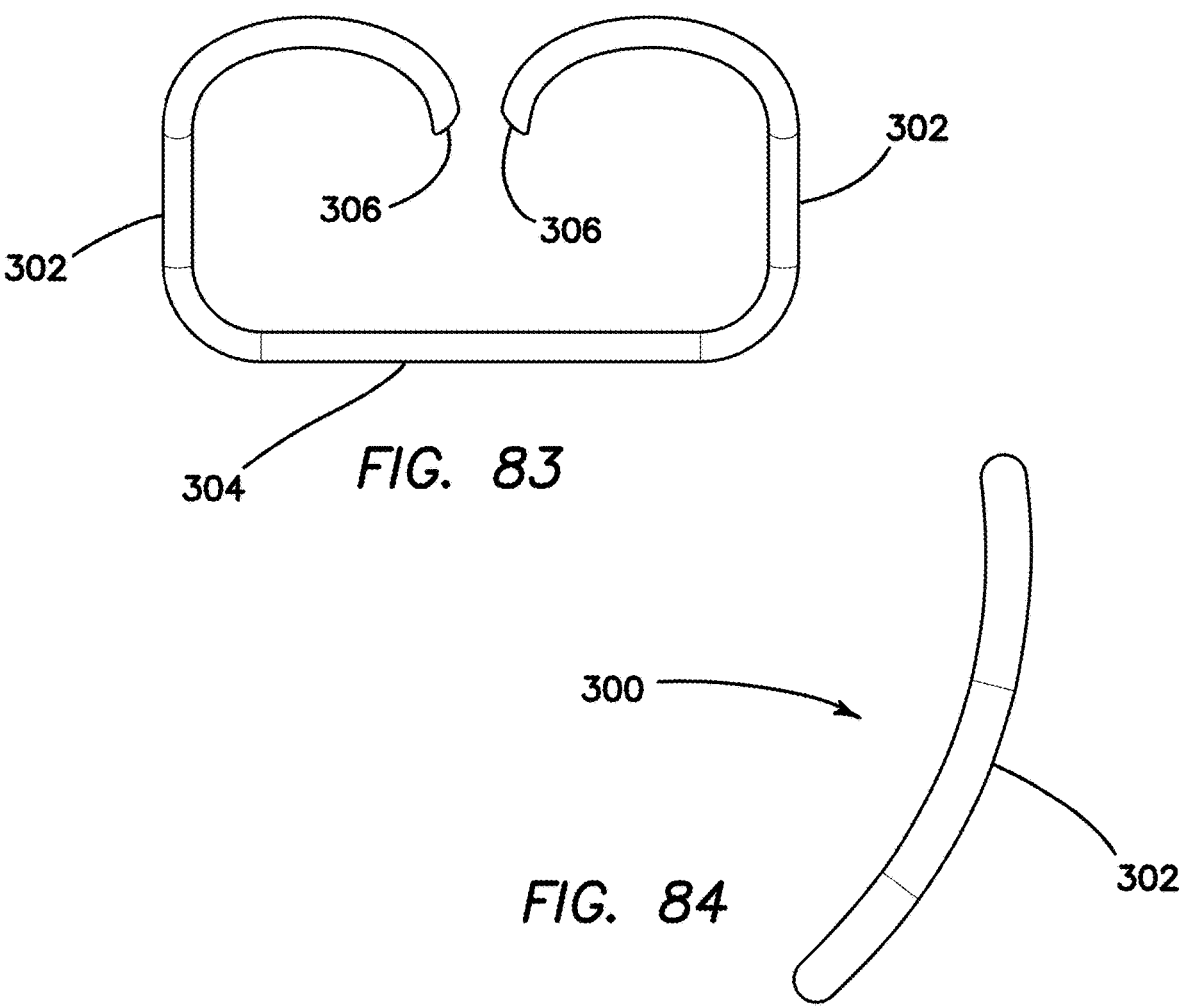
*FIG. 83*
*FIG. 84*

SURGICAL STAPLER WITH CIRCUMFERENTIAL FIRING

CROSS-REFERENCE TO RELATED APPLICATION

This application is a continuation of U.S. patent application Ser. No. 18/306,878 entitled "Surgical stapler with circumferential firing," filed Apr. 25, 2023, which is a continuation of U.S. patent application Ser. No. 17/241,425 entitled "Surgical stapler with circumferential firing," filed Apr. 27, 2021, which issued as U.S. Pat. No. 11,666,336, which is a continuation of U.S. patent application Ser. No. 16/275,744 entitled "Surgical stapler with circumferential firing," filed Feb. 14, 2019, which issued as U.S. Pat. No. 11,020,117, which is a continuation of U.S. patent application Ser. No. 14/933,892 entitled "Surgical stapler with circumferential firing," filed Nov. 5, 2015, which issued as U.S. Pat. No. 10,245,038, and which is hereby incorporated herein by reference in its entirety, which is a continuation of International Application No. PCT/US2015/035379 entitled "Surgical stapler with circumferential firing" filed on Jun. 11, 2015 and hereby incorporated herein by reference in its entirety, which claims priority to and benefit of U.S. Provisional Patent Application Ser. No. 62/010,883 entitled "Surgical stapler with circumferential firing" filed on Jun. 11, 2014 which is hereby incorporated herein by reference in its entirety.

FIELD OF THE INVENTION

This disclosure relates to surgical instruments, and more particularly, to surgical stapling instruments for applying a plurality of surgical staples to body tissue.

BACKGROUND OF THE INVENTION

A typical surgical stapler apparatus comprises a handle at a proximal end and two elongated jaw-like members at the distal end, joined together at a hinge. The jaw-like members articulate to open and close to capture tissue between the jaw-like members. The user controls the device from the handle to open and close the jaw-like members, actuate deployment of staples and in general manipulate and control the device. One of the jaw members carries a cartridge containing staples arranged in one or more rows. The other one of the jaw-like members comprises an anvil surface against which the staples are driven to deform the staple legs. Staples are driven out of the cartridge by a caming surface or slider that moves longitudinally against a plurality of laterally positioned pushers that push each staple out of the cartridge. The caming surface of the slider is angled to compliment the angular surface of the pushers. Some staplers include a blade that follows the caming surface so as to cut the tissue between the two or more rows of delivered staples.

Surgical staplers are used in a variety of surgical techniques including laparoscopic and/or endoscopic or other minimally invasive surgical procedures in which the stapler is inserted through a cannula or tube positioned within a small incision in a patient's body. In laparoscopic minimally invasive surgery, a trocar is inserted across body tissue of a patient to access a body cavity and to create a channel for the insertion of a camera, such as a laparoscope. The camera provides a live video feed capturing images that are then displayed to the surgeon on one or more video monitors. Additional trocars are inserted to create additional pathways through which surgical instruments, including surgical staplers, can be inserted for performing procedures observed on the video monitor. The targeted tissue location such as the abdomen is typically enlarged by delivering carbon dioxide gas to insufflate the body cavity and create a working space large enough to accommodate the scope and instruments used by the surgeon. The insufflation pressure in the tissue cavity is maintained by using specialized trocars having seals that prevent the insufflation gas from escaping and collapsing the surgical working space. Laparoscopic surgery offers a number of advantages when compared with an open procedure. These advantages include reduced pain and blood loss and shorter recovery times.

As laparoscopic surgery evolves to become even more minimally invasive with incisions and trocar/cannula diameters becoming smaller and smaller, surgical staplers for use in laparoscopic, minimally invasive procedures must be designed to fit within the small lumen of a cannula. Generally, a surgical stapler is inserted into a cannula with the jaw-like members in a closed orientation until the device jaws are inside the patient where the jaw-like members are opened to grasp and staple tissue. The handle of the stapler resides outside of the patient in control of the surgeon user. A portion of the shaft of the stapler between the jaw-like members and the handle is long enough to extend from outside the patient to inside the patient. During the stapling procedure, the elongate shaft of the stapler resides inside the cannula into which it was inserted.

The distal jaw-like members include many components such as an anvil for forming staples, a staple cartridge with a plurality of staples, a caming surface, a slider, pushers, a blade and other components which must all be small enough to fit through a small diameter cannula and made to function reliably and repeatedly from outside the patient. As shown in FIG. 1A, when closed, the distal jaw-like members of the surgical stapler 2a have a substantially circular cross-section wherein approximately one half of the cross-section comprises the lower jaw 3a that houses the staples 7a. Approximately a little less than the other half of the cross-section comprises the upper jaw 4a that houses the anvil. The circular cross-section of the distal jaw includes a gap 5a between the upper and lower jaws for receiving tissue to be stapled. In FIG. 1A, a vertical line 6a divides the cross-section in half and represents a blade line or an I-beam that carries a blade to cut tissue between one or more rows of staples 7a. The I-beam slides longitudinally along the length of the distal end and also functions to push the staples 7a out of the lower jaw 3a, across the gap 5a and against the anvil of the upper jaw 4a. A plurality of vertical lines 7a in FIG. 1A represent three rows of vertically arranged staples 7a residing in the lower jaw 3a on either side of the blade line 6a. The conventional stapler design involves ejecting the staples perpendicularly against the anvil surface.

While conventional laparoscopic staplers are approximately 12 millimeters in diameter, it is desirable to reduce the stapler diameter to fit inside a cannula having a diameter as small as approximately 5-10 mm to provide the patient with a smaller incision, reduced recovery time and reduced scarring. FIG. 1B illustrates a reduced-diameter stapler with the same conventional design as shown in FIG. 1A. As can be seen in FIG. 1B, the smaller stapler 2b has a smaller diameter with less space for a lower jaw 3b and upper jaw 4b. The tissue gap 5b is approximately the same as the tissue gap 5b of the larger stapler 2a for stapling tissue having approximately the same thickness. As a result of the reduced diameter and conventional design that ejects staples perpendicularly against the anvil surface, the smaller stapler 2b accommodates staples 7b in the lower jaw 3b that have shorter staple legs as shown in FIG. 1B. The length SB of the staple legs in the smaller variation of FIG. 1B is significantly shorter than the length SA of the staple legs in the larger variation of FIG. 1A. This is an inherent limitation of staple leg length in smaller diameter staplers employing the same conventional design. Hence, it is desirable to have a smaller diameter stapler that is capable of being inserted into smaller cannulas while at the same time still retaining the same ability to fire larger staples.

FIG. 2A illustrates tissue 8a that has been cut along a blade line 6a and stapled with the conventional stapler 2a of FIG. 1A. FIG. 2A shows three rows of staples 7a delivered into tissue 8a adjacent to a blade line 6a. The other three rows of staples 7a on the opposite side of the blade line 6a are delivered into a tissue segment that is not shown in FIG. 2A. The distance CA is the length of tissue 8a that has been stapled. FIG. 2B illustrates tissue 8b that has been cut along a blade line 6b and stapled with the conventional stapler 2b of FIG. 1B having a smaller diameter relative to the stapler of FIG. 1A. FIG. 2B also shows three rows of staples 7b delivered into tissue 8b adjacent to the blade line 6b. The distance CB is the length of tissue 8b that has been stapled. When compared with the length CA of FIG. 2A, the smaller diameter stapler 2b produces a shorter length CB. The length CB is naturally shorter as staples 7b are more closely placed in the reduced lower jaw 3b area.

Also, the cuff length, which is the distance between the blade line or cut edge and the closest staple row to the cut edge or blade line, may be shorter as longer staples are placed closer to the diameter as shown in FIG. 2B when compared to FIG. 2A. In order to fit multiple rows of staples 7b in a smaller diameter version stapler 2b, the stapler 2b is configured to deliver a row of staples 7b as close as possible to the blade line 6b as shown in FIG. 2B. The proximity of this line of delivered staples 7b is much closer to the blade line 6b than the same line of staples 7a in the larger version stapler 2a. Proximity of staples to the blade line 6b may increase the chances of a misfired staple crossing the blade line. Also, proximity of the staples to the blade line results in the first line of staples 7b being very close to the edge of the tissue 8b which may reduce tissue holding. Hence, it is desirable to provide a smaller stapler that reduces the risk of staple jamming and that provides more tissue between the staple line and the edge of tissue.

In order to accomplish the above-mentioned objectives, a smaller diameter stapler utilizing a conventional design may require that the design includes shorter staples or other design compromises. Hence, it is desirable to have a smaller stapler without sacrificing the above-mentioned objectives while at the same time retaining the same functionality and efficacy in a design with smaller diameter.

Also, many other factors enter the equation for an improved stapler. These factors include but are not limited to reducing the force required to deliver staples. Reducing the actuation force improves the accuracy for the surgeon requiring finesse in a surgical procedure and also reduces surgeon fatigue. Typically, when staples are fired perpendicularly against an anvil surface, the staple legs are forced to buckle. Another factor that creates a better stapler is the strength of the deformed staple. For instance, the deformed staple must have a shape that includes a space for receiving tissue without unduly compressing or severing the tissue in the location of the staple. Also, the deformed shape of the staple must be strong enough to withstand forces that would tend to pull the staple open. Overall, it is an object of the present invention to provide an improved stapler that retains the functionality and efficacy in a reduced-diameter stapler and resulting staple line taking into consideration the above-mentioned as well as other design factors. Conversely, it is an object of the present invention to provide a stapler having the same diameter as a conventional surgical stapler that can fire longer staples with circumferential firing than previously possible without circumferential firing.

SUMMARY OF THE INVENTION

A surgical stapler is provided. The stapler employs circumferential channels through which staples are deployed along an arc pathway against an anvil surface. The curved channels allow staples with relatively longer legs to be used in the stapler of the present invention having a smaller diameter at the jaws. Also, by utilizing a curved path, a much larger staple can be placed in the same diameter device. In certain embodiments, a staple up to three times larger can be employed in a stapler of the present invention. Specialized curved staples for use with the stapler of the present invention are also provided. To further enable the benefits of the stapler with circumferential staple channels and method of staple deployment, novel jaw reinforcement structures are also provided in the present invention. The stapler jaw reinforcement structures are located towards the center or bladeline of the device instead of around the circumference as in conventional staplers, thereby clearing the outer area near the circumference of the device to provide room for longer staples and staple firing components.

According to another aspect of the invention, a surgical stapler is provided. The surgical stapler includes a handle assembly connected to a stapler cartridge assembly. The stapler cartridge assembly has an end effector at the distal end. The end effector includes an upper jaw connected to a lower jaw such that the upper jaw is movable via the handle assembly relative to the lower jaw between an open configuration and a closed configuration. The lower jaw has an upper surface and the upper jaw has an anvil surface. In the closed configuration, a gap is defined between the upper surface and anvil surface for receiving tissue to be stapled. The lower jaw further includes a plurality of staple channels arranged longitudinally along the length of the lower jaw and configured to receive staples. Each staple channel has an opening at the upper surface. A center point is defined by a cross-section taken perpendicular to the longitudinal axis of the end effector with the jaws in a closed configuration wherein one or more staple channels are curved about the center point. In another variation, the staple channels are concentric about the center point. In another variation, one or more staple channels are elliptical about the center point. In another variation, the stapler further includes a plurality of staples disposed inside the staple channels and each staple has curved legs that conform to the curvature of the staple channels in which they reside. In another variation, the stapler further includes a plurality of pushers disposed inside the staple channels that are configured to contact and eject staples and each pusher has concentric side surfaces that conform to the curvature of the staple channel in which it resides.

According to another aspect of the invention, a surgical stapler is provided. The surgical stapler includes a handle assembly connected to a stapler cartridge assembly. The stapler cartridge assembly has an end effector at the distal end. The end effector includes an upper jaw connected to a lower jaw such that the upper jaw is movable via the handle assembly relative to the lower jaw between an open configuration and a closed configuration. Of course, either of the upper jaw and the lower jaw can be movable with respect to the other and in another variation, both jaws are movable. The lower jaw has an upper surface and the upper jaw has an anvil surface. In the closed configuration, a gap is defined between the upper surface and anvil surface for receiving tissue to be stapled. The lower jaw further includes a plurality of staple channels arranged longitudinally along the length of the lower jaw and configured to receive staples. Each staple channel has an opening at the upper surface. A center point and midline are defined by a cross-section taken perpendicular to the longitudinal axis of the end effector with the jaws in a closed configuration. More than one staple line is defined on either side of the midline by a plurality of openings aligned along the longitudinal length of the upper surface wherein the staple channels are curved about the center point and each staple channel in a staple line has the same curvature and the radius of curvature of staple channels increases with distance toward the midline.

According to another aspect of the invention, a surgical stapler is provided. The surgical stapler includes a handle assembly connected to a stapler cartridge assembly. The stapler cartridge assembly has an end effector at the distal end. The end effector includes an upper jaw connected to a lower jaw such that the upper jaw is movable via the handle assembly relative to the lower jaw between an open configuration and a closed configuration. The lower jaw has an upper surface and the upper jaw has an anvil surface. In the closed configuration, a gap is defined between the upper surface and anvil surface for receiving tissue to be stapled. The lower jaw further includes a plurality of staple channels arranged longitudinally along the length of the lower jaw and configured to receive staples. Each staple channel has an opening at the upper surface. A center point and midline are defined by a cross-section taken perpendicular to the longitudinal axis of the end effector with the jaws in a closed configuration. More than one staple line is defined on either side of the midline by a plurality of openings aligned along the longitudinal length of the upper surface wherein the staple channels are curved about the center point and each staple channel has the same curvature about the center point.

According to another aspect of the invention, a surgical stapler is provided. The surgical stapler includes a handle assembly connected to a stapler cartridge assembly. The stapler cartridge assembly has an end effector at the distal end. The end effector includes an upper jaw connected to a lower jaw such that the upper jaw is movable via the handle assembly relative to the lower jaw between an open configuration and a closed configuration. The lower jaw has an upper surface and the upper jaw has an anvil surface. In the closed configuration, a gap is defined between the upper surface and anvil surface for receiving tissue to be stapled. The lower jaw further includes a plurality of staple channels arranged longitudinally along the length of the lower jaw and configured to receive staples. Each staple channel has an opening at the upper surface. A center point and midline are defined by a cross-section taken perpendicular to the longitudinal axis of the end effector with the jaws in a closed configuration. At least one additional point is defined within a cross-section taken perpendicular to the longitudinal axis of the end effector with the jaws in a closed configuration. The at least one additional point is not a center point. More than one staple line is defined on either side of the midline by a plurality of openings aligned along the longitudinal length of the upper surface wherein one or more staple channels are curved about the center point or the at least one additional point. In another variation, one or more staple channels are elliptical about the center point or the at least one additional point. In another variation, the stapler further includes a plurality of staples disposed inside the staple channels and each staple has curved legs that conform to the curvature of the staple channels in which they reside. In another variation, the stapler further includes a plurality of pushers disposed inside the staple channels that are configured to contact and eject staples and each pusher has concentric side surfaces that conform to the curvature of the staple channel in which it resides. In another variation, one or more staple channels are curved about the center point or the at least one additional point and perpendicular to the upper surface. In another variation, one or more staple channels are elliptical about the center point or the at least one additional point and perpendicular to the upper surface. In another variation, one or more staple channels are curved about the center point or the at least one additional point and oblique to the upper surface. In another variation, one or more staple channels are curved about the center point or the at least one additional point and lie in a plane having a compound angle to the upper surface.

According to another aspect of the invention, a surgical stapler is provided. The surgical stapler includes a handle assembly connected to a stapler cartridge assembly. The stapler cartridge assembly has an end effector at the distal end. The end effector includes an upper jaw connected to a lower jaw such that the upper jaw is movable via the handle assembly relative to the lower jaw between an open configuration and a closed configuration. The lower jaw has an upper surface and the upper jaw has an anvil surface. In the closed configuration, a gap is defined between the upper surface and anvil surface for receiving tissue to be stapled. The lower jaw further includes a plurality of staple channels arranged longitudinally along the length of the lower jaw and configured to receive staples. Each staple channel has an opening at the upper surface. A center point and midline are defined by a cross-section taken perpendicular to the longitudinal axis of the end effector with the jaws in a closed configuration. The staple channels are curved about the center point wherein the upper surface of the lower jaw is angled relative to the midline plane toward the anvil surface. In another variation, the upper surface and anvil surface are angled and substantially parallel. In another variation, the upper surface of the lower jaw is concave toward the anvil surface. In another variation, the upper surface is bifurcated such that the upper surface forms two surfaces having an acute angle therebetween. In another variation, the upper surface is bifurcated such that the upper surface forms two surfaces with the apex of the angle being substantially at the midline. In another variation, the upper surface forms three surfaces such that two surfaces have an acute angle therebetween and are interconnected by a third surface defining a chord in the cross-section taken perpendicular to the longitudinal axis.

According to another aspect of the invention, a surgical stapler is provided. The surgical stapler includes a handle assembly connected to a stapler cartridge assembly. The stapler cartridge assembly has an end effector at the distal end. The end effector includes an upper jaw connected to a lower jaw such that the upper jaw is movable via the handle assembly relative to the lower jaw between an open configuration and a closed configuration. The lower jaw has an upper surface and the upper jaw has an anvil surface. In the closed configuration, a gap is defined between the upper surface and anvil surface for receiving tissue to be stapled. The lower jaw further includes a plurality of staple channels arranged longitudinally along the length of the lower jaw and configured to receive staples. Each staple channel has an opening at the upper surface. A center point is defined by a cross-section taken perpendicular to the longitudinal axis of the end effector with the jaws in a closed configuration and the staple channels are curved about the center point. The surgical stapler further includes a plurality of staples disposed inside the staple channels. Each staple has a base with upwardly extending legs. Each staple has an undeformed configuration in which the staple legs are curved to conform to the curvature of the staple channels in which they reside and a deformed configuration in which the staple legs are closed to capture tissue. Actuation of the stapler at the handle assembly moves staples from the undeformed configuration inside the channel against the anvil surface into the deformed configuration. In one variation, each staple has two legs. In another variation, each staple has two legs and the stapler is configured such that one leg contacts the anvil surface before the other leg. In one variation, each staple has four legs. In one variation, each staple has four staple legs and the stapler is configured such that two legs contact the anvil surface before the remaining two legs. In another variation, the staple includes two or four legs and all of the legs are bent to the same side in the deformed configuration. In another variation, the staple includes two or four legs and the staple base is aligned parallel to the longitudinal axis and the staple legs are aligned substantially perpendicular to the longitudinal axis in the deformed configuration. In another variation, the staple includes two legs and the staple forms a substantial B-shaped deformed configuration. In another variation, the staple includes two legs and the staple legs form two open circles. In another variation, the staple includes two legs and the staple legs form two open circles residing in two planes that are parallel to each other and also perpendicular to the base of the staple. In another variation, the staple includes two legs and the staple legs and base are aligned parallel to the longitudinal axis in the deformed configuration.

BRIEF DESCRIPTION OF THE DRAWINGS

FIG. 79 is a side elevational view of a staple according to the present invention.

FIG. 80 is a top perspective view of a deformed staple according to the present invention.

FIG. 81 is top perspective view of a deformed staple according to the present invention.

FIG. 82 is a front elevational view of a deformed staple according to the present invention.

FIG. 83 is a top view of a deformed staple according to the present invention.

FIG. 84 is a side elevational view of a deformed staple according to the present invention.

DETAILED DESCRIPTION OF THE INVENTION

Figures 3, 4:
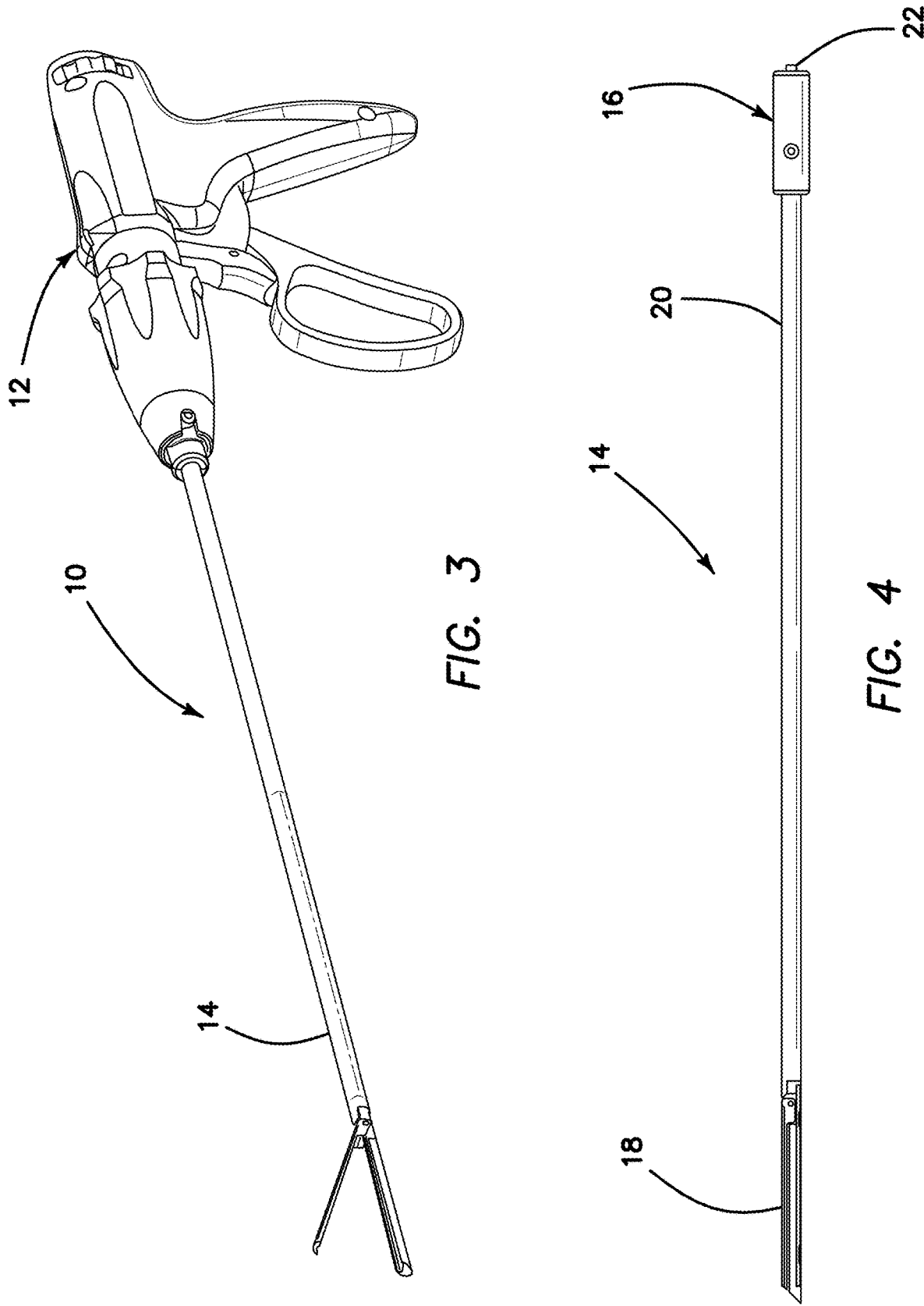
FIG. 3 is a top perspective view of a surgical stapler according to the present invention.
FIG. 4 is a side view of a stapler cartridge assembly according to the present invention.

Referring to FIG. 3, there is shown a perspective view of a surgical stapler 10 according to the present invention. The stapler 10 is comprised of a handle assembly 12 removably connected to a stapler cartridge assembly 14. The handle assembly 12 is configured to control the instrument and actuate the deployment of staples located in the distal end of the stapler cartridge assembly 14. After the staples have been expended from the stapler 10, the stapler cartridge assembly 14 is removed from the handle assembly 12 and a new stapler cartridge assembly 14 is connected to the handle assembly 12 for continued stapling. In an alternative variation, a separate staple cartridge is replaceable from the distal end of the stapler cartridge assembly 14 for continued stapling.

Turning to FIG. 4, the stapler cartridge assembly 14 will now be discussed in detail. The stapler cartridge assembly 14 includes a connector 16 at the proximal end and an end effector 18 at the distal end. An outer tube 20 is connected to the end effector 18 at the distal end and to the connector 16 at the proximal end. An actuator shaft 22 is disposed inside the lumen of the outer tube 20. The outer tube 20 is substantially cylindrical having an outer diameter of approximately 5-10 mm. The actuator shaft 22 is configured to slide longitudinally relative to the outer tube 20. Detail of the proximal end of the stapler cartridge assembly 14 is shown in FIG. 5.

Figures 5, 6:
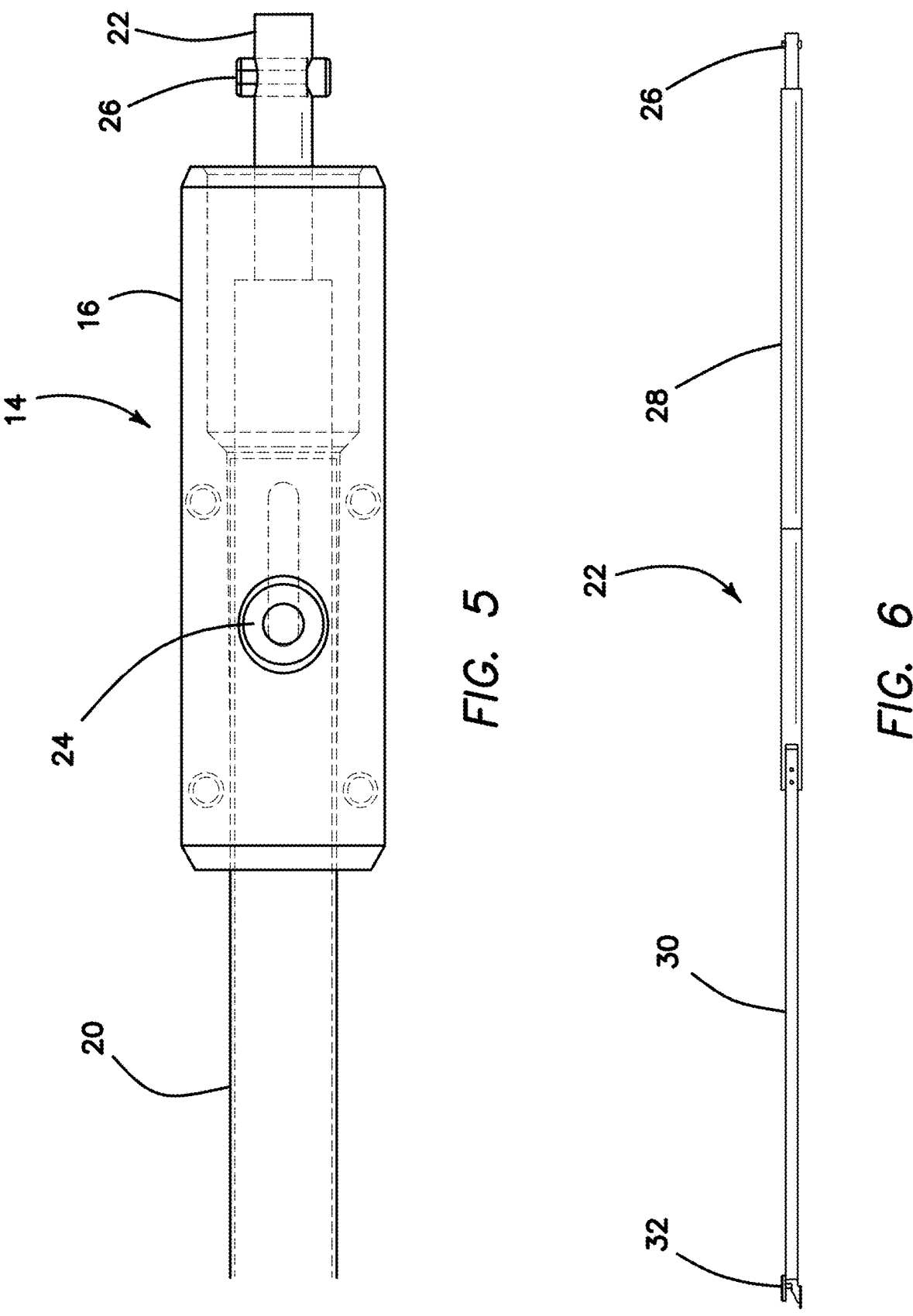
FIG. 5 is semi-transparent side view a proximal end of a stapler cartridge assembly according to the present invention.
FIG. 6 is side view of an actuator shaft and I-beam slider according to the present invention.
Figures 7, 8:
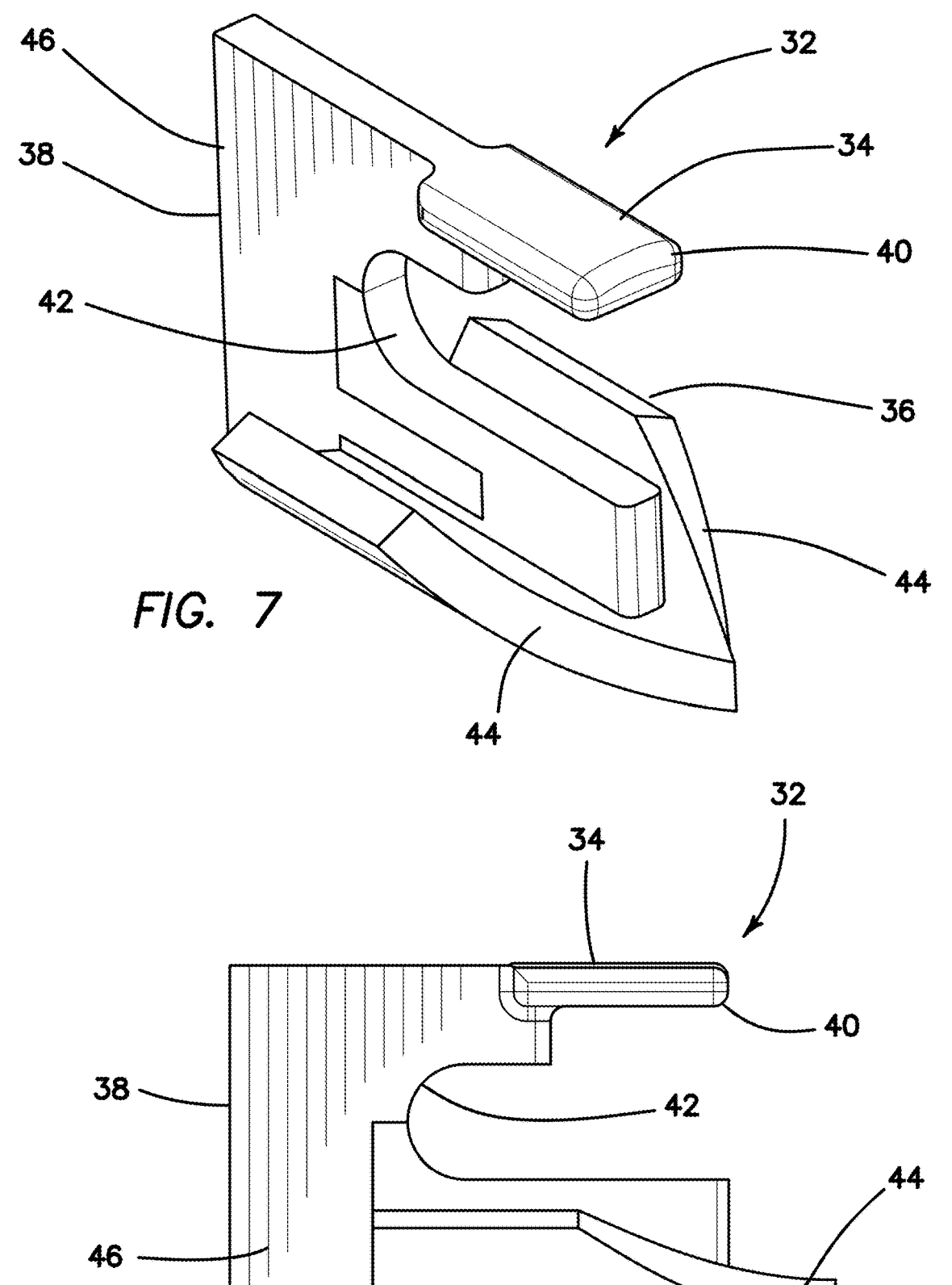
FIG. 7 is a top perspective view of an I-beam slider according to the present invention.
FIG. 8 is a side view of an I-beam slider according to the present invention.
Figure 9:
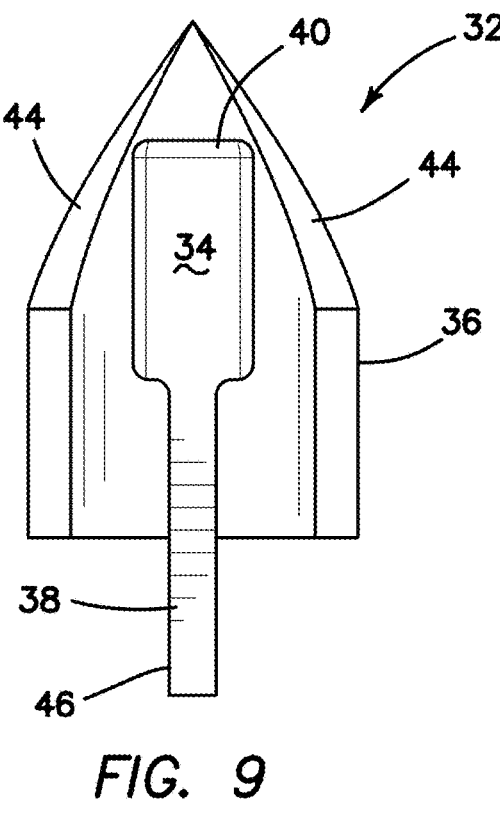
FIG. 9 is a top view of an I-beam slider according to the present invention.
Figure 10:
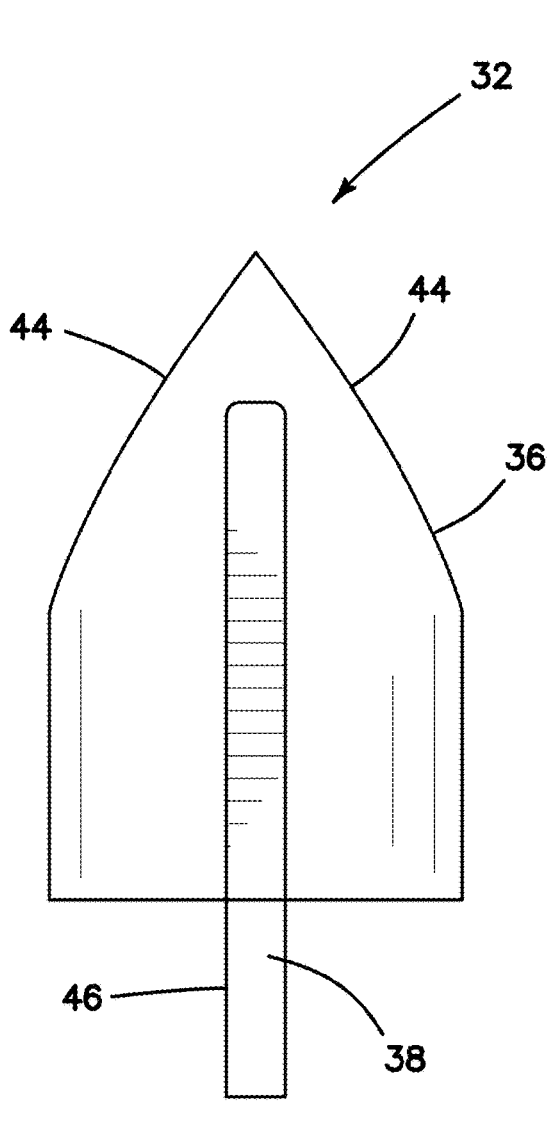
FIG. 10 is a bottom view of an I-beam slider according to the present invention.

Turning to FIG. 5, the proximal end of the stapler cartridge assembly 14 is shown. The connector 16 includes a bolt 24 that extends laterally outwardly from the outer surface of the connector 16. A similar bolt 24 extends on the opposite side of the connector 16 and is not visible in FIG. 5. The bolt 24 is configured for a bayonet-like connection with the handle assembly 12 of the stapler 10 that includes a complementary slot for receiving the bolt 24 to secure the cartridge assembly 14 to the handle assembly 12. FIG. 5 also illustrates the actuator shaft 22 moved proximally relative to the outer tube 20 when compared to FIG. 4 in which the actuator shaft 22 is shown to be moved more distally relative to the outer tube 20. As seen in FIG. 5, the proximal end of the actuator shaft 22 includes a bolt 26 that extends laterally outwardly from the actuator shaft 22. The bolt 26 is configured for a bayonet-like connection with an actuator shaft of the handle assembly 12 which includes a complementary slot for receiving the bolt 26. Mating the bolt 24 of the connector 16 to handle assembly 12 simultaneously mates the bolt 26 of the actuator shaft 22 to the actuator shaft of the handle assembly 12. When connected to the handle assembly 12, the handle assembly 12 is used to move the actuator shaft 22 forward and backward inside the outer tube 20 to effect opening and closing of the distal jaw-like members and the deployment of staples.

Turning to FIG. 6, the actuator shaft 22 will now be described. The actuator shaft 22 is an elongated shaft having a substantially cylindrical proximal portion 28 having actuator bolts 26 at the proximal end for connection with the actuator of the handle assembly 12. The substantially cylindrical portion 28 is sized for a concentric close fit inside the lumen of the outer tube 20. The cylindrical portion 28 is connected with pins to an extended I-beam portion 30 toward the distal end of the actuator shaft 22. The distal end of the actuator shaft 22 includes an I-beam 32 connected to the extended I-beam portion 30.

Figure 11:
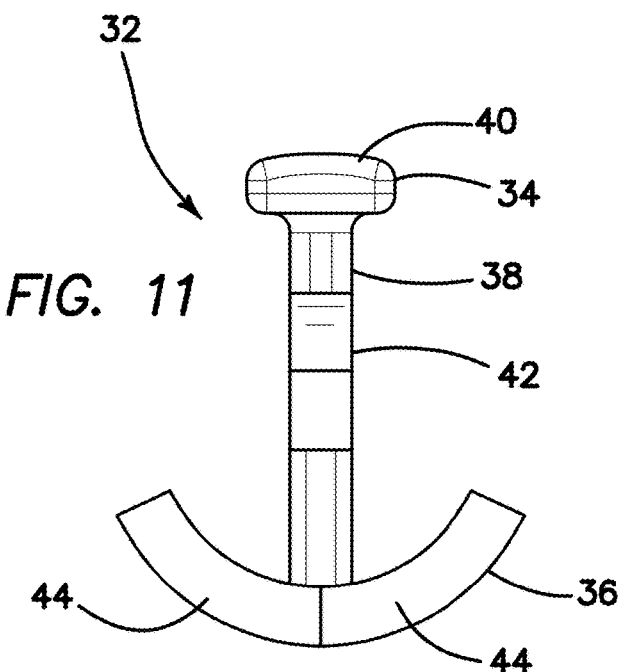
FIG. 11 is a front view of an I-beam slider according to the present invention.
Figures 12, 13:
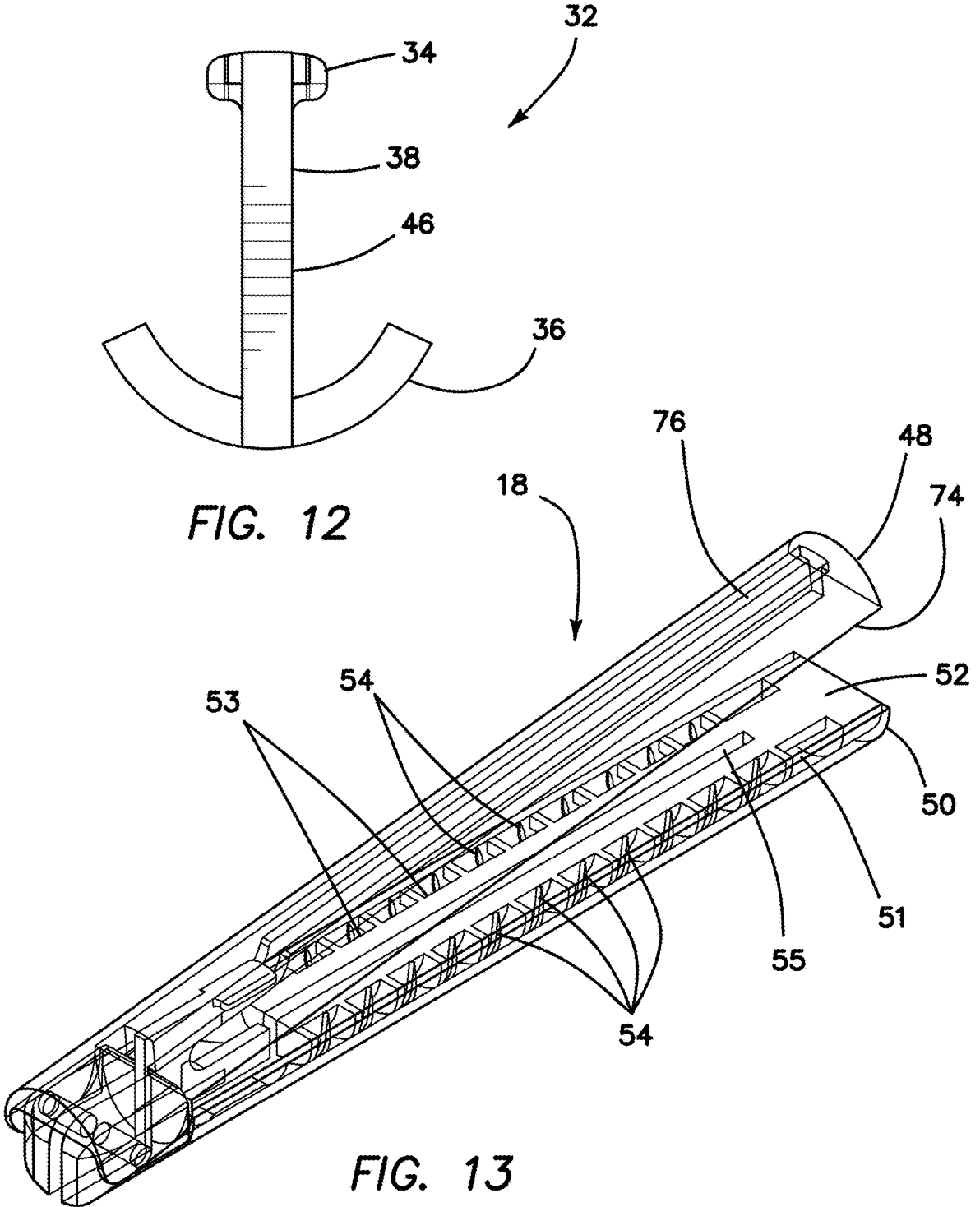
FIG. 12 is a rear view of an I-beam slider according to the present invention.
FIG. 13 is a semi-transparent, top perspective view of an end effector with jaws in an open position according to the present invention.
Figure 14:
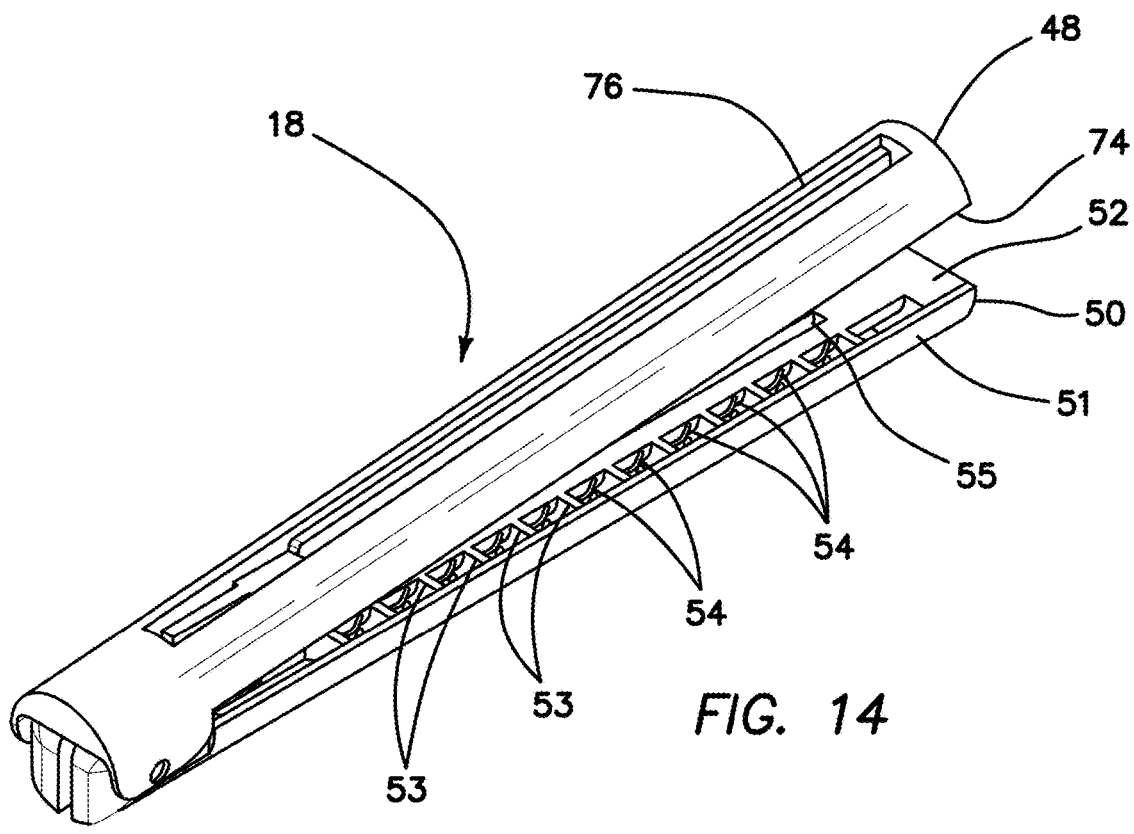
FIG. 14 is a top perspective view of an end effector with jaws in an open position according to the present invention.
Figure 15:
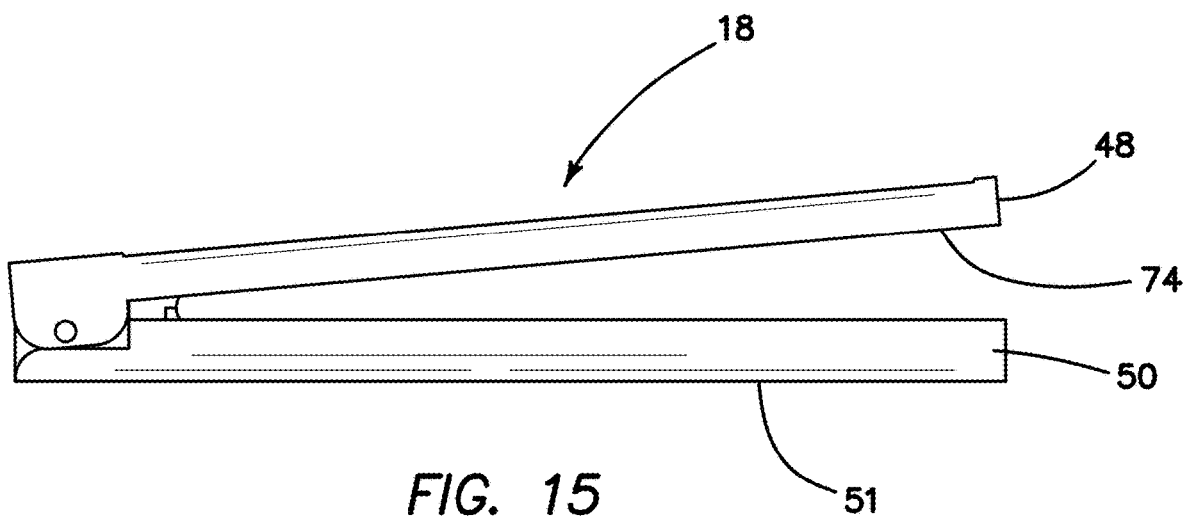
FIG. 15 is a side view of an end effector with jaws in an open position according to the present invention.

Turning now to FIGS. 7-12, the I-beam 32 will now be described. The I-beam 32 includes a top portion 34 and a bottom portion 36 interconnected by a middle portion 38. The top portion 34 includes a beveled front end 40 and a curved top. The middle portion 38 includes a blade 42 which would include a sharp leading edge that is shown as a blunt surface in FIGS. 7-12. At the back end, the middle portion 38 includes a portion 46 for connecting with the extended I-beam portion 30 as shown in FIG. 6. The bottom portion 36 leads the front end of the I-beam 32 and includes a curved bottom with a convex outer surface and a leading surface 44 that resembles a snowplow. The leading surface 44 includes two converging surfaces that meet at a vertical line or tip. Each converging surface extends outwardly from the tip in a helical spiral fashion, that is, it not only extends upwardly, but also, spirals or curves or rotates with respect to the longitudinal axis of the I-beam 32 to create the helix wedge design. The front-elevational view of the I-beam is shown in FIG. 11 which illustrates the profile to be substantially in the shape of a capital letter "I" having a lower curved portion. The I-beam slides longitudinally inside the end effector 18 and as such may be called a slider. The I-beam/slider 32 is configured to urge staples out of the end effector 18 via the leading surface 44.

Figures 16, 17:
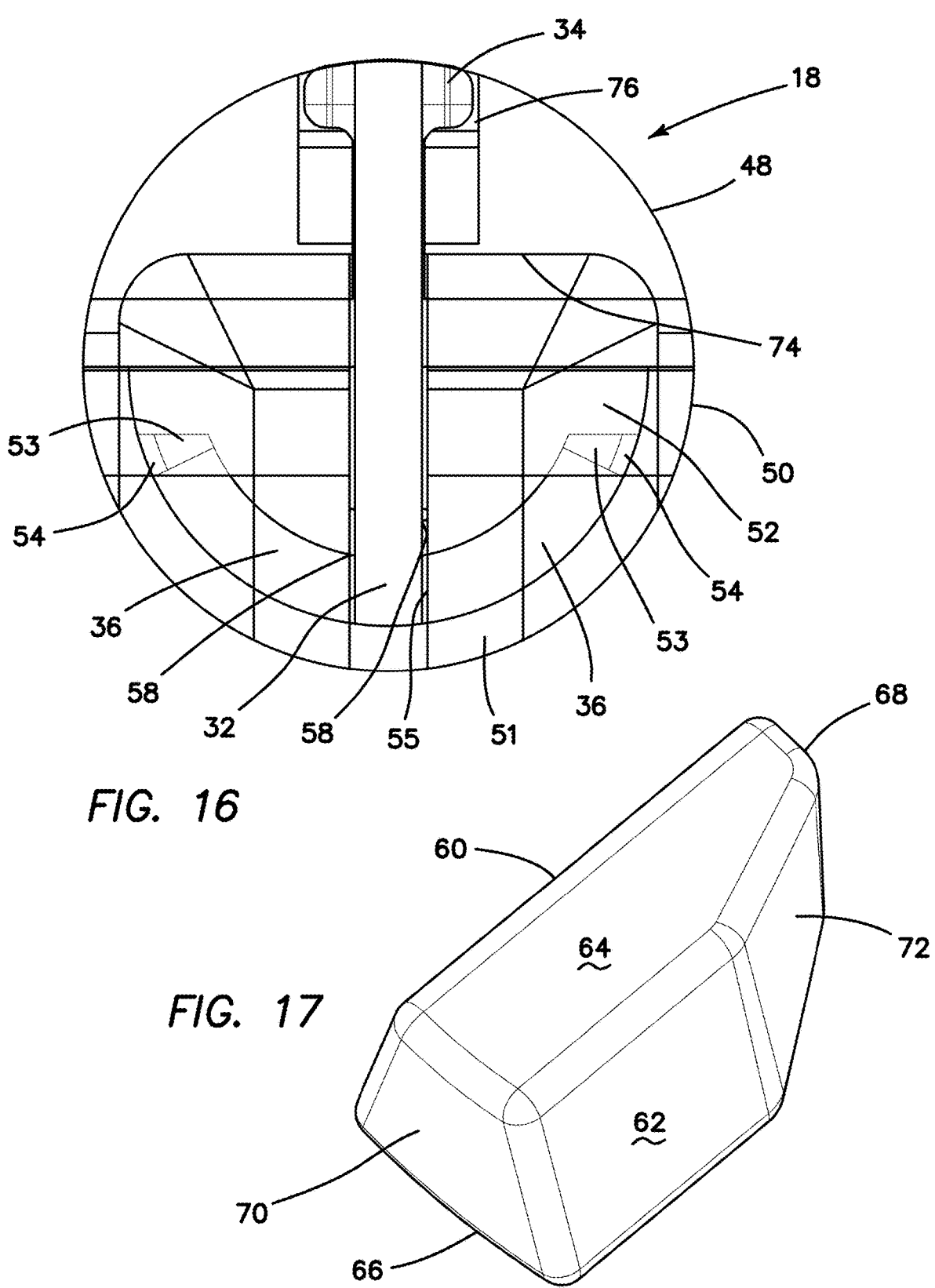
FIG. 16 is a semi-transparent, cross-sectional view of an end effector with jaws in a closed position according to the present invention.
FIG. 17 is a perspective view of a pusher according to the present invention.
Figures 18, 19, 20:
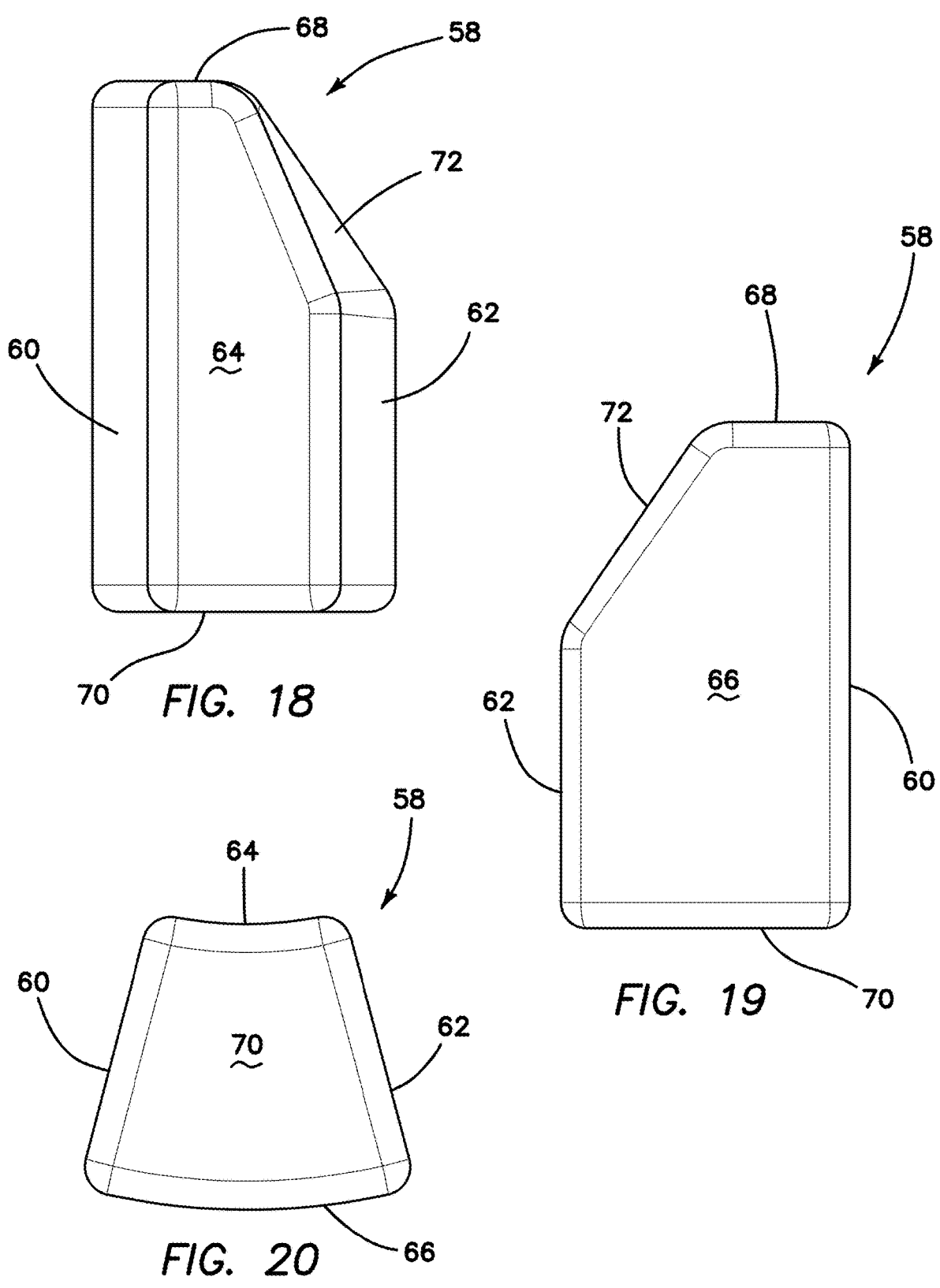
FIG. 18 is a side view of a pusher according to the present invention.
FIG. 19 is a side view of a pusher according to the present invention.
FIG. 20 is an end view of a pusher according to the present invention.

Turning now to FIGS. 13-16, the end effector 18 will be described. The end effector 18 includes an upper jaw 48 hinged to a lower jaw 50. When the jaws 48, 50 are in a closed orientation, they form a substantially circular cross-section when viewed from the end. The lower jaw 50 includes a staple housing or staple cartridge 52 containing a plurality of staples 54. The lower jaw 50 comprises a hollow semi-cylindrical shell or outer lower jaw 51 and a conformingly-shaped inner lower jaw or cartridge 52 disposed inside the outer lower jaw 51. The inner lower jaw 52 may or may not be removable and replaceable like a cartridge for introducing more staples 54 for continued firing. In a variation in which the inner lower jaw 52 is fixed, the entire stapler 10 is disposable after a single firing or, alternatively, the stapler cartridge assembly 14 serves as a disposable cartridge and is removed and replaced for continued firing. The inner lower jaw 52 includes a plurality of channels 53 or staple pathways configured to receive staples 54 and serve as a guide for delivering the staples 54 towards the upper jaw 48. Each channel 53 forms a top opening at the top surface of lower jaw 50 through which a staple 54 exits the lower jaw 50. The inner lower jaw 52 includes a central channel 55 that extends longitudinally and is configured to receive a longitudinally-translating I-beam 32. The bottom of the inner lower jaw 52 is spaced from the outer lower jaw 51 to form a gap that is conformingly-shaped to receive the bottom portion 36 of the I-beam 32 as it translates longitudinally. Each channel 53 extends between the top opening and a bottom opening. The bottom opening is in communication with the gap between the inner and outer lower jaw. Each channel 53 is curved and transcribes an arc between the top opening of the channel and the bottom opening of the channel as shown in FIG. 16. In a cross-section taken perpendicular to the longitudinal axis of the end effector 18, the channel 53 has a radius of curvature that substantially matches the radius of curvature of the outer lower jaw 51 and forms a circumferential delivery pathway for the staple. In one variation, the channels 53 are concentric about the center point of a cross-section taken perpendicular to the longitudinal axis of the closed jaws 48, 50. A four-pronged staple 54 is shown residing in the channel 53 in FIG. 13. A pusher 58 is also disposed inside each channel 53. Two pushers 58 are slightly visible in FIG. 16. The pusher 58 is configured to contact the leading surface 44 of the I-beam slider 32 and in turn contact at least one staple 54.

Figures 21, 22, 23:
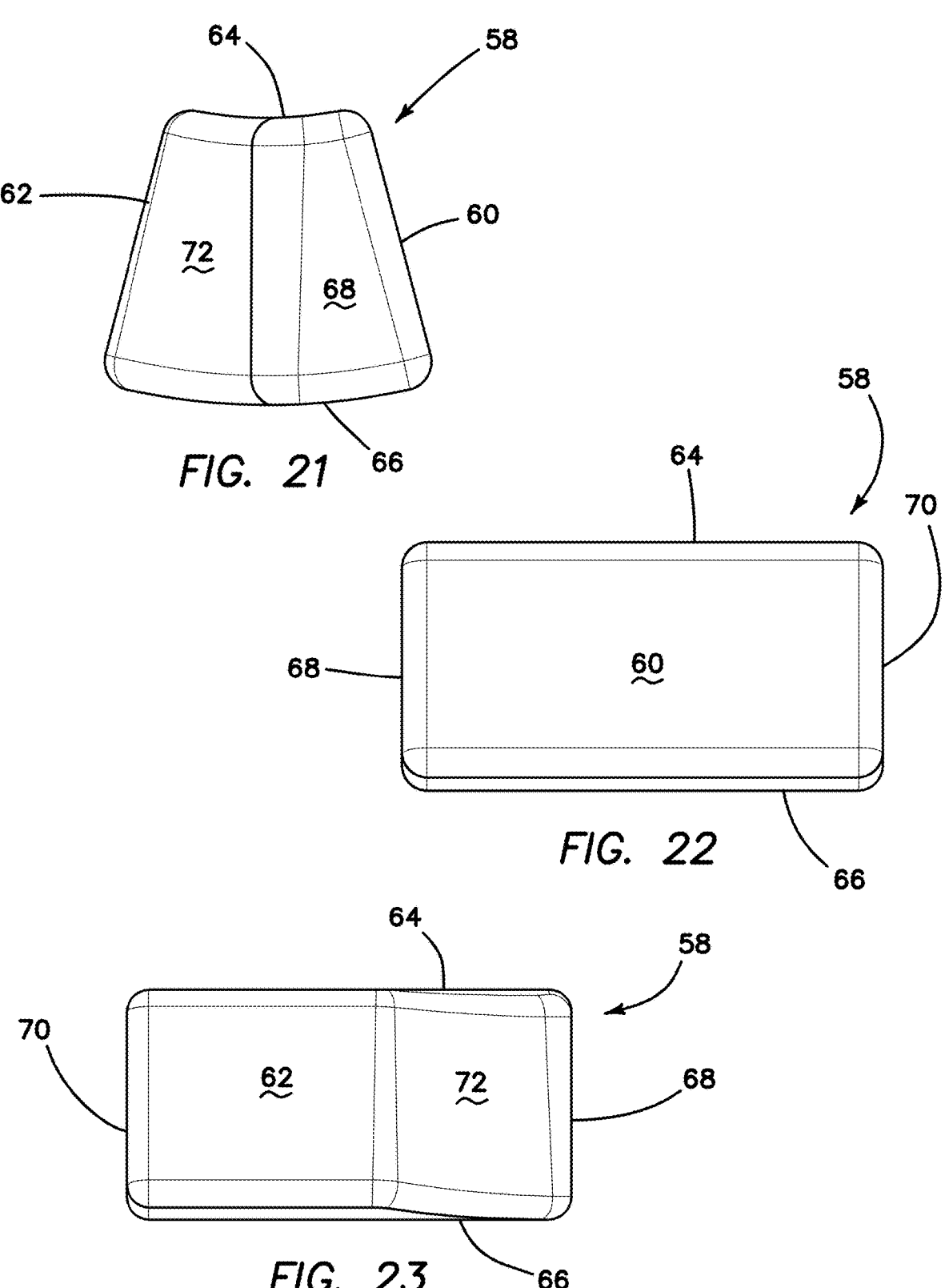
FIG. 21 is an end view of a pusher according to the present invention.
FIG. 22 is a top view of a pusher according to the present invention.
FIG. 23 is a bottom view of a pusher according to the present invention.
Figures 24, 25:
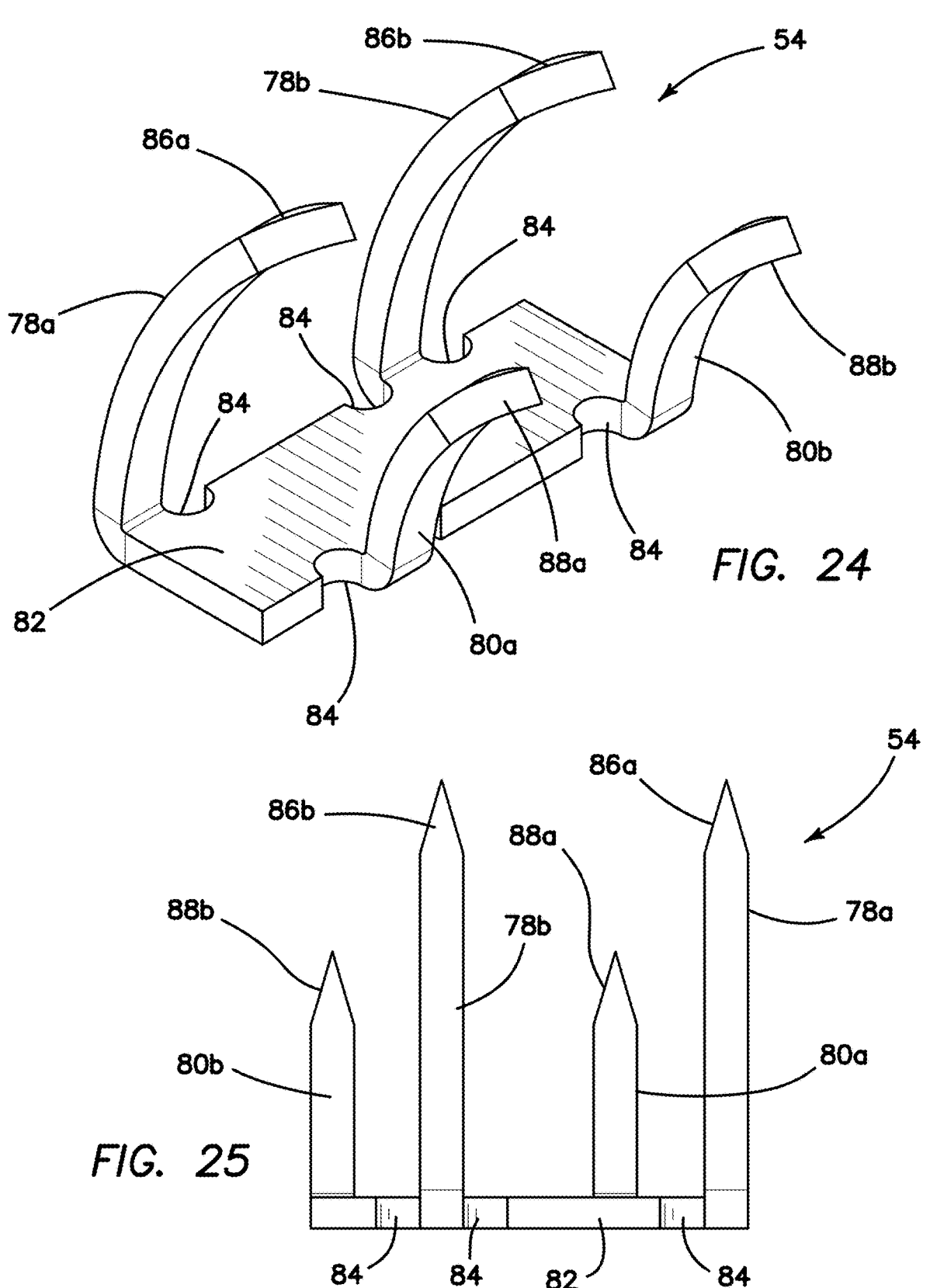
FIG. 24 is a top perspective view of a staple according to the present invention.
FIG. 25 is a side view of a staple according to the present invention.

Turning to FIGS. 17-23, there is shown a pusher 58 according to the present invention. The pusher 58 is a wedge-shaped object configured for interfacing between the I-beam slider 32 and one or more staples 54. The pusher 58 includes a top surface 60 and a bottom surface 62 interconnected by two side surfaces 64, 66 and two end surface 68, 70. The bottom surface 62 includes an I-beam slider contacting surface 72 configured to contact the leading surface 44 of the I-beam slider 32. The I-beam slider contacting surface 72 is shaped to conform to the leading surface 44. If the leading surface 44 of the I-beam slider 32 is helical in shape as described above, then the contacting surface 72 is also helical. The top surface 60 is configured to contact one or more staples 54 and as such comprises a staple contacting surface. Both the top surface 60 and the bottom surface 62 including the contacting surface 72 is slightly angled with respect to side surface 66 and converge slightly towards side surface 64. As can be seen in FIG. 21, the side surface 64 is slightly concave and the opposite side surface 66 is slightly convex. Both side surfaces 64, 66 are concentric with respect to each other. In one variation, the side surfaces 64, 66 are concentric with respect to the center point of a cross-section taken perpendicular the longitudinal axis of the jaws 48, 50 with the jaws 48, 50 in a closed configuration. In one variation, the side surfaces 64, 66 have a curvature that substantially matches the curvature of the channel 53 in which it resides. In one variation, the channel 53 is circumferential to a cross-section perpendicular to the longitudinal axis of the jaws 48, 50 with the jaws 48, 50 in a closed configuration and the side surfaces 64, 66 of the pusher substantially match the circumferential curvature. The end surfaces 68 and 70 are substantially parallel and perpendicular. When urged by the I-beam slider 32, each pusher 58 contacts a staple 54 and travels smoothly within its respective channel 53.

Referring back to FIGS. 13-16, the upper jaw 48 will now be described. The upper jaw 48 is substantially semi-cylindrical in shape to conform to a cylindrical lumen of a cannula in which it is inserted. The upper jaw 48 includes a central slot 76 that extends longitudinally. The central slot 76 is conformingly shaped and configured to receive the top portion 34 of the I-beam 32 and at least a portion of the narrower middle portion 38 of the I-beam 32 such that the I-beam 32 is capable of longitudinal movement relative to the upper jaw 48 inside and along the central slot 76. The central slot 76 includes an open proximal end which is ramped and configured to cam against the beveled front end 40 of the I-beam 32. The upper jaw 48 is spring biased in an open orientation with respect to the lower jaw 50 and as the beveled front end 40 of the I-beam 32 enters the central slot 76, and in particular, the top portion 34 enters the wider upper end of the central slot 76, the upper and lower jaws 48, 50 are forced to close. Back and forth movement of the I-beam 32, into and out of the central slot 76 or against the proximal opening of the central slot 76, opens and closes the end effector 18 allowing the user to grasp and release tissue and reposition the stapler 10. With the end effector 18 in the closed configuration, the I-beam 32 is capable of further longitudinal translation within the central slot 76. Following the ejection of staples 54, the I-beam 32 is retracted proximally via the handle assembly 12 and as the I-beam 32 exits the central slot 76 the spring biased upper jaw 48 moves into an open orientation. Following the ejection of staples 54 and retraction of the I-beam 32, repeated forward translation of the I-beam 32 inside the central slot 76 is prevented by a lock-out mechanism to avoid inadvertent use of an already-fired cartridge.

Figure 44:
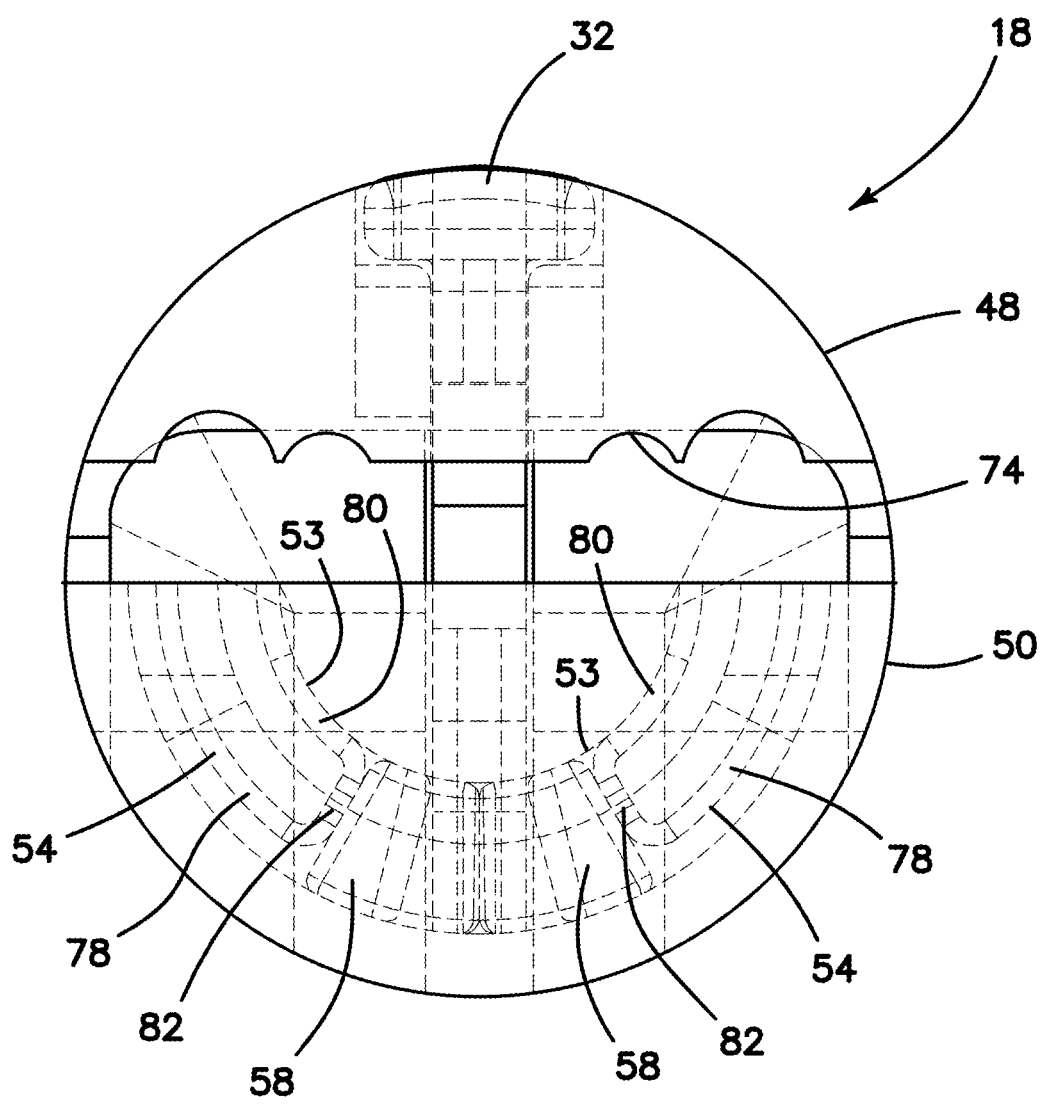
FIG. 44 is a partially transparent, cross-sectional view of an end effector according to the present invention.
Figures 45, 46:
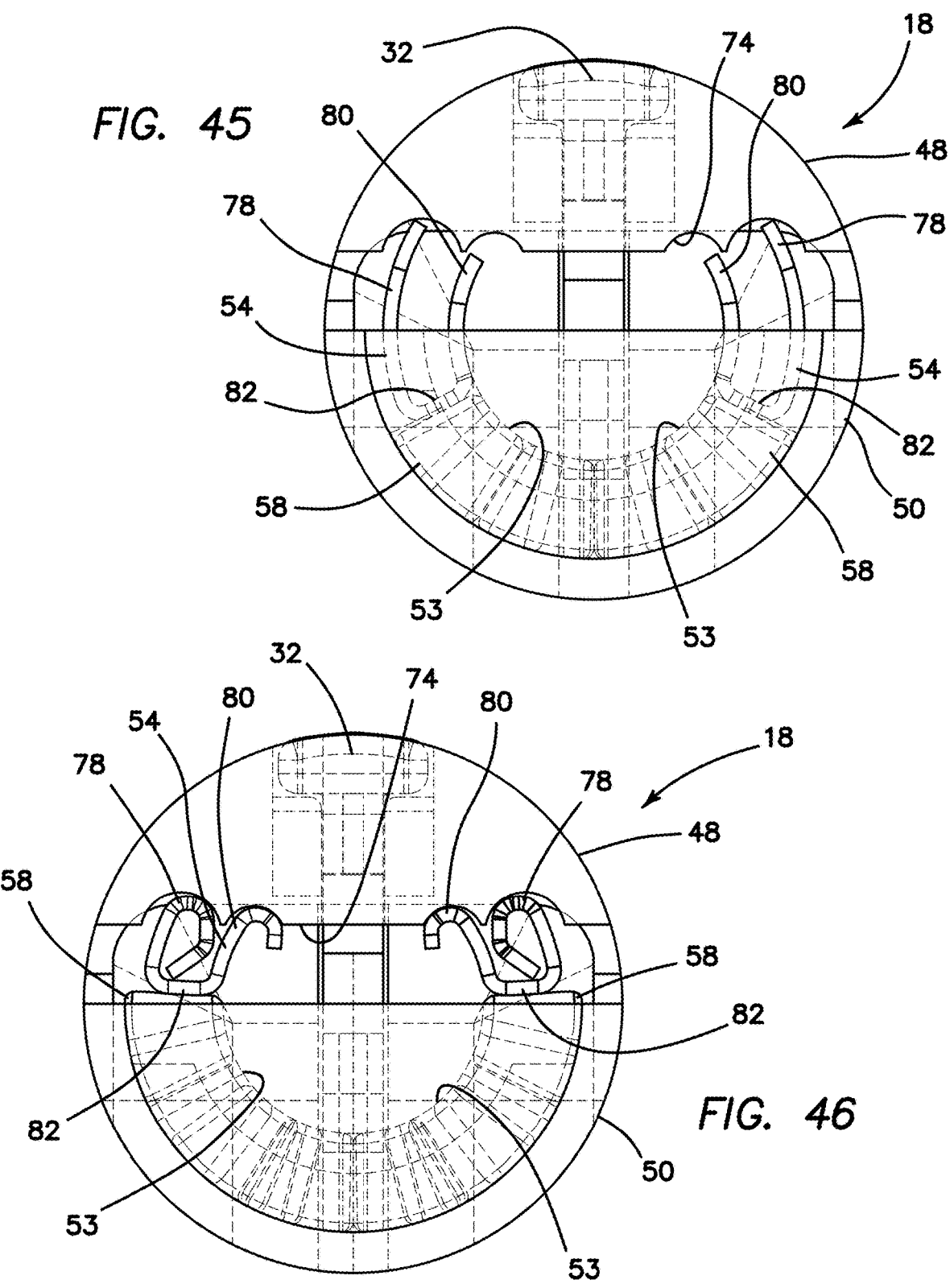
FIG. 45 is a partially transparent, cross-sectional view of an end effector according to the present invention.
FIG. 46 is a partially transparent, cross-sectional view of an end effector according to the present invention.

Also, with reference to FIGS. 44-46, the upper jaw 48 further includes an inner anvil surface 74 or plate that faces and is spaced apart from the lower jaw 50 when in the closed position. The anvil surface 74 is configured to receive the legs of a staple 54 and guide, deflect, angulate, bend, crimp or clinch the staple legs as the staple is urged through tissue against the anvil surface 74. To facilitate the formation of staples 54 to secure tissue, a plurality of staple-forming pockets as shown in FIGS. 44-46 are included in the anvil surface 74. These surface formations of a typical anvil aid in the deformation of the staple as it is deployed to achieve proper staple closure. The staple-forming pockets are aligned with the exit openings of channels 53 in the lower jaw 50. Any misalignment between the staple-forming pockets and the ejecting staple leads to the staples missing the staple forming pockets and may result in catastrophic failure of the staple line. The staple-forming pockets generally include two adjacent staple leg forming cups having a curved or sloped channeling surface formed around the perimeter of each of the staple forming cups. The two adjacent staple leg forming cups form a dog bone shape that facilitates the formation of consistent B-shaped staples from generally square-cornered U-shaped undeformed staples. If four-pronged staples are deployed then the anvil surface 74 includes four adjacent staple forming cups aligned with the ejecting staple legs. Separate staple-forming pockets are provided at each staple forming location opposite the cartridge channels 53 of the lower jaw 50.

Figure 26:
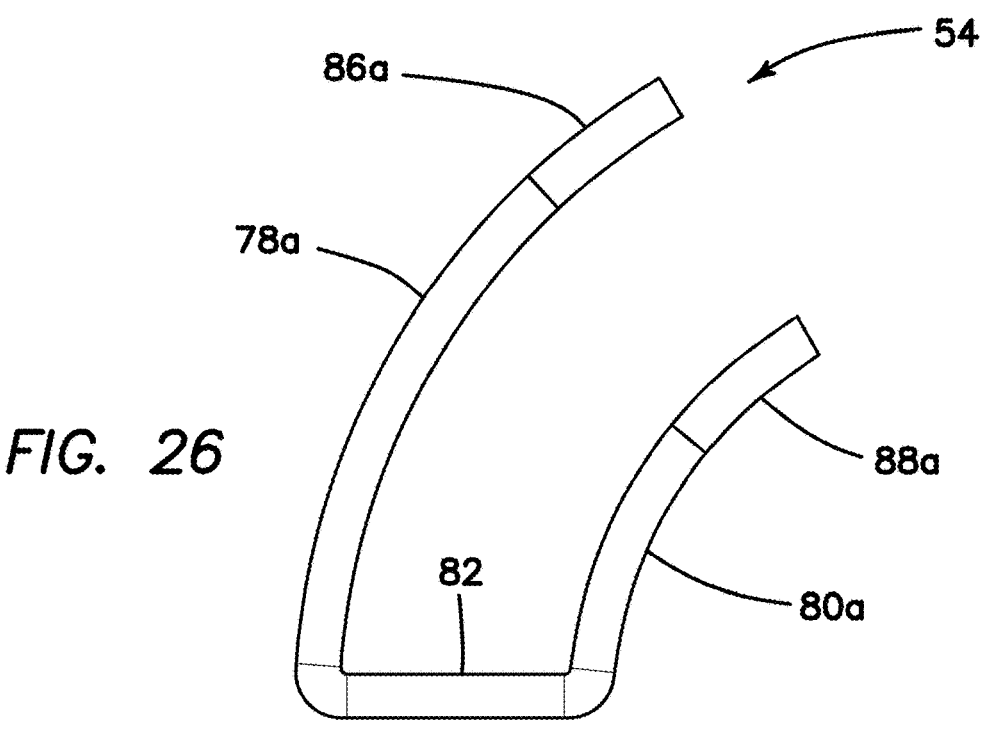
FIG. 26 is an end view of a staple according to the present invention.
Figure 27:
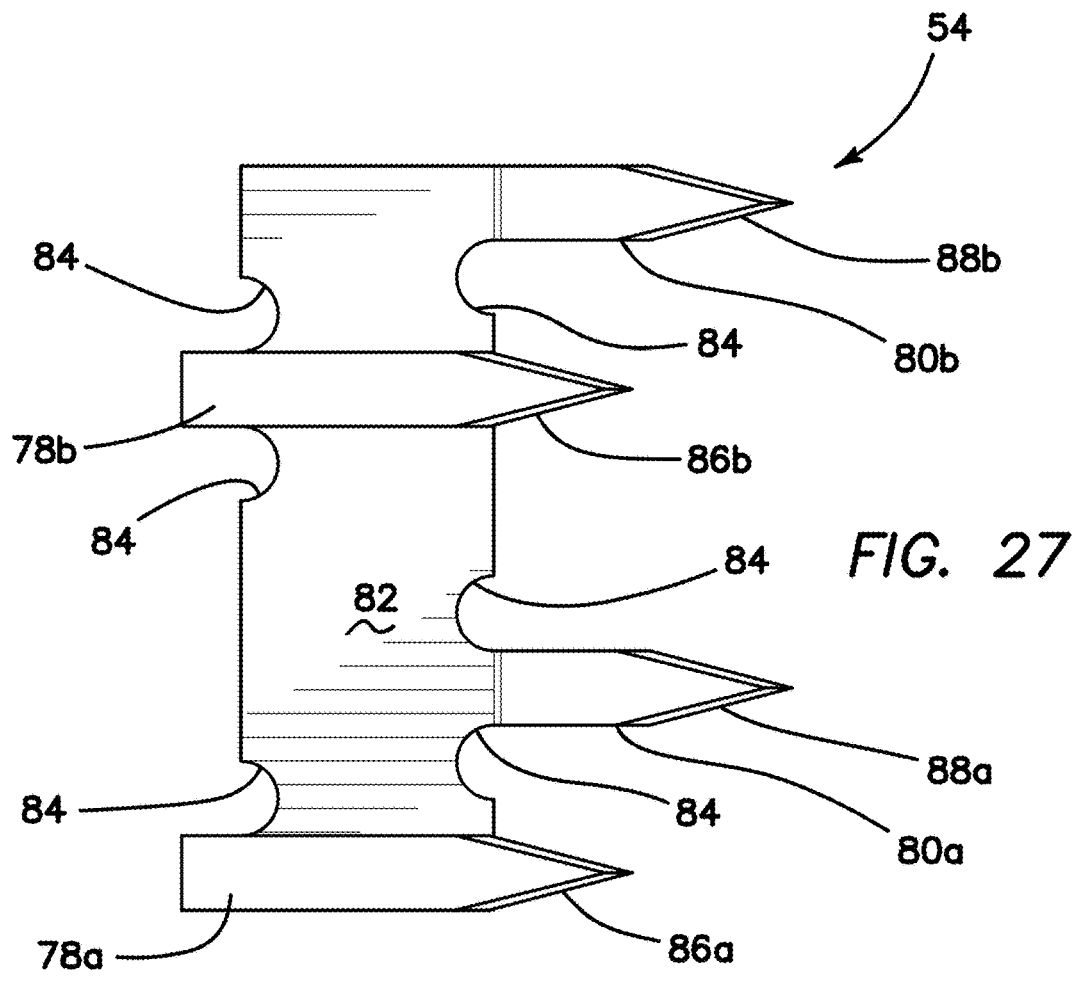
FIG. 27 is a top view of a staple according to the present invention.

Referring now to FIGS. 24-27, a staple 54 according to the present invention will be described. The staple 54 is a four-pronged staple 54 shown in its undeformed or open condition. The four-pronged staple 54 includes two longer first legs 78A, 78B and two shorter second legs 80A, 80B interconnected by a base 82. The two longer first legs 78A, 78B are staggered with respect to the two shorter second legs 80A, 80B such that when deformed or closed against the anvil surface 74, the first legs 78A, 78B do not contact the adjacent second legs 80A, 80B. The base 82 serves as a caming surface for engagement with a pusher 58. The longer and shorter legs 78A, 78B, 80A, 80B all extend upwardly from the base 82 and curve to one side. In one variation, the longer legs 78A, 78B are concentric with the shorter legs 80A, 80B. In one variation, the legs 78A, 78B, 80A, 80B are concentric with respect to the center point of a cross-section taken perpendicular the longitudinal axis of the jaws 48, 50 with the jaws 48, 50 in a closed configuration. In one variation, the legs 78A, 78B, 80A, 80B have a curvature that substantially matches the curvature of the channel 53 in which the staple 54 resides. As seen in FIG. 26, the legs 78A, 78B, 80A, 80B are curved to the right with each leg having a concave surface and a convex surface interconnected by two side surfaces. Each leg 78A, 78B, 80A, 80B is angled in the same direction with respect to the base 82. Each leg intersects with the base 82 and, at the point of intersection, a notch 84 is formed in the base 82 on one or more sides of each leg for manufacturing purposes. The two side surfaces of each leg converge to form a sharp tip at a line intersection at the free distal end of the leg. Each of the legs 78A, 78B, 80A, 80B has their respective tip 86A, 86B, 88A, 88B. The tip begins where the side surfaces begin to taper or decrease in cross-sectional area in the direction distally along the leg. The tips 86A, 86B, 88A, 88B may be formed in any manner and may have any other geometric shape that is suitable for puncturing and penetrating tissue through which the staple is delivered.

Still referencing FIGS. 24-27, the longer first legs 78A, 78B are approximately 0.097 inches long and the shorter second legs 80A, 80B are approximately 0.050 inches long having a central angle with respect to the base of approximately 60 degrees. The ratio of the shorter second legs 80A, 80B to the longer first legs 78A, 78B is approximately ½. The overall length of the base 82 is approximately 0.100 inches and in one variation each leg 78A, 78B, 80A, 80B is concentric about the center point of a cross-section taken perpendicular to the longitudinal axis of the jaws 48, 50 in a closed orientation. The radius of curvature of the outer surface of the first longer legs 78A, 78B is approximately 0.115 inches. The radius of curvature of the outer surface at the intersections with the base 82 is approximately 0.009 inches. The radius of curvature of the inner surface of the second shorter legs 80A, 80B is approximately 0.065 inches. The distance between the side surfaces or thickness of the legs is approximately 0.010 inches. The distance between the inner surface and the outer surface or width of the legs is approximately 0.015 inches.

Figure 28:
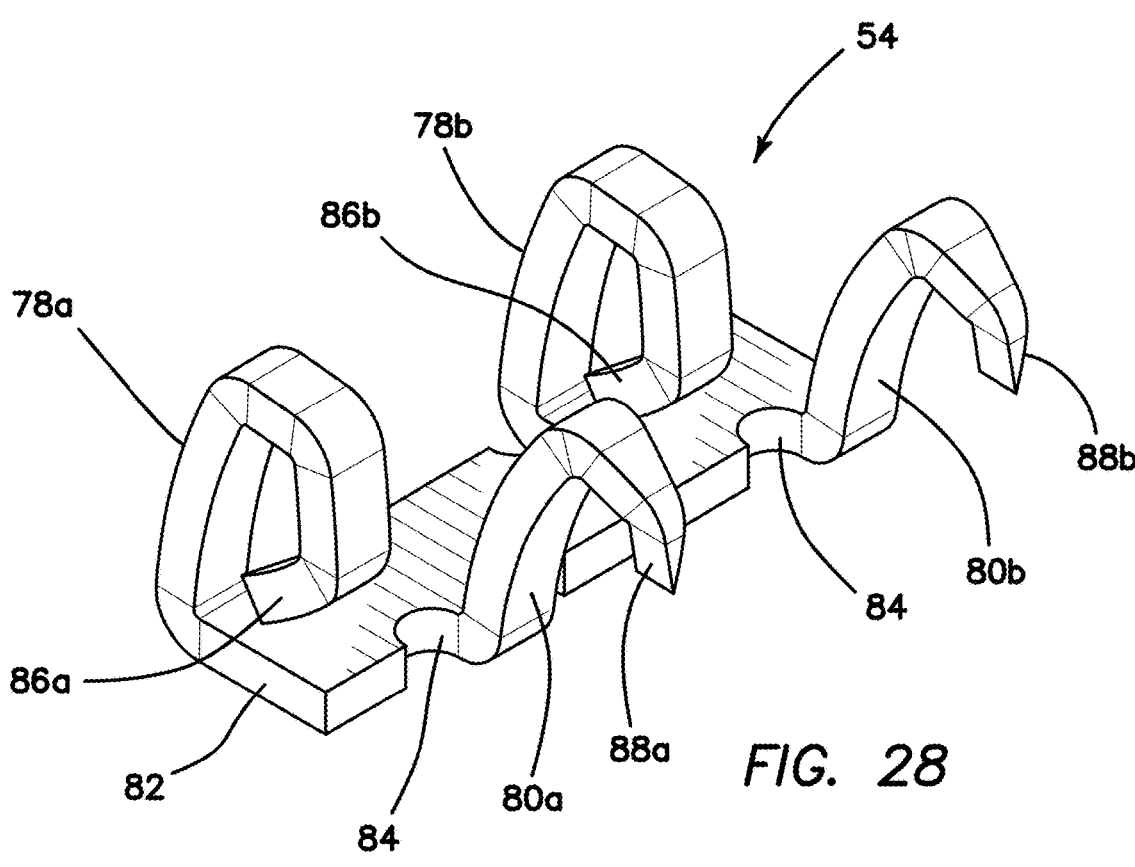
FIG. 28 is a top perspective view of a deformed staple according to the present invention.
Figure 29:
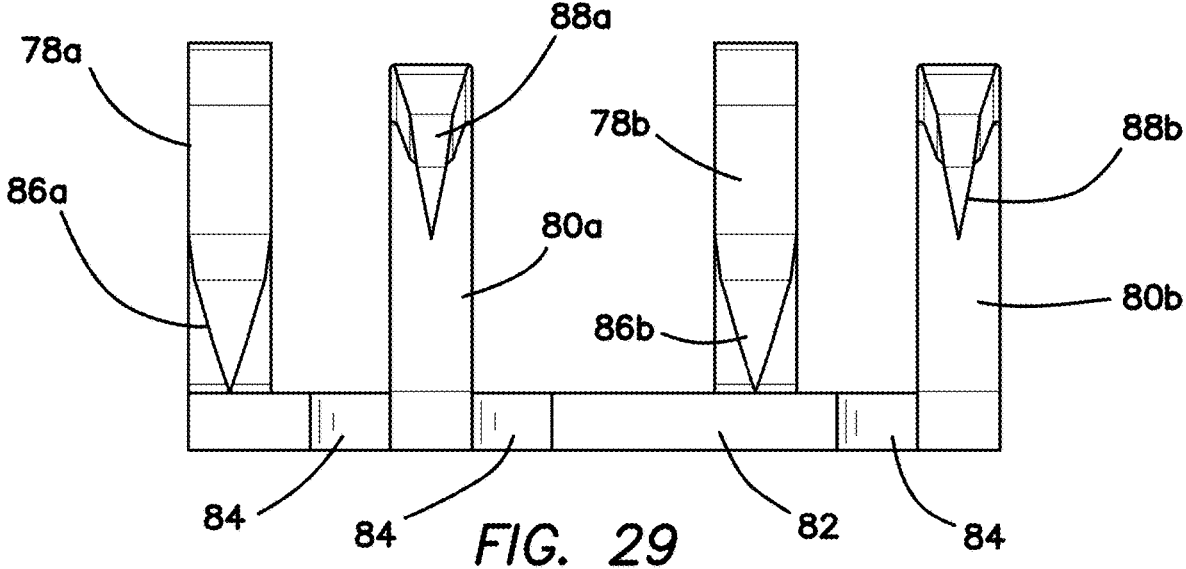
FIG. 29 is a side view of a deformed staple according to the present invention.
Figures 30, 31:
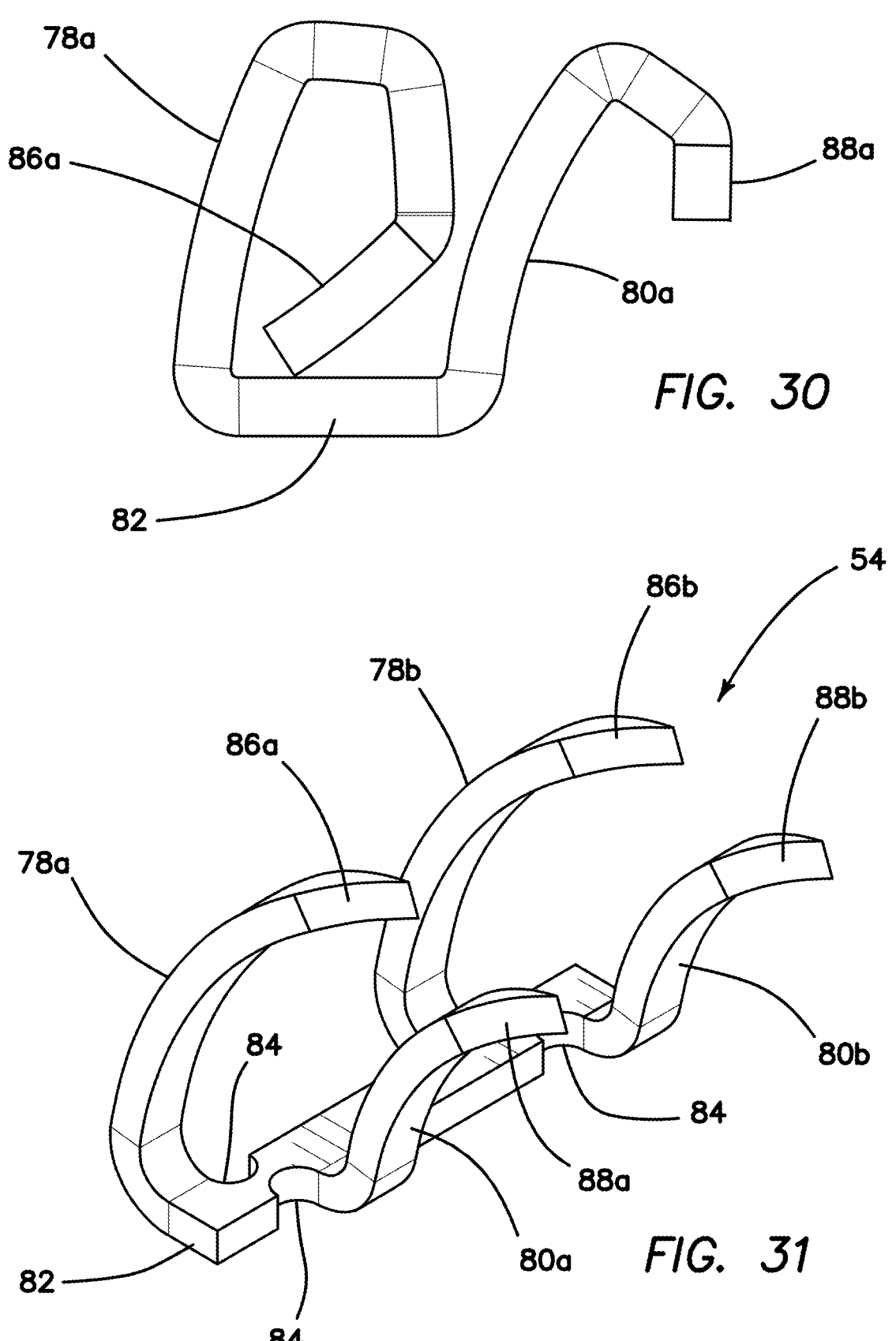
FIG. 30 is an end view of a deformed staple according to the present invention.
FIG. 31 is a top perspective view of a staple according to the present invention.

Turning now to FIGS. 28-30, there is shown the staple 54 of FIGS. 24-27 in a second or deformed configuration after complete actuation of the stapler. Deployment of the four-pronged staple 54, which will be discussed in greater detail below, results in the shorter legs 80A, 80B contacting the anvil surface 74 and being deformed. The shorter legs 80A, 80B are deflected vertically downwardly toward the base 82 and laterally away from the base 82, away from the longitudinal axis of the staple 54. The shorter legs 80A, 80B bend to form a curl having a C-shape with the tips 88A, 88B pointing substantially downwardly. The tips 88A, 88B are not located above the base 82 in the deformed configuration. The longer legs 78A, 78B will contact the anvil surface 74 and with continued movement of the slider 32 will deform such that the longer legs 78A, 78B are deflected vertically downwardly and laterally toward the longitudinal axis of the base 82. The longer legs 78A, 78B bend to form a deeper curl relative to the deformed shorter legs 80A, 80B. Also, the tips 86A, 86B of the longer legs 78A, 78B are vertically closer to the base 82 than the tips 88A, 88B of the shorter legs 80A, 80B. The tips 86A, 86B of the longer legs 78A, 78B are resident above the base 82 in the deformed configuration. All of the legs 78A, 78B, 80A, 80B are deflected in the same direction. For example, as shown in the end view of FIG. 30, the legs 78A, 78B, 80A, 80B are deflected toward the right. Pockets in the anvil surface 74 that are aligned with the exit opening in the top surface of the lower jaw, guide and aid in the proper deformation of a staple.

Figure 32:
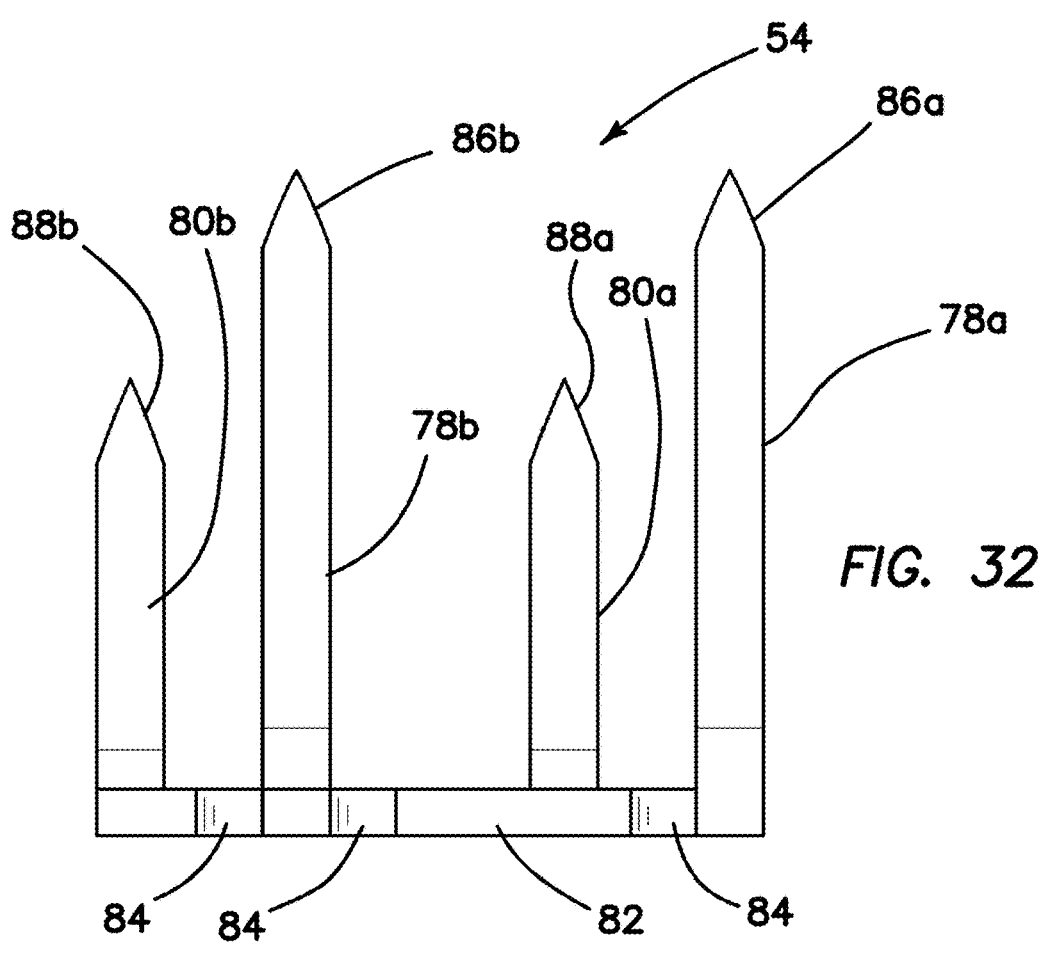
FIG. 32 is a side view of a staple according to the present invention.
Figure 33:
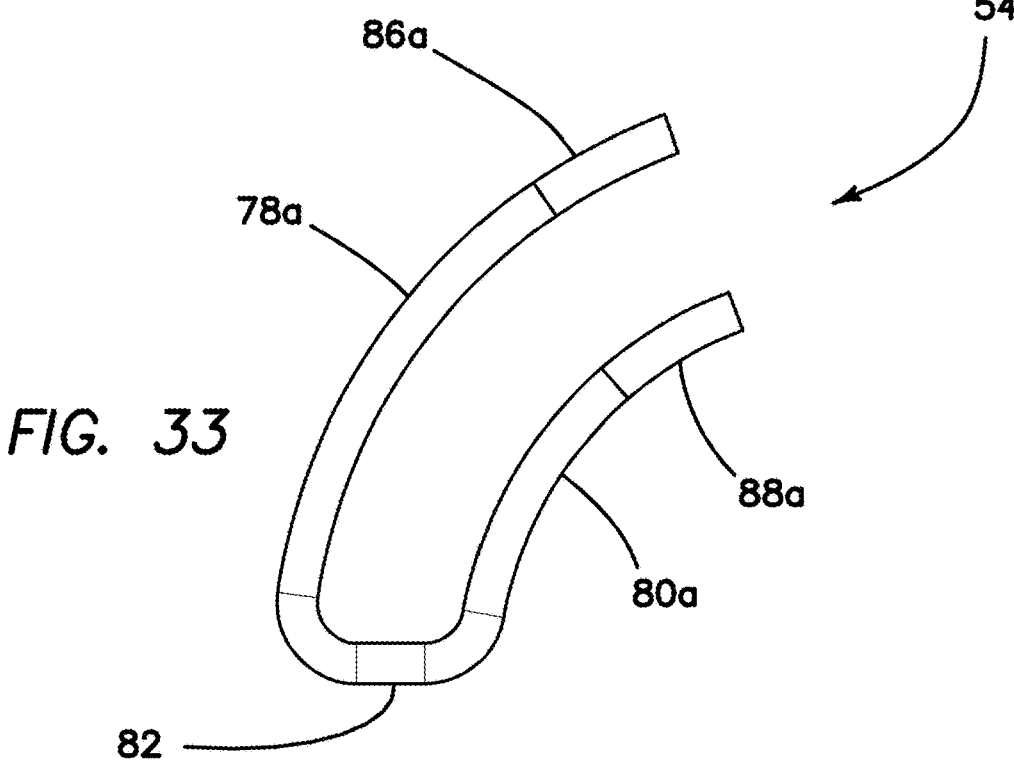
FIG. 33 is an end view of a staple according to the present invention.
Figures 34, 35:
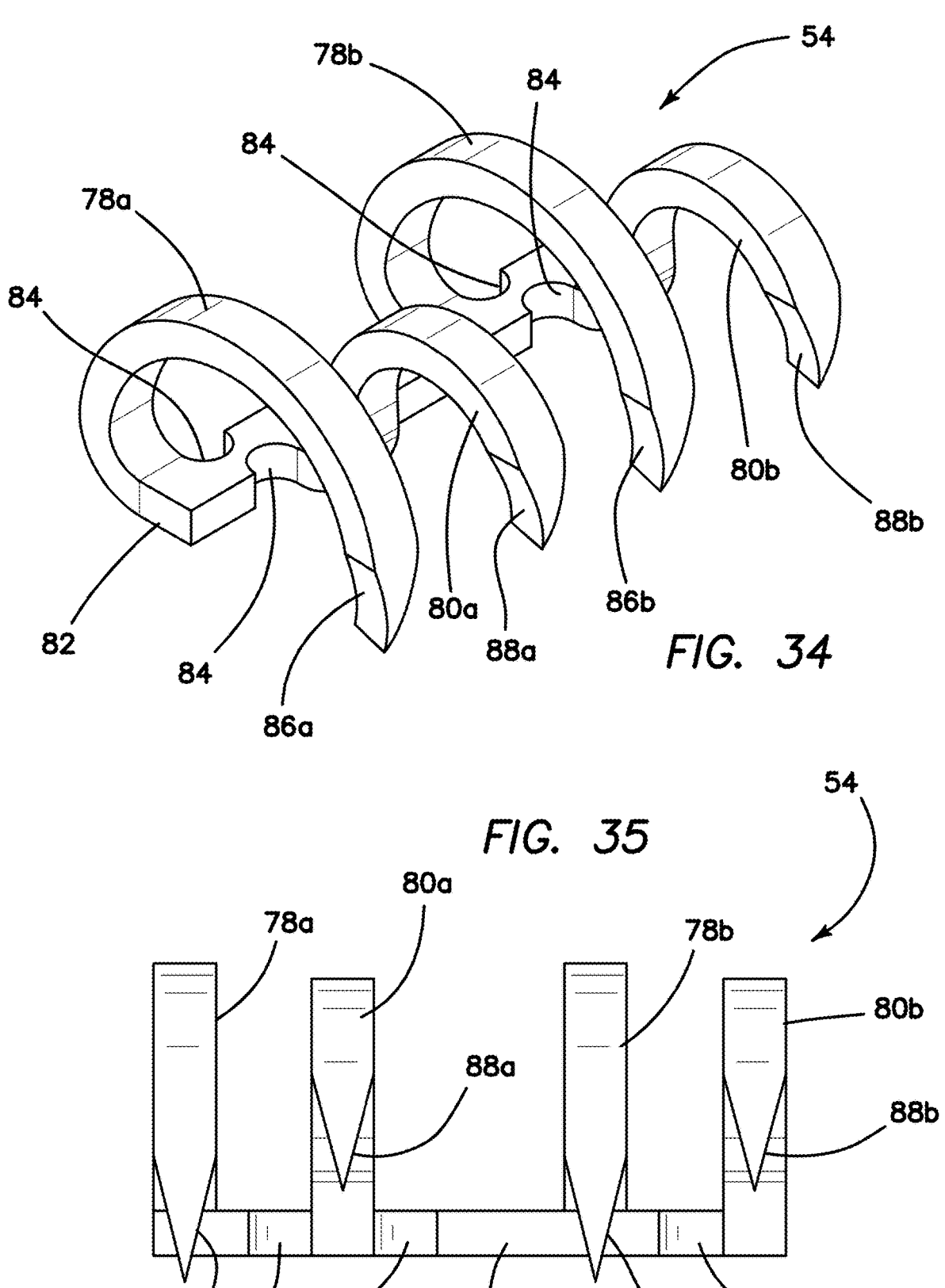
FIG. 34 is a top perspective view of a deformed staple according to the present invention.
FIG. 35 is a side view of a deformed staple according to the present invention.
Figures 36, 37:
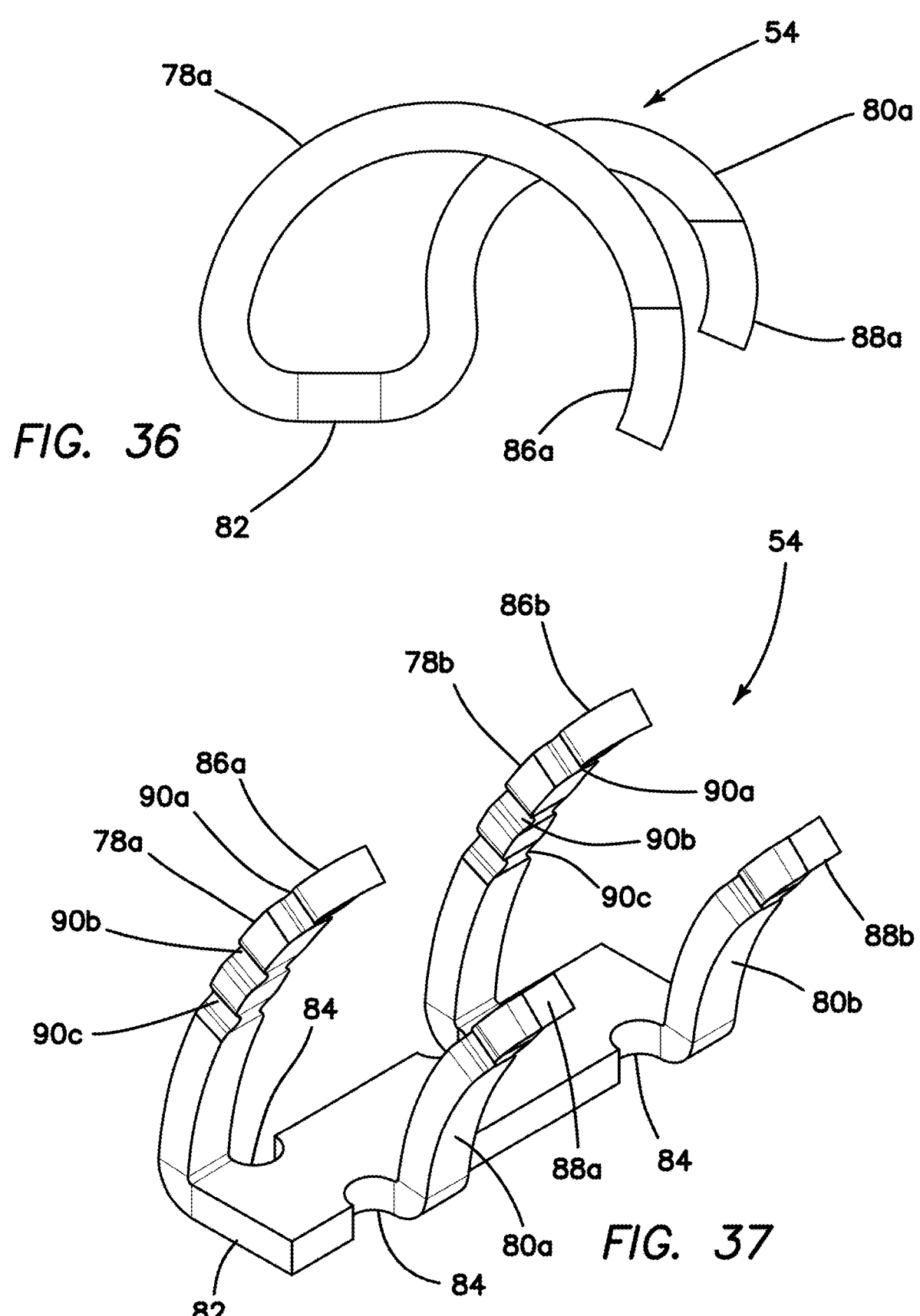
FIG. 36 is an end view of a deformed staple according to the present invention.
FIG. 37 is a top perspective view of a staple according to the present invention.
Figures 38, 39:
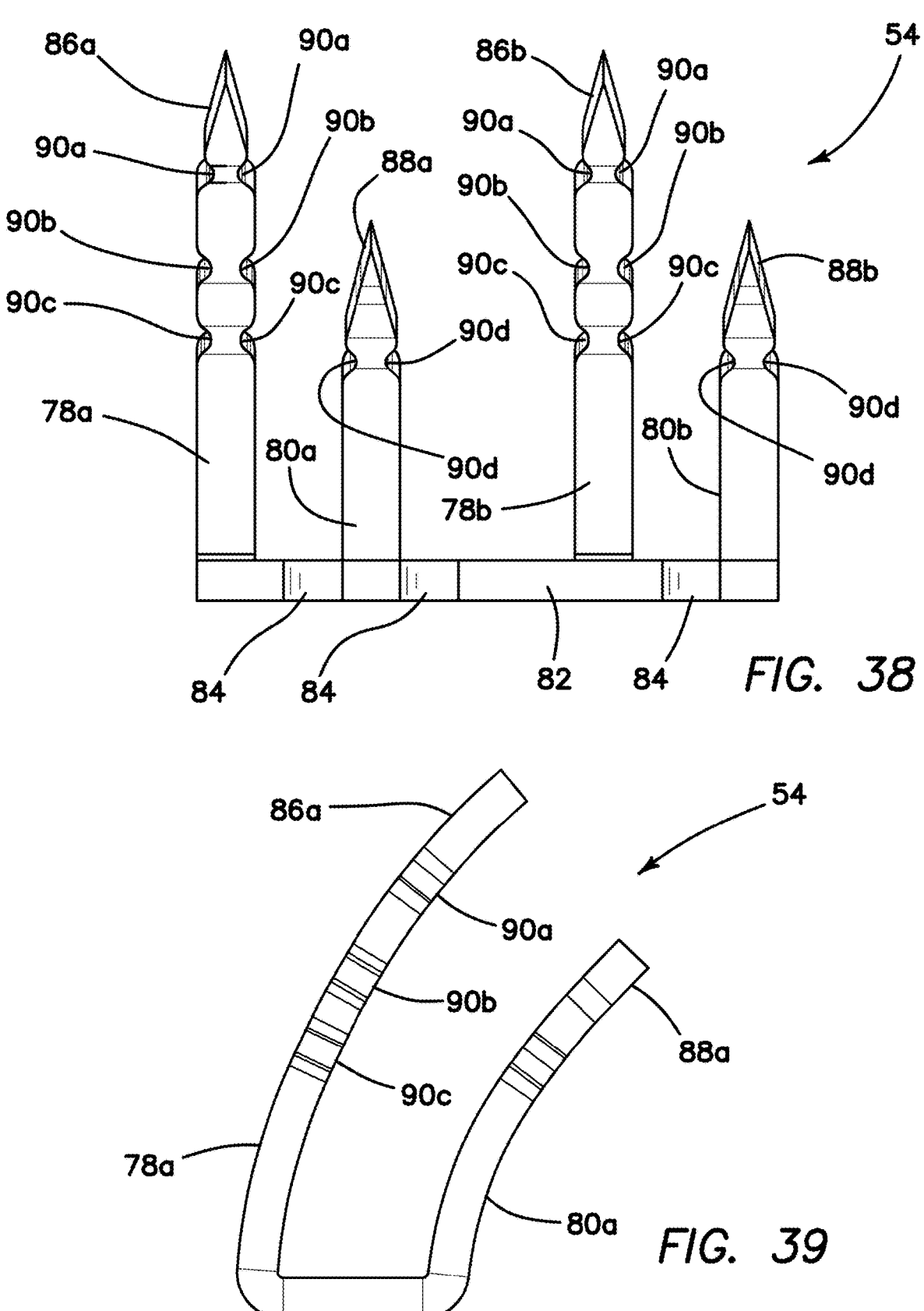
FIG. 38 is a side view of a staple according to the present invention.
FIG. 39 is an end view of a staple according to the present invention.
Figures 40, 41:
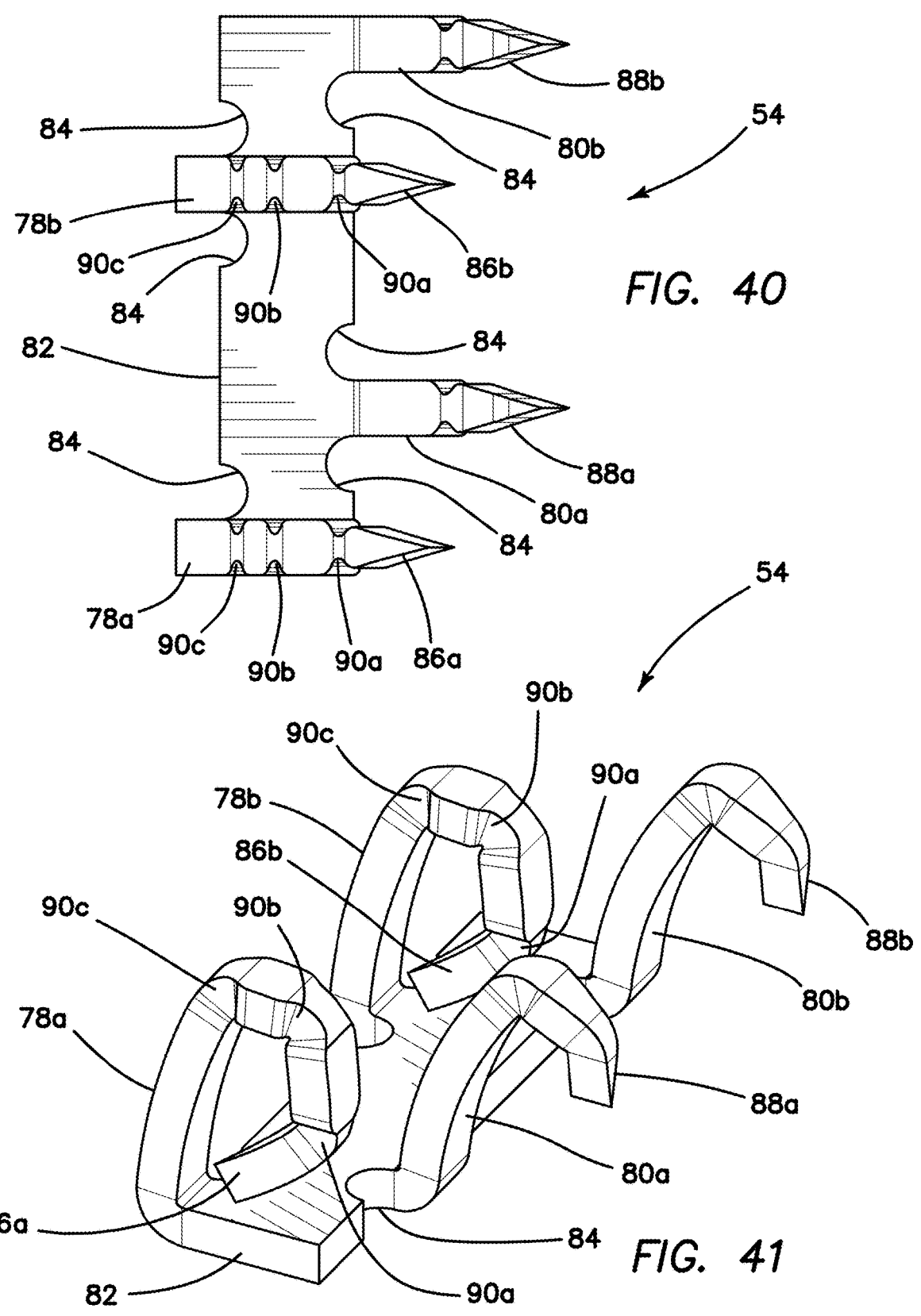
FIG. 40 is a top view of a staple according to the present invention.
FIG. 41 is a top perspective view of a deformed staple according to the present invention.

A four-pronged staple 54 having a narrower base 82 is shown in an undeformed or open configuration in FIGS. 31-33 where like reference numbers are used to describe like parts. In this variation of the staple 54, the base 82 is approximately 0.020 inches wide and approximately 0.100 inches in length. The lateral distance between the inner surface of longer legs 78A, 78B and the inner surface of the shorter legs 80A, 80B is substantially the same as the staple 54 shown in FIGS. 24-30. Therefore, it will fit inside the same sized channel 53 and the base 82 is configured to cam against the pusher 58. The staple 54 of FIGS. 31-33 has an inside bend radius at the legs 78A, 78B, 80A, 80B that substantially matches the thickness of the base 82. The legs 78A, 78B, 80A, 80B are curved in the same manner. FIGS. 34-36 show the staple 54 in a second or deformed configuration after complete actuation of the stapler. Deployment of the four-pronged staple 54 results in the shorter legs 80A, 80B contacting the anvil surface 74 and being deformed. The shorter legs 80A, 80B are deflected vertically downwardly toward the base 82 and laterally away from the base 82, away from the longitudinal axis of the staple 54. The shorter legs 80A, 80B bend to form a curl having a C-shape with the tips 88A, 88B pointing substantially downwardly. The longer legs 78A, 78B will contact the anvil surface 74 and with continued movement of the slider 32 will deform such that the longer legs 78A, 78B are deflected vertically downwardly toward the base 82 and laterally toward the longitudinal axis of the base 82. The longer legs 78A, 78B bend to form a larger deeper curl relative to the deformed shorter legs 80A, 80B. Also, the tips 86A, 86B of the longer legs 78A, 78B are vertically closer to the base 82 than the tips 88A, 88B of the shorter legs 80A, 80B. The longer legs 78A, 78B have a larger radius of curvature relative to the shorter legs 80A, 80B. All of the legs 78A, 78B, 80A, 80B are deflected in the same direction. For example, all of the legs 78A, 78B, 80A, 80B are deflected to the right side or to the right of the staple longitudinal axis when viewed from the end in FIG. 36. Because of the narrower base 82, the tips 86A, 86B, 88A, 88B are resident to the right of the base 82 and are not located above the base 82. Pockets in the anvil surface 74 that are aligned with the exit opening in the top surface of the lower jaw, guide and aid in the proper deformation of a staple.

Figure 42:
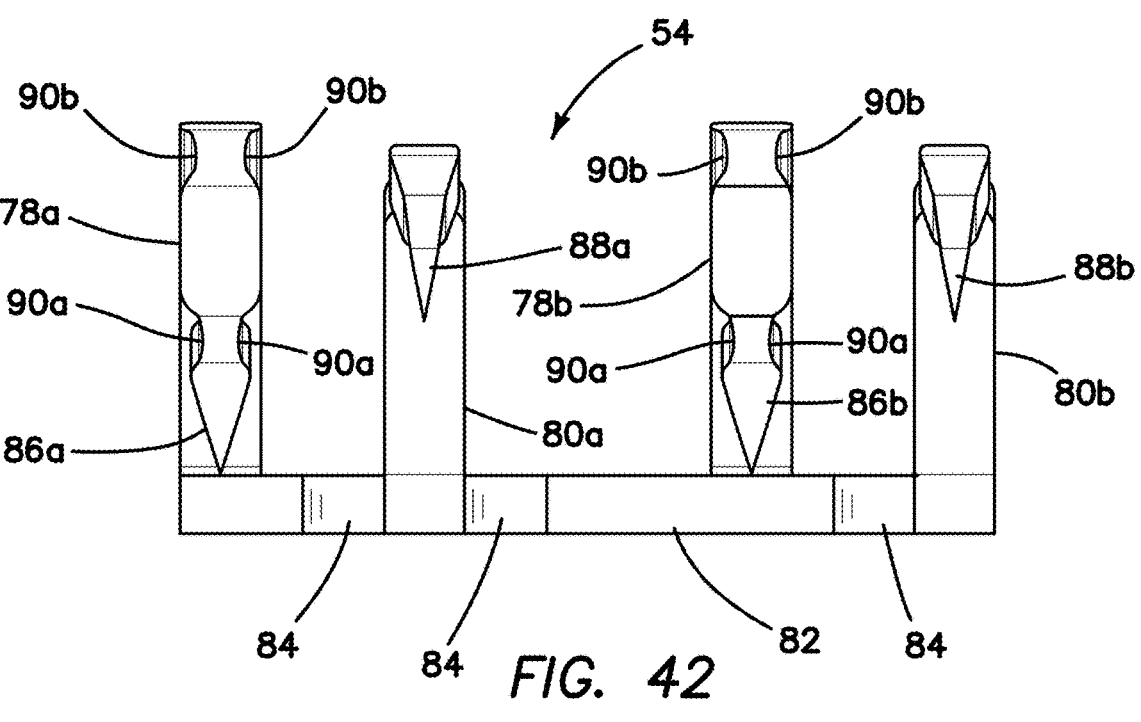
FIG. 42 is a side view of a deformed staple according to the present invention.
Figure 43:
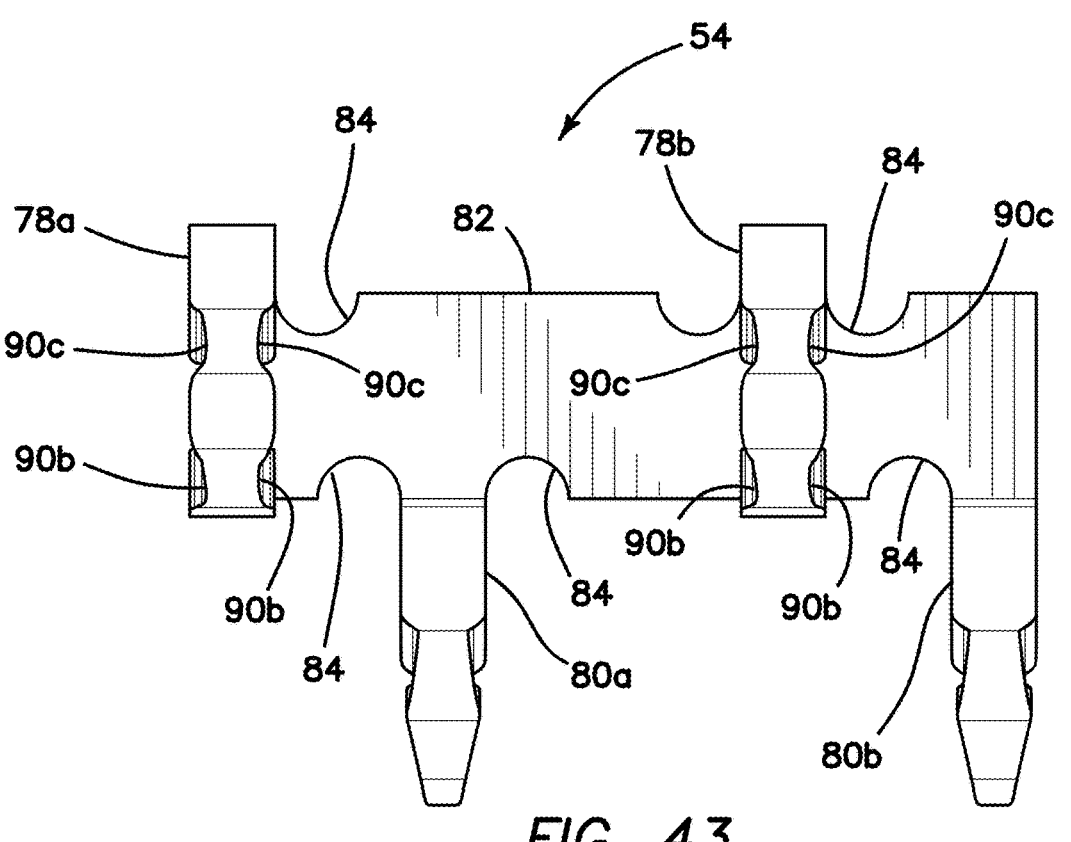
FIG. 43 is a top view of a deformed staple according to the present invention.

Turning now to FIGS. 37-40, another staple 54 according to the present invention will be described using like reference numbers to describe like parts. The staple 54 is a four-pronged staple 54 shown in its undeformed or open configuration and is substantially similar to the staple 54 of FIGS. 24-30. The four-pronged staple 54 includes two longer first legs 78A, 78B and two shorter second legs 80A, 80B interconnected by a base 82. The two longer legs 78A, 78B are staggered with respect to the two shorter second legs 80A, 80B. Each of the legs 78A, 78B, 80A, 80B has their respective tip 86A, 86B, 88A, 88B. The staple 54 of FIGS. 37-40, further includes a plurality of leg notches 90 formed in the legs 78A, 78B, 80A, 80B. The leg notches 90 extend inwardly from the side surfaces of the legs to create stress concentrations such that when deflected against the anvil surface 74, the legs will tend to bend in the location of the leg notches 90. Along the length of a leg, at least one pair of leg notches 90 is formed wherein each leg notch 90 of the pair is located opposite from each other and at the same height with respect to the base 82. The longer legs 78A, 78B are shown to have three pairs of leg notches 90A, 90B and 90C. The first pair of leg notches 90A is located just beneath the tip 86A and two other pairs of leg notches 90B, 90C are located further down along each leg 78A, 78B. The shorter second legs 80A, 80B are each formed with a single pair of leg notches 90D located just below the tip 88. The leg notches 90 are configured such that deployment of the staple 54 against the anvil surface 74 forms a predetermined deformed configuration as depicted in FIGS. 41-43. The legs are shown bent in the location of the notches 90 to form segmented C-shaped curls wherein portions of the leg between the leg notches 90 define segments of the deformed configuration. In the deformed configuration, all of the legs 78A, 78B, 80A, 80B are bent in the same direction with the shorter legs 80A, 80B being deflected laterally away from longitudinal axis of the staple 54 and the longer legs 78A, 78B being deflected toward the longitudinal axis with the tips 86A, 86B, 88A, 88B being deflected vertically downwardly into tissue. The segmented deflection along the leg notches 90 helps in angulating the sharp tips into penetrating tissue as well as in creating a deformed staple height that can accommodate tissue inside the staple 54 without severing the tissue arising from uneven deformation. The leg notches 90 provide a C-shaped curvature in the legs that is consistently and reliably formed.

In any of the staple variations, the staple legs 78A, 78B, 80A, 80B may include at least one barb or lateral hook-like protrusion. The at least one barb may be provided anywhere along the length of the leg including near the distal end of each leg and formed in side surfaces. Barbs assist in providing an increased mechanical hold of the staple into tissue and can be formed on any or all of the four legs and on the inner surface, outer surface and/or side surfaces. In one variation, at least one barb is formed in the inner surface of the longer first legs 78A, 78B and the outer surface of the shorter second legs 80A, 80B. Multiple barbs along one or more of the legs are also possible as are smaller barbs such as micro and nano-sized barbs.

The staples 54 may be formed attached to a backbone in a fishbone style for ease of manufacturing, assembly and handling. A sheet or block of metal such as surgical steel, stainless steel, or titanium is provided and a plurality of staples 54 is cut into the sheet of metal on a wire electrical discharge machining (EDM) machine. The staples 54 may also be formed utilizing a micro-water jet, photo etching or by stamping. The staples 54 may be formed with bent legs or the bending of the legs is performed in a separate step. The staples 54 remain connected to the backbone via narrow connecting tabs until the staples 54 are broken off at the tabs and then loaded into a staple cartridge. After a staple 54 is broken off, a portion of the connecting tab may remain attached to the staple 54. The remnant tab may advantageously serve as a barb for increasing mechanical holding onto tissue captured inside a closed staple 54 after deployment. Also, the backbone can be an aid in the storage of staples 54 and in the assembly of staple cartridges.

A staple cartridge in the form of a single unit is inserted into a staple cartridge receiving portion of the lower jaw 50. The staple cartridge may also be in the form of two units with each unit having two slots to be loaded on either side of the central lower jaw channel 55. Each cartridge can include a cover slip of paper (not shown) covering the staple channels 53 to retain the staples 54 during storage and handling. The cover slip is then removed by peeling away just prior to or after installation of the cartridge. Each staple cartridge may also contain an I-beam 32 and pushers 58 disposed inside the cartridge. In another variation of the cartridge, the staple cartridge is pre-installed inside the stapler cartridge assembly 14 and after the staples 54 are expended the entire stapler cartridge assembly 14 is removed and disposed and a new stapler cartridge assembly 14 is connected to the handle assembly 12 for continue stapling. With the staple cartridge assembly 14 connected to the handle assembly 12, the actuator shaft 22 connects to an actuator shaft inside the handle assembly 12. The handle assembly 12 is then used to operate the stapler 10 in three different functions or modes of operation. The first mode allows the user to open and close the jaws 48, 50 of the end effector 18. The second mode fires the staples and the third mode of operation returns the I-beam 32 to its original proximal position following the firing of staples. A lock-out mechanism locks the I-beam 32 preventing it from moving forward inside an already expended or partially expended cartridge.

The handle assembly 12 includes a handle connected to a forward driver which engages a forward tooth on the actuator shaft 22. When the handle is depressed, the actuator is moved slightly forward which in turn moves the actuator shaft 22 of the stapler cartridge assembly 14 forward. Since the actuator shaft 22 is connected to the I-beam 32, the I-beam 32 advances forward with the depression of the handle. As the I-beam 32 advances, the beveled front end 40 of the top portion 34 of the I-beam 32 enters the passageway or central slot 76 in the upper jaw 48 which deflects the open and spring biased upper jaw 48 downward from an open position to a closed position. The upper jaw 48 is connected to the lower jaw 50 with a pin such that the upper jaw 48 pivots with respect to the lower jaw 50. Springs are included to create a spring bias that urges the upper jaw 48 in an open position with respect to the lower jaw 50. When the handle is released the actuator shaft 22 moves proximally pulling the I-beam 32 also proximally allowing the spring bias to open the jaws as the top portion 34 of the I-beam exits the passageway 76. The user can open and close the jaws of the end effector 18 by pressing and releasing the handle 12 to position the targeted tissue between the upper and lower jaws of stapler 10. In a closed position, the distance across the gap between the upper jaw 48 and lower jaw 50 is approximately 0.030-0.060 inches.

After the jaws are closed in position at the targeted tissue location, the stapler 10 is switched to operate in fire mode by depressing a fire button on the handle assembly 12. The fire button disengages an open driver from the actuator shaft freeing it for longitudinal movement. The open driver is engaged with the teeth of the actuator shaft. The open driver disengages from the teeth of the actuator shaft with the fire button depressed. With the open driver disengaged, the trigger handle swings out and the forward driver engages with forward teeth on the actuator shaft. Depressing the handle advances the actuator shaft forward as the forward driver freely engages teeth with each squeeze of the trigger handle. The handle is squeezed multiple times to advance the I-beam 32 all the way to the distal end of the end effector 18. Actuation is described in co-pending U.S. Provisional Patent Application bearing Ser. No. 61/785,100 filed on Mar. 14, 2013 and entitled "Surgical stapler with partial pockets" and hereby incorporated by reference in its entirety.

Figure 47:
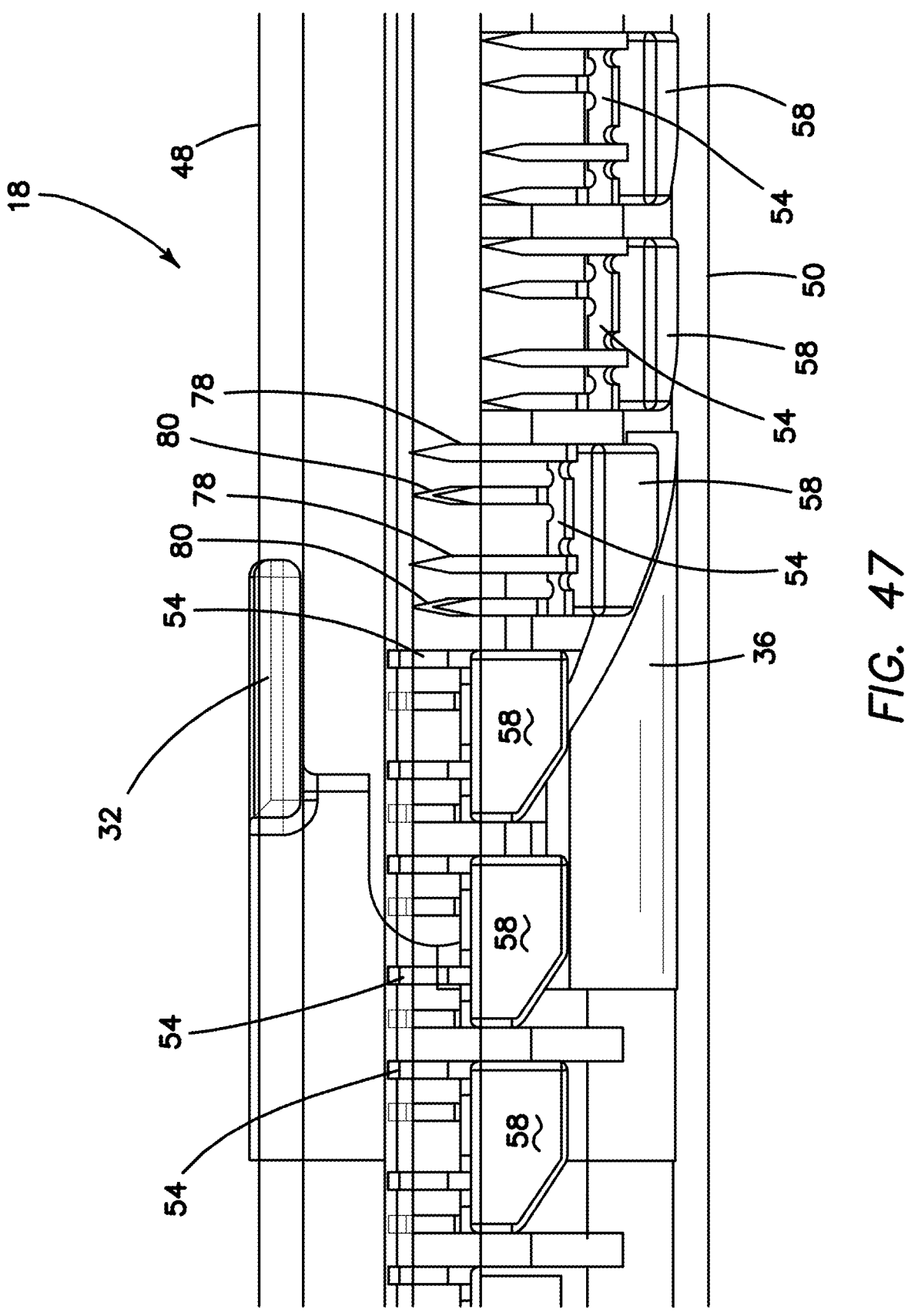
FIG. 47 is a side cross-sectional view of an end effector according to the present invention.
Figure 48:
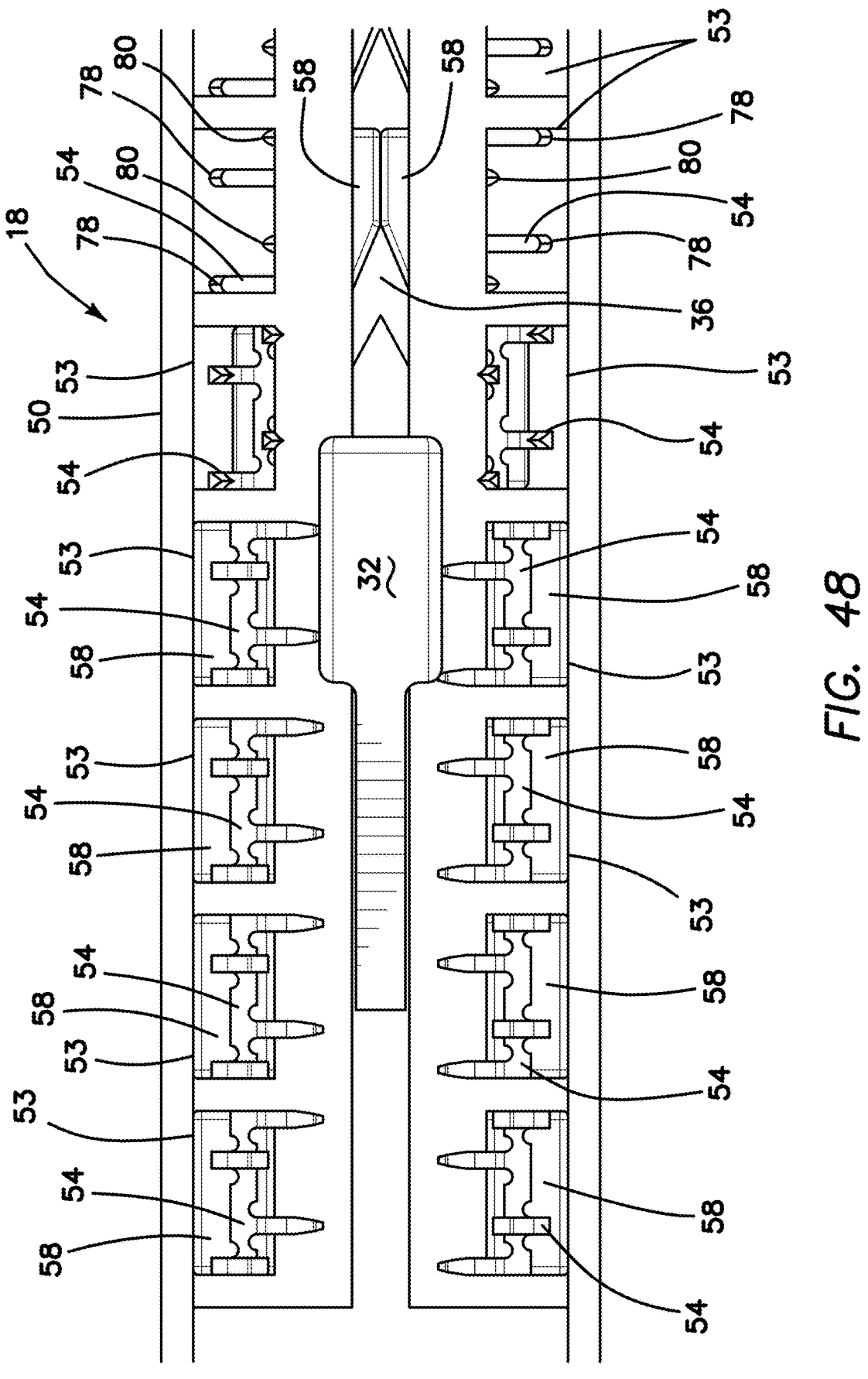
FIG. 48 is a top sectional view of an end effector according to the present invention.
Figure 49:
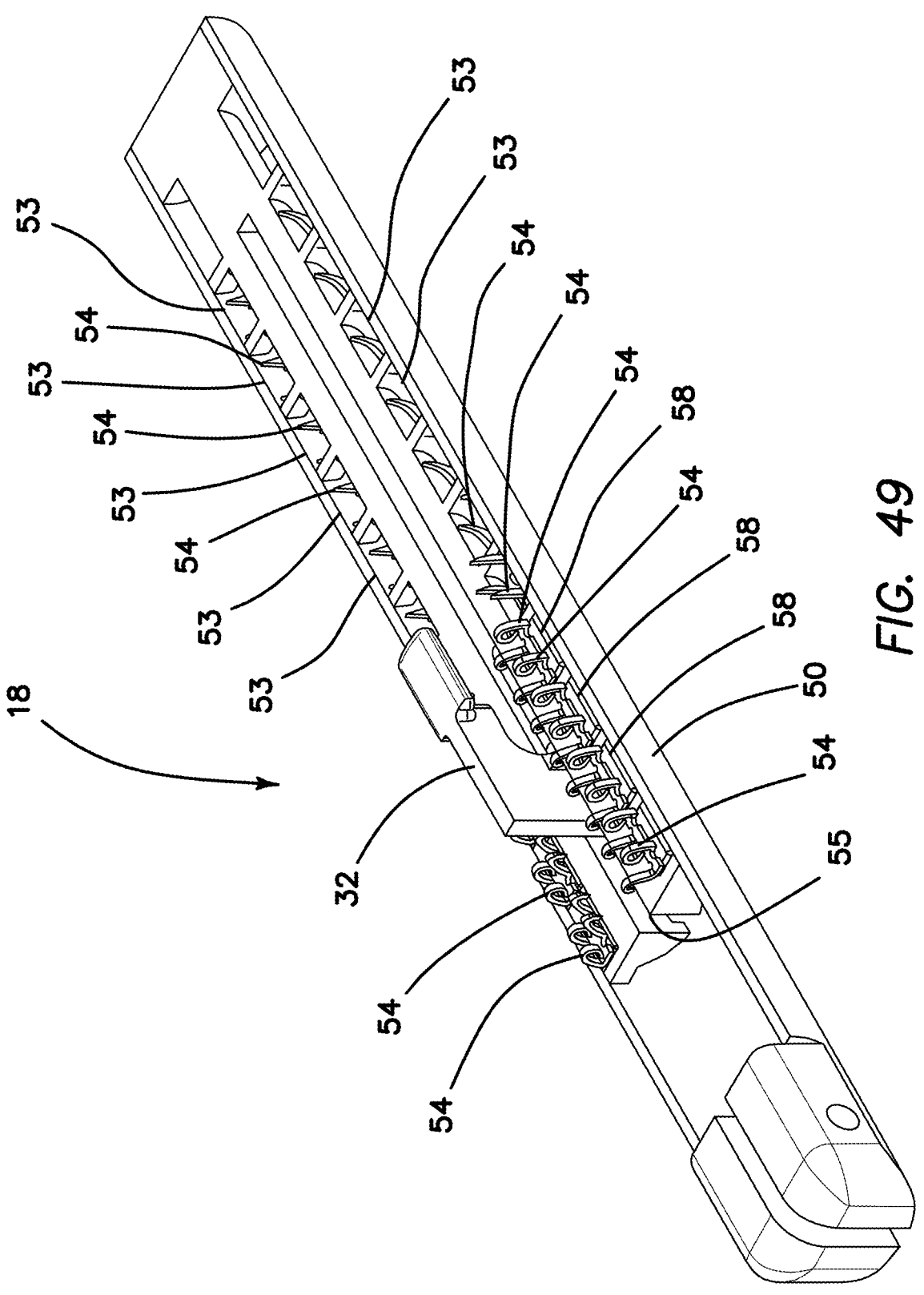
FIG. 49 is a top perspective, sectional view of an end effector according to the present invention.
Figures 50, 51, 52:
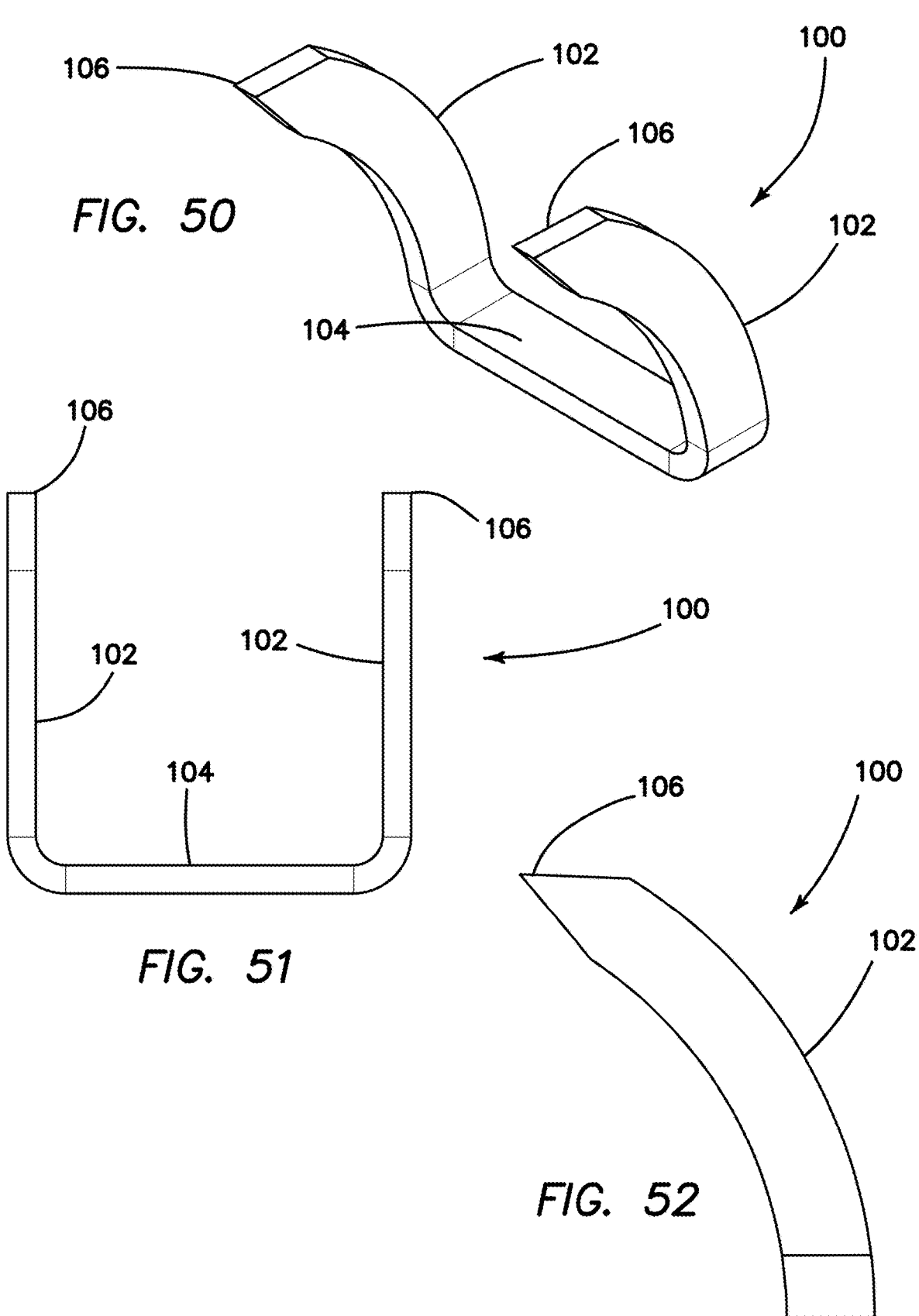
FIG. 50 is a top perspective view of a two-pronged staple according to the present invention.
FIG. 51 is a side view of a two-pronged staple according to the present invention.
FIG. 52 is an end view of a two-pronged staple according to the present invention.

FIGS. 44-46 are semi-transparent cross-sectional views of the end effector 18 with the jaws 48, 50 in a closed position taken perpendicular to the longitudinal axis in three progressive stages of staple deployment. FIG. 44 shows a pair of staples 54 residing in circumferential staple-receiving channels 53. The base 82 of each staple 54 is in contact with the top surface 60 of the pusher 58. As the I-beam 32 is advanced, the pusher 58 will move the staples 54 along the circumferential pathway, upwardly and outwardly from the lower jaw 50 and into the gap between the upper jaw 48 and lower jaw 50 as shown in FIG. 45. FIG. 45 illustrates the staple legs 78, 80, in particular, the tips of the legs 78, 80 approaching the anvil surface 74. The anvil surface 74 is shown in FIG. 45 to be provided with concave staple-forming pockets that aid in the deflection and deformation of the staple legs 78, 80 relative to the staple base 82. Since the longer staple legs 78 will first contact the anvil surface 74 before the shorter legs 80 contact the anvil surface 74, the deployment or actuation force required to bend the staple legs 78, 80 will be advantageously reduced since the longer two legs 78 of the staple 54 will have already been slightly deflected before contact with the shorter legs 80 is made and forced into deflection. The reduced firing force permits smoother deployment and increased ease of actuation. Also, circumferential firing advantageously permits the stapler to include an additional row of staples while keeping the actuation force constant. Because the staple legs 78, 80 are curved prior to deformation, the force required to deploy the staple is advantageously reduced because the curved legs do not require a greater force associated with buckling the staple legs. The curved staple legs are simply bent into the closed configuration. Further advancement of the I-beam 32 in the distal direction moves the pushers 58 on either side of the I-beam 32 together with their respective staples 54 further through the circumferential channels 53 and upwardly against the anvil surface 74 and into a deformed configuration as shown in FIG. 46. FIG. 46 illustrates a fully formed staple 54 residing in the gap between the upper jaw 48 and the lower jaw 50. The gap provides space for receiving the target tissue. FIGS. 47-48 illustrate a partially transparent side cross-sectional view and a partial cross-sectional top view of the I-beam 32 being advanced along the length of the end effector 18 with the upper and lower jaws 48, 50 in a closed configuration. FIG. 47 illustrates the various positions of the staples 54 and pushers 58 relative to the position of the I-beam 32. FIG. 49 illustrates a partial sectional, top perspective view of the end effector 18 with the I-beam 32 advanced along the central lower jaw channel 55 deploying and deforming staples 54 along the advancement pathway. The staples 54 proximal to the bottom portion 36 of the I-beam 32 are shown to be fully deformed. Staples 54 in contact with the leading surface 44 of the I-beam 32 are shown in various stages of deployment and deformation. Staples 54 distal to the leading surface 44 of the I-beam 32 are shown resident within the staple channels 53 prior to contact with the I-beam 32 and movement out of the channels 53. In this variation, the staple legs 78, 80 of a four-pronged staple are deflected in a direction that is transverse to the longitudinal axis of the end effector 18 and also transverse to the length of the staple base 82.

Referring now to FIGS. 50-53, a two-pronged staple 100 according to the present invention will be described. The two-pronged staple 100 is shown in its undeformed or open configuration. The staple 100 includes two legs 102 interconnected by a base 104. The base 104 serves as a contact surface for engagement with the pusher 58. The legs 102 extend upwardly from the base 104 and curve to one side as can be clearly seen in FIG. 52. The curvature of the staple legs 102 correspond to the curvature of the circumferential channels 53 into which they are disposed and along which they travel as they are urged by the pushers 58 coming sequentially into contact with the I-beam 32. The curvature of the staple legs 102, therefore, also substantially corresponds to the circumference of the lower jaw 50. The two side surfaces of each leg converge to form a sharp tip 106 at a line intersection at the free distal end of each leg 102. The tip 106 begins wherein the side surfaces being to taper or decrease in cross-sectional area in a direction distally along the leg 102. The tip 102 may be formed in any manner and may have any geometric shape that is suitable for puncturing and penetrating tissue through which the staple 100 is delivered.

Still referencing FIGS. 50-53, the legs 102 are approximately 0.100 inches long having a central angle of approximately 62 degrees. The overall length of the base 82 is approximately 0.100 inches and each leg 102 is concentric about the center point of a cross-section taken perpendicular to the longitudinal axis of the jaws 48, 50 in a closed orientation. The radius of curvature of the outer surface of the first longer legs 78A, 78B is approximately 0.115 inches. The distance between the side surfaces or thickness of the legs is approximately 0.007 inches. The distance between the inner surface and the outer surface or width of the legs is approximately 0.020 inches.

Figures 53, 54, 55:
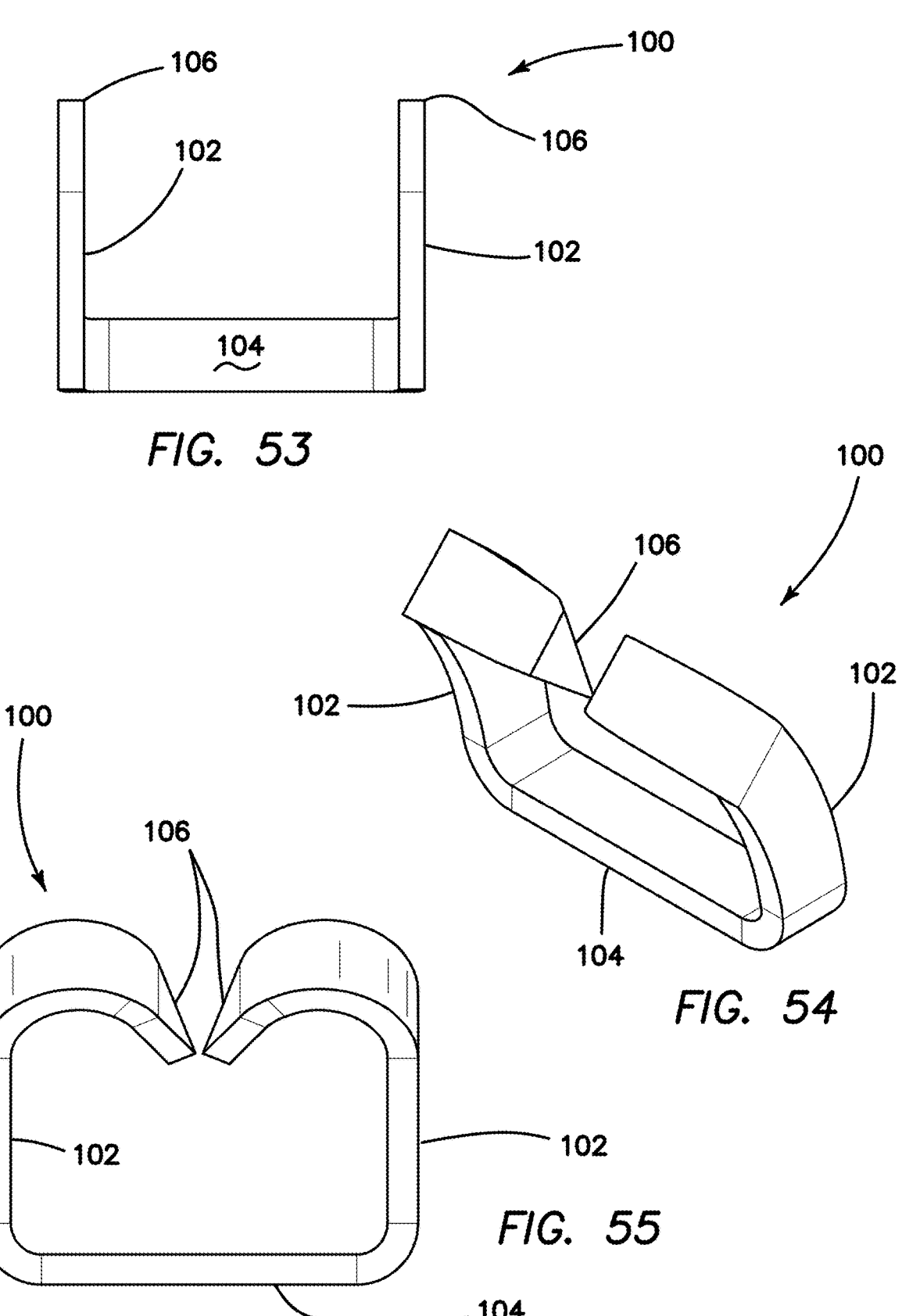
FIG. 53 is a top view of a two-pronged staple according to the present invention.
FIG. 54 is a top perspective view of a deformed two-pronged staple according to the present invention.
FIG. 55 is a side view of a deformed two-pronged staple according to the present invention.
Figures 56, 57:
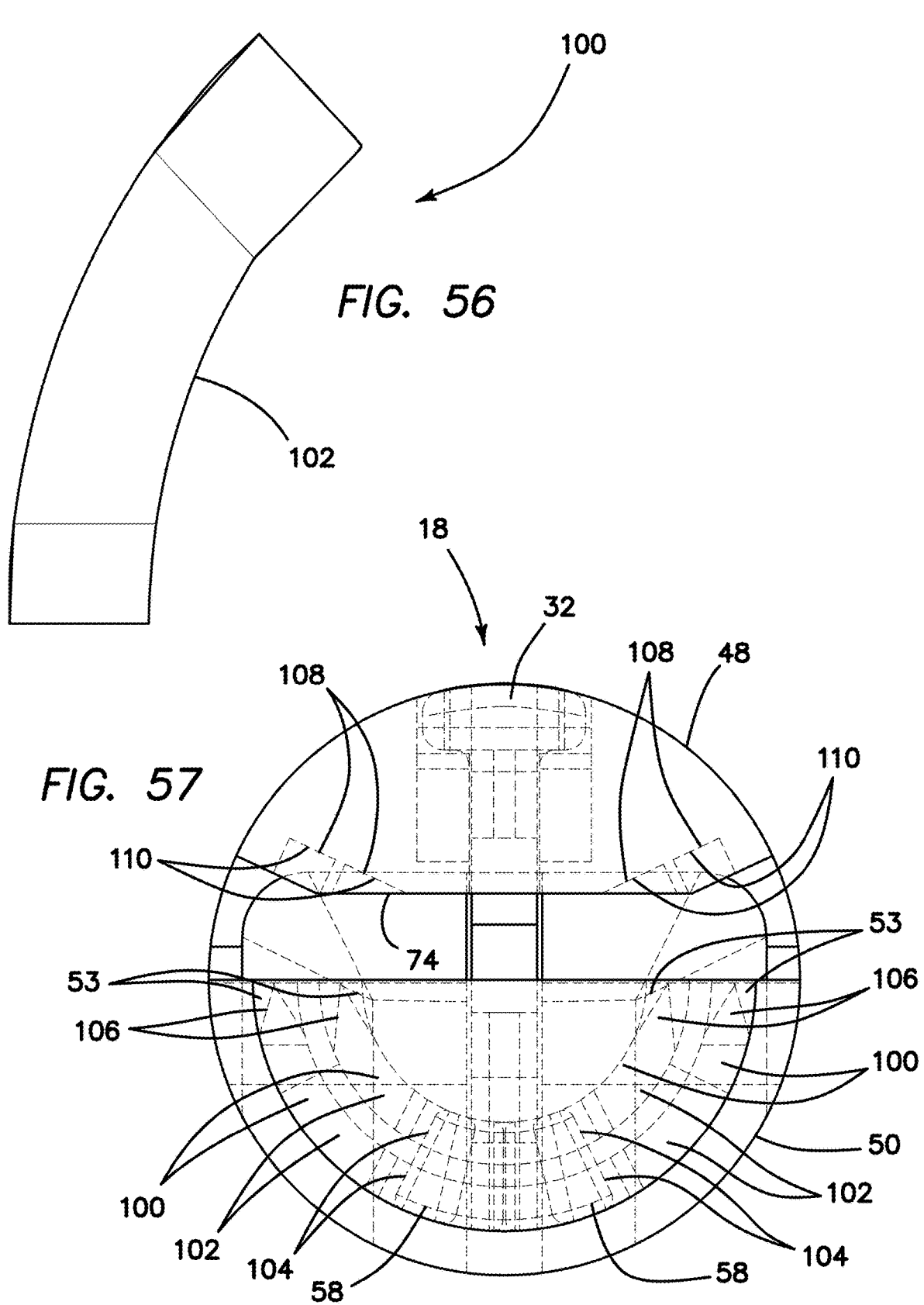
FIG. 56 is an end view of a deformed two-pronged staple according to the present invention.
FIG. 57 is a partially transparent, cross-sectional view of an end effector according to the present invention

Turning now to FIGS. 54-56, there is shown the staple 100 of FIGS. 50-53 in a second or deformed configuration after complete actuation of the stapler. Deployment of the two-pronged staple 100, which will be discussed in greater detail below, results in the legs 102 contacting the anvil surface 74 of the upper jaw 48 and being deformed. The legs 102 are deflected toward each other such that the tips 106 are angled vertically downwardly toward the base 82. The legs 102 will contact the anvil surface 74 wherein anvil pockets that are aligned with the exit openings in the top surface of the lower jaw 50 may be formed to guide the proper deformation of the staple legs 102. The deformed staple 100 has a substantially B-shaped configuration.

Figure 58:
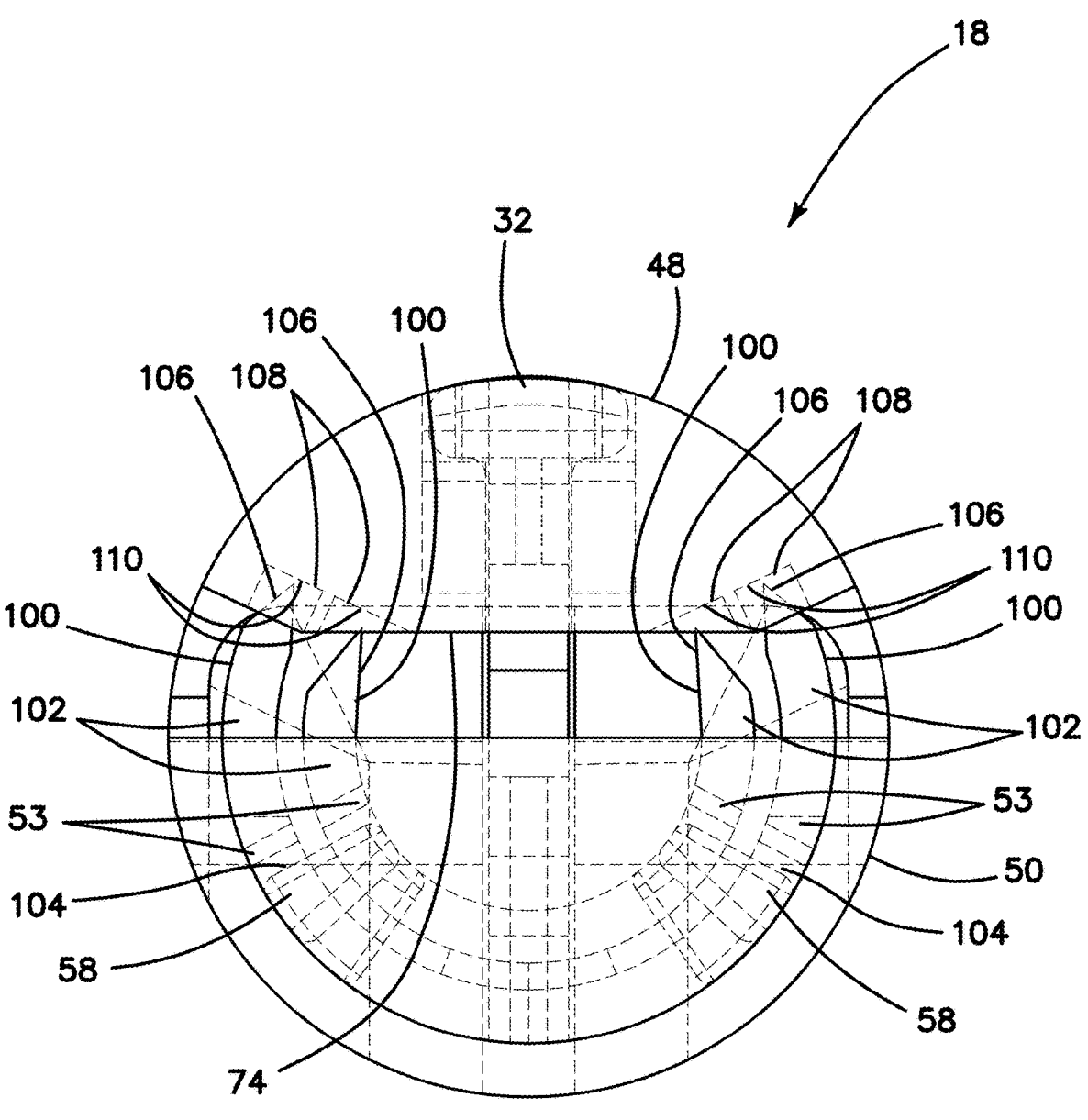
FIG. 58 is a partially transparent, cross-sectional view of an end effector according to the present invention.
Figure 59:
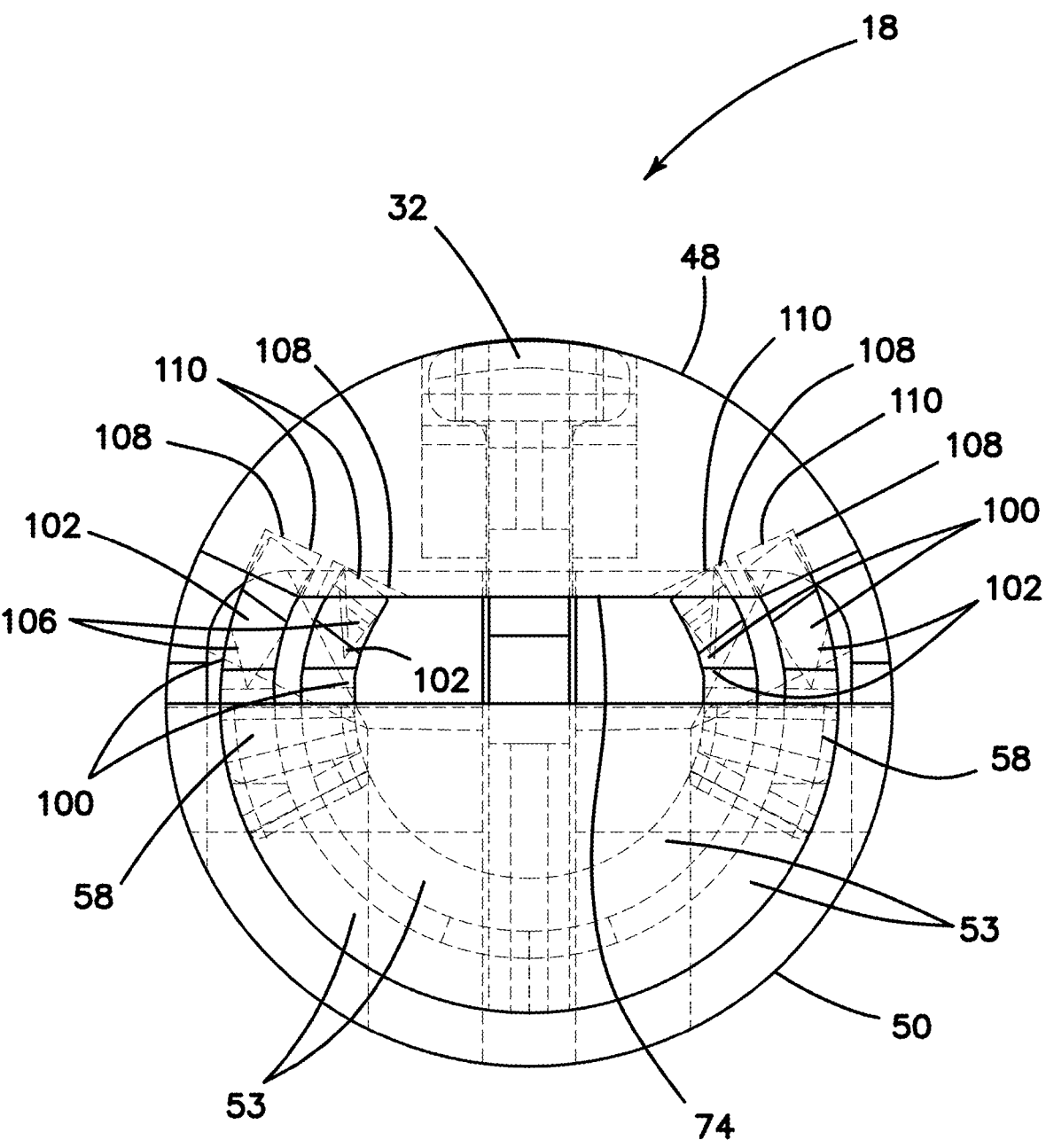
FIG. 59 is a partially transparent, cross-sectional view of an end effector according to the present invention.
Figure 60:
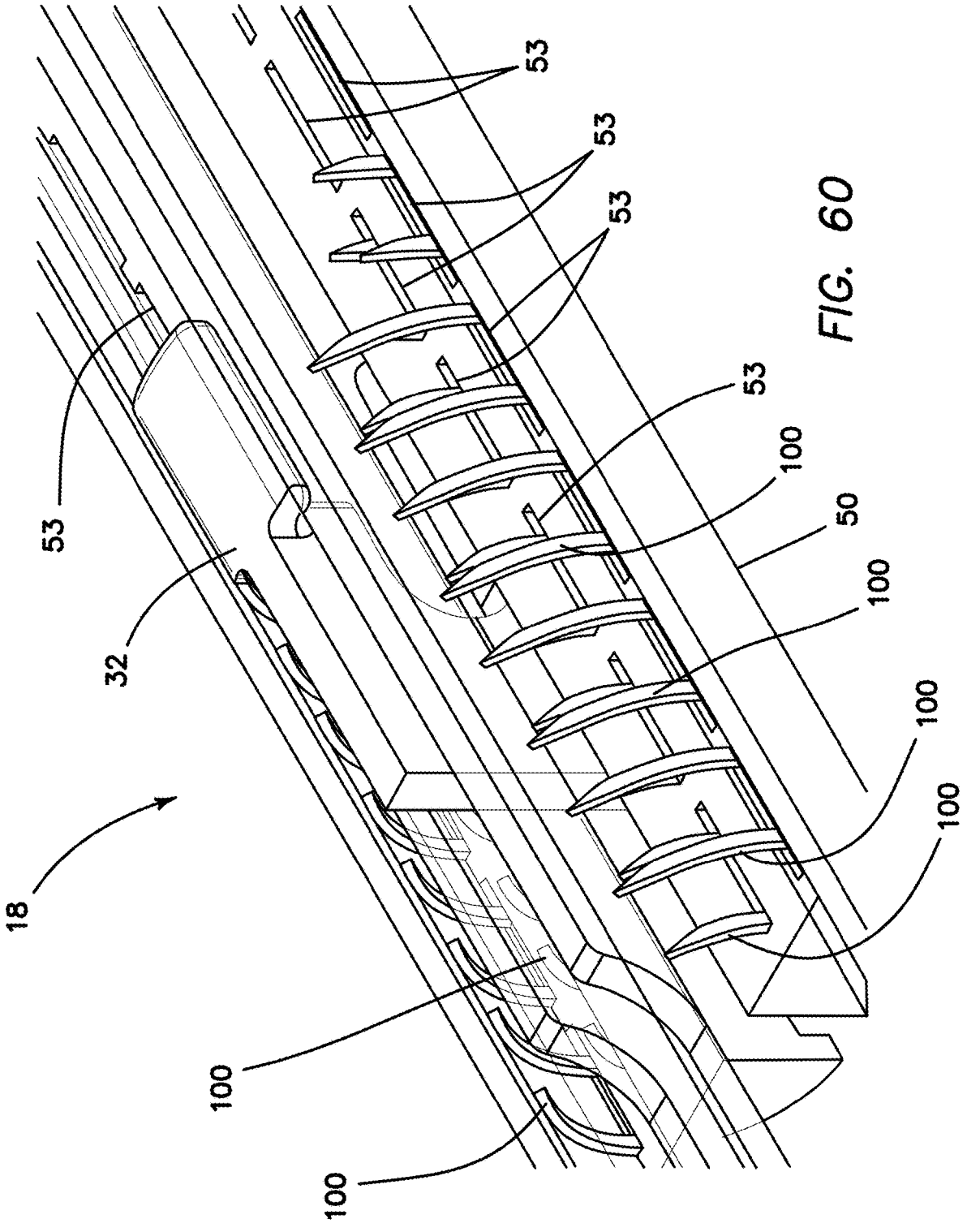
FIG. 60 is a partially transparent, sectional, top-perspective view of an end effector according to the present invention.

FIGS. 57-59 are semi-transparent cross-sectional views of the end effector 18 with the upper and lower jaws 48, 50 in a closed position taken perpendicular to the longitudinal axis in three progressive stages of staple deployment. FIG. 57 shows four two-pronged staples 100 residing in two circumferential staple-receiving channels 53 on either side of the I-beam 32. The base 104 of each staple 100 is in contact with the top surface 60 of the pusher 58. As the I-beam 32 is advanced, the pusher 58 will move the staples 100 along the circumferential pathway, upwardly and outwardly from the lower jaw 50 and into the gap between the upper jaw 48 and lower jaw 50 as shown in FIG. 58. FIG. 58 illustrates the staple legs 102 in particular, the tips of the legs 106 approaching the anvil surface 74. The anvil surface 74 is shown in FIGS. 57-59 to be provided with staple-forming pockets 108 that aid in the deflection and deformation of the staple legs 102 relative to the staple base 104. Each staple pocket 108 includes a staple contact surface 110 that is substantially perpendicular to the circumference of the staple channels 53 such that a curved staple 100 that exits a circumferential channel 53 comes into contact with the staple contact surface 110 in a perpendicular orientation. Further advancement of the I-beam 32 in the distal direction moves the pushers 58 on either side of the I-beam 32 and their respective staples 100 further through the circumferential channels 53 and upwardly against the staple pockets 108 in the anvil surface 74 and into a deformed configuration as shown in FIG. 59. FIG. 59 illustrates a fully formed staples 100 residing in the gap between the upper jaw 48 and the lower jaw 50. The gap provides space for receiving the target tissue. FIG. 60 illustrates the end effector 18 with the I-beam 32 partially advanced along the length of the end effector 18. Two rows of two-pronged staples 100 are shown on either side of the I-beam 32 at various stages of deployment. The staples 100 are shown emerging from the staple channels 53 in the lower jaw 50. Staples 100 that are located distally of the I-beam 32 have only partially emerged or have not yet emerged from the channels 32 relative to staples 100 proximal to the I-beam 32. For clarity, the staples 100 located proximally to the I-beam 32 are shown not deformed in FIG. 60; normally these staples 100 would be deformed against the anvil surface 74 of the upper jaw 48. FIG. 60 illustrates two rows of staples 100 configured such that the length of the staple bases 104 as well as the length of the channels 53 are parallel to the longitudinal axis of the end effector 18. Similarly, the staple pockets 108 (not shown in FIG. 60) in the upper jaw 48 are oriented parallel to the longitudinal axis of the end effector 18. The exit openings of the channels 53 are parallel and are aligned with the adjacent exit openings of the adjacent row of exit openings. In another variation, the exit openings of the channels 53 in the lower jaw 50 are staggered with respect to the adjacent exit openings of the adjacent row.

Figures 61, 62:
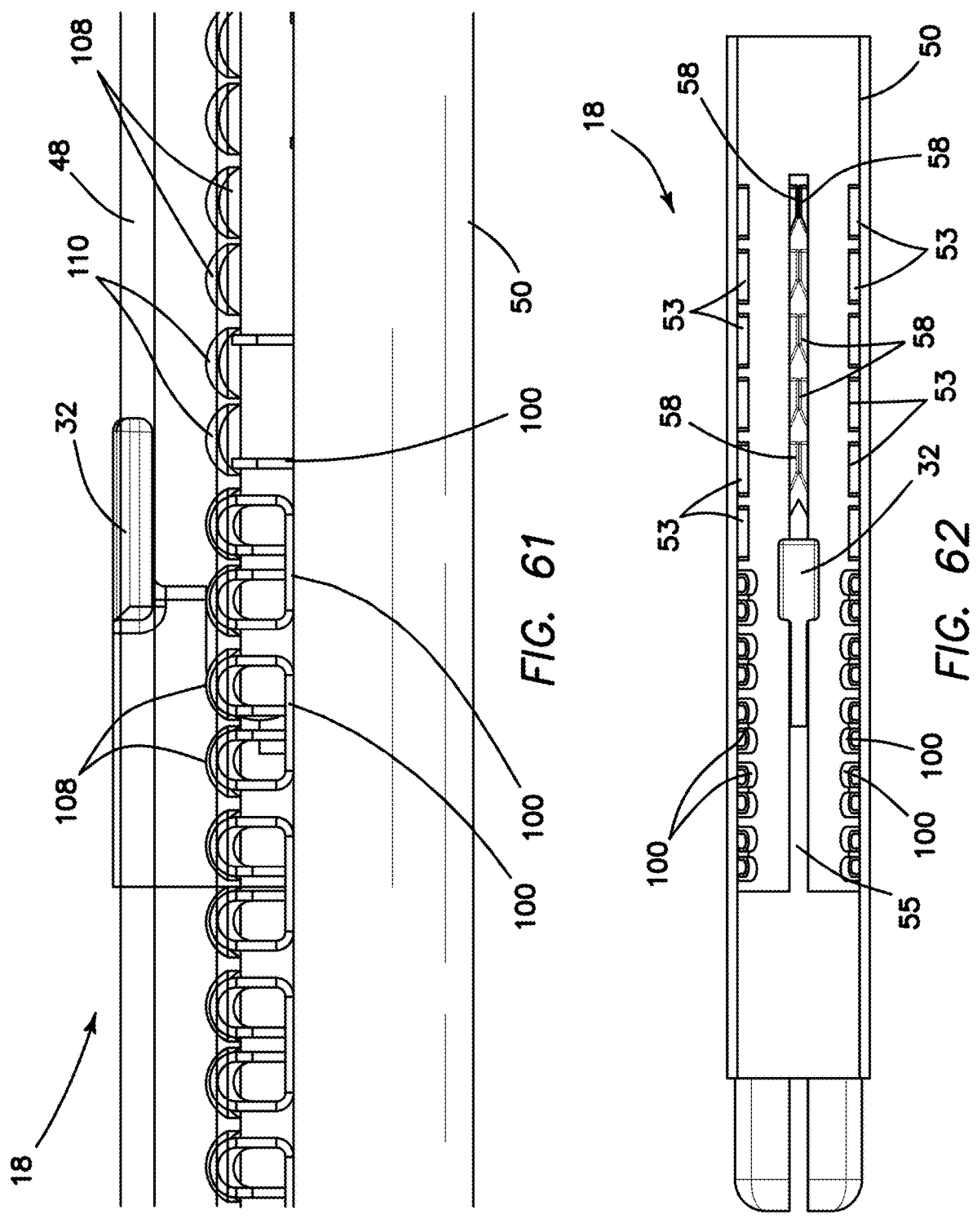
FIG. 61 is a partially transparent, side sectional view of an end effector according to the present invention.
FIG. 62 is a top sectional view of an end effector according to the present invention.
Figure 63:
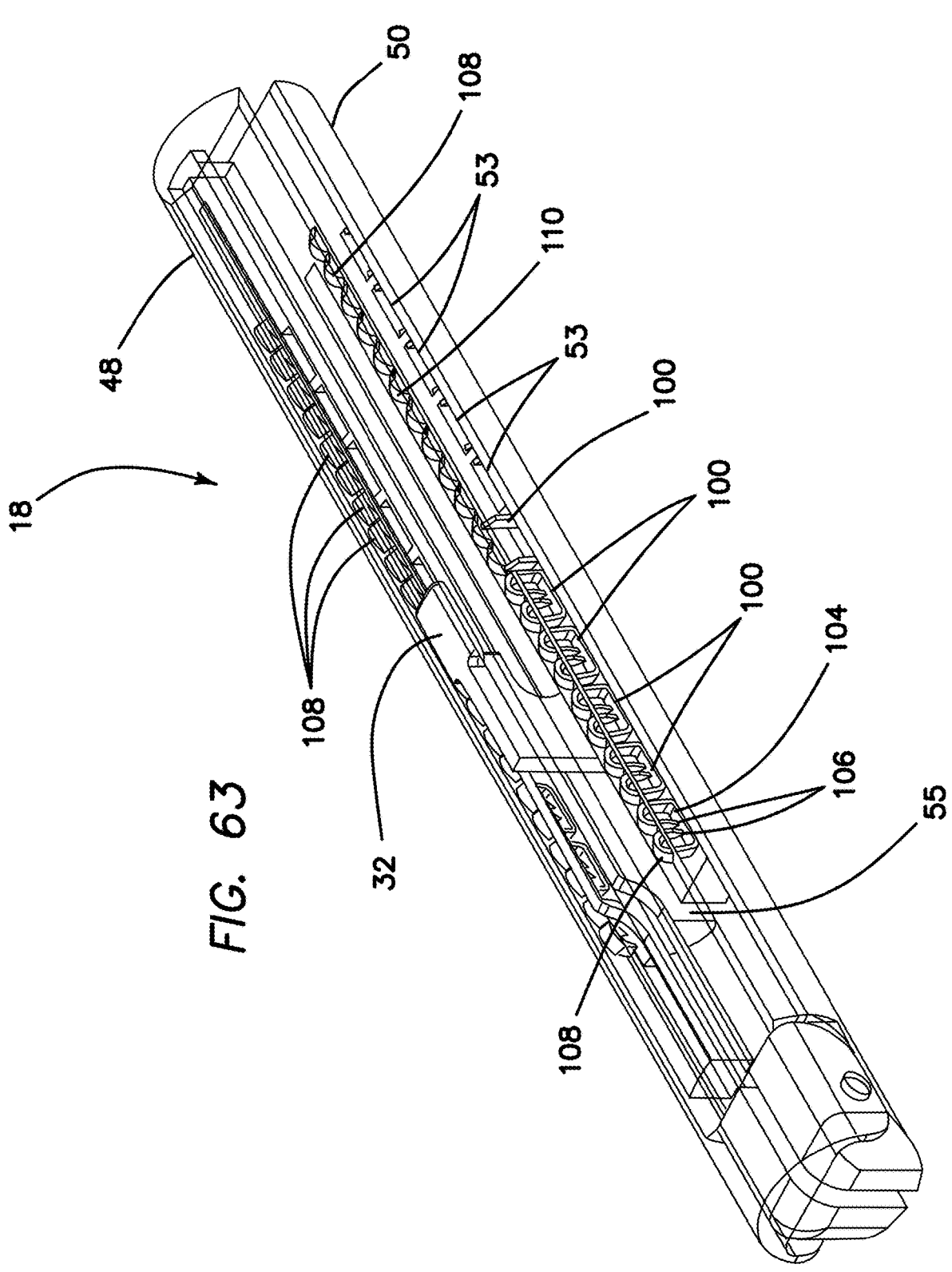
FIG. 63 is a semi-transparent, top perspective view of an end effector according to the present invention.

Turning now to FIGS. 61-63, a variation of an end effector 18 for the deployment of two-pronged staples 100 is shown in which only one row of staples 100 is provided on either side of the I-beam 32 in which the I-beam 32 is advanced along the length of the end effector 18 with the upper and lower jaws 48, 50 in a closed configuration. FIG. 61 illustrates staples 100 emerging from the lower jaw 50 relative to the translation of the I-beam 32. Deformed staples 100 are shown resident in the gap between the upper jaw 48 and the lower jaw 50 at and proximal to the location of the I-beam 32. Undeformed staples 100 are emerging from or concealed in the lower jaw 50 at and distal to the location of the I-beam 32. FIG. 62 illustrates a partial sectional, top perspective view of the end effector 18 with the I-beam 32 advanced along the central lower jaw channel 55 deploying and deforming staples 100 along the advancement pathway. FIGS. 61 and 63 illustrate staple pockets 108 in the upper jaw 48 that are aligned with the staple channels 53 in the lower jaw 50. The staple pockets 108 include two adjacent concave surfaces aligned with each exiting staple leg 102. The concave pockets 108 deflect the staple legs 102 toward each other from an undeformed substantially U-shaped staple configuration into a deformed configuration forming a substantially B-shaped configuration with the staple tips 106 pointing downward toward the staple base 104. A single staple line is formed on either side of the lower jaw channel 55. These staple lines are parallel to the longitudinal axis of the end effector 18 and the lengths of the staple bases 104 are also arranged parallel to the longitudinal axis and I-beam channel. Additional staple lines on either side of the central channel 55 are within the scope of the present invention.

As the I-beam 32 advances distally along the end effector 18, the contacting surface 72 of the I-beam 32 will contact pushers 58 located in the channels 53 which in turn will contact staples 54, 100 that are also disposed inside staple channels 53. As the I-beam 32 advances, the pushers 58 will urge the staples 54, 100 upwardly and will continue to urge them sequentially upwardly with distal translation of the I-beam 32. With sufficient deployment height, the staple legs 78, 80, 102 will come into contact with the anvil surface 74 of the upper jaw 48. In particular, the staple legs will contact the anvil surface 74 in the location of the staple pockets 108 and with further deployment will result in the bending the staple legs into the desired closed configuration capturing tissue within the staple. The closure force of the staple 54 of the present invention is advantageously relatively low because the legs 78, 80, 102 in the four-pronged and two-pronged variations already have curved or slightly bent configurations and are simply being bent over against the anvil surface 74 as opposed to being forced to buckle against the anvil surface. Buckling forces of a beam are much greater than bending forces and conventional staples generally require the buckling of staple legs simultaneously. Conventional stapling devices require high firing forces to apply the staple lines. The staple legs are forced perpendicular to the anvil pockets forcing them to buckle. These high forces apply significant stresses to the device components and can cause fatigue for the user. Therefore, the present stapler greatly reduces forces required to deploy and deform staples. The staple forming forces of the present invention are relatively low when compared with conventional staple designs providing reduced actuation forces for the user.

As the I-beam 32 is advanced, a blade on the I-beam 32 severs tissue between the already-stapled tissue. After the staples are fired, the handle assembly 12 is switched into the third mode of operation in which the I-beam 32 is returned proximally to its starting position. A gear switch button is depressed which rotates the actuator shaft 90 degrees so that the reverse teeth on the actuator come into contact with a reverse driver. The reverse driver is connected to the handle by a series of gears. When the handle is squeezed, the reverse driver pulls the actuator and I-beam 32 back. The trigger handle is squeezed multiple times to return the I-beam 32 to its original position. The I-beam 32 is returned to its original proximal position to open the jaws. With the I-beam 32 returned and fully retracted, the spring biased upper jaw 48 opens allowing the stapled tissue to be released from the jaws. When the actuator and I-beam 32 is returned, the stapler cartridge assembly 14 can be detached from the handle assembly 12 and new stapler cartridge assembly 14 can be attached to continue stapling.

Figure 1A:
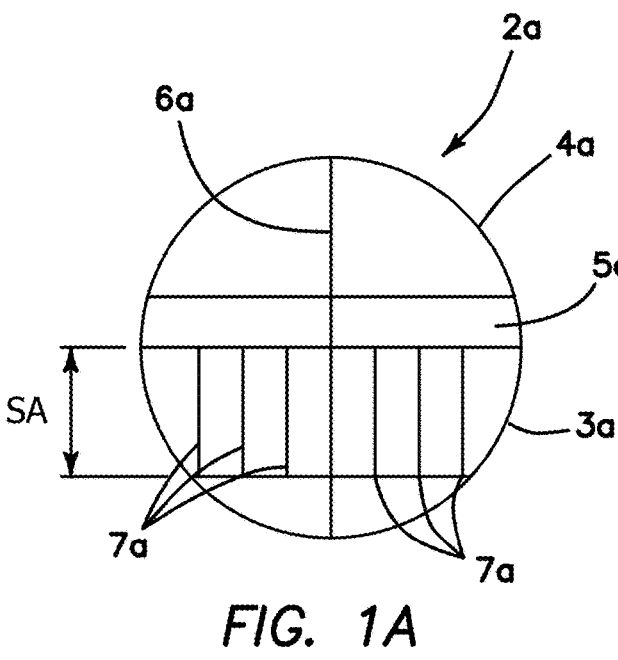
FIG. 1A is a cross-sectional schematic view of a distal end of a conventional surgical stapler.
Figure 1B:
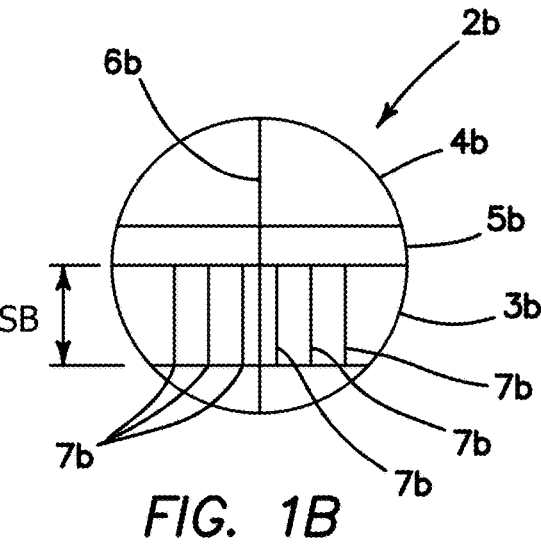
FIG. 1B is a cross-sectional schematic view of a distal end of a conventional surgical stapler with a smaller diameter.
Figure 2A:
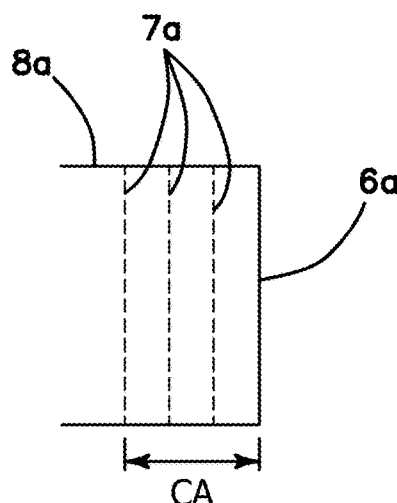
FIG. 2A is a top sectional schematic view of tissue with staples forming staple lines delivered with the stapler of FIG. 1A.
Figure 2B:
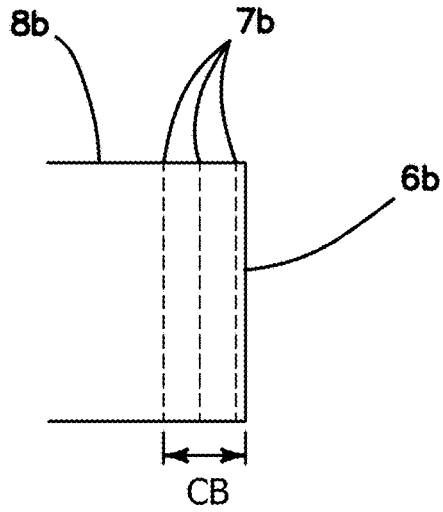
FIG. 2B is a top sectional schematic view of tissue with staples forming staple lines delivered with the stapler of FIG. 1B.
Figures 64, 65:
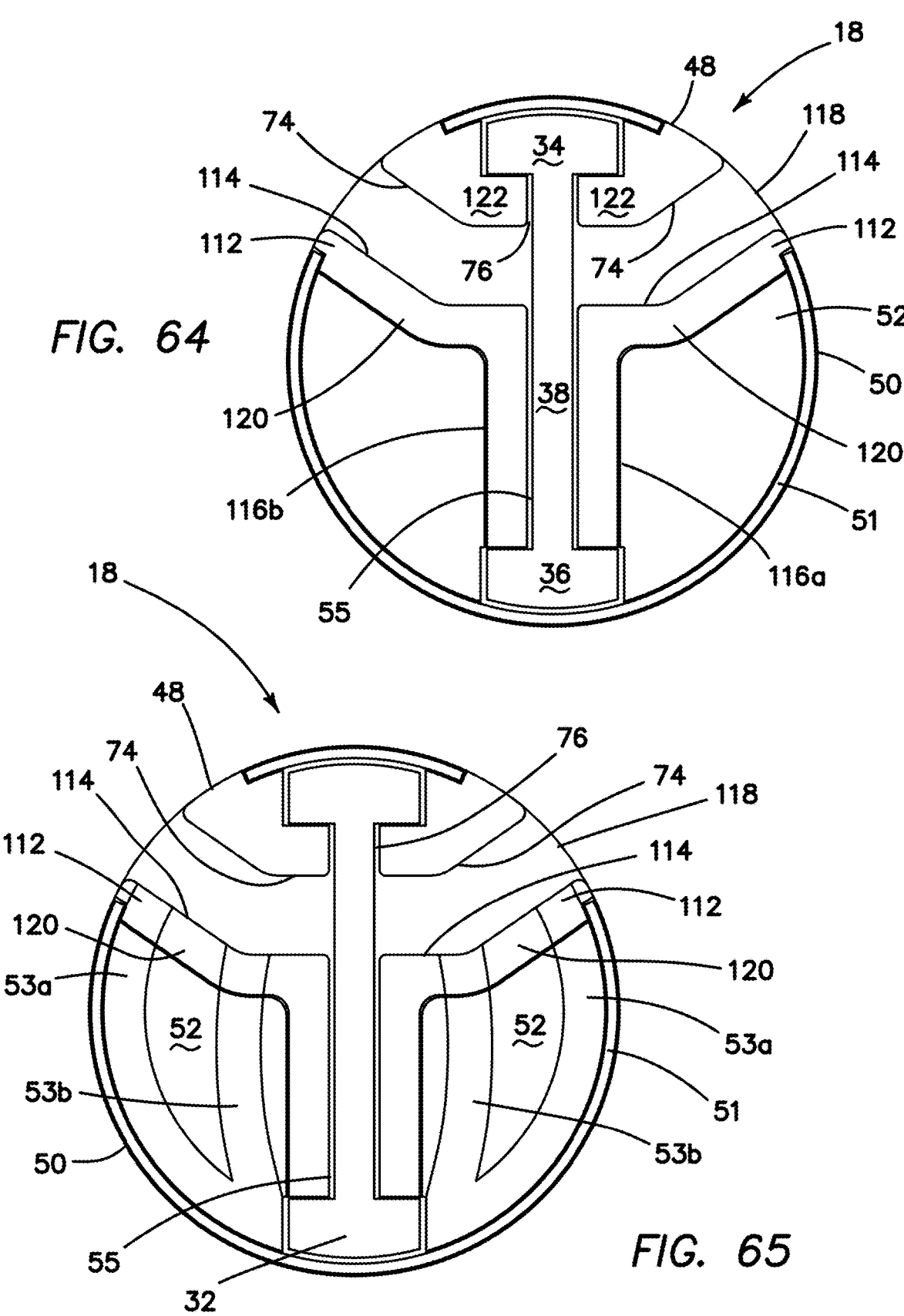
FIG. 64 is a cross-sectional view of an end effector according to the present invention.
FIG. 65 is a cross-sectional view of an end effector according to the present invention.

Turning now to FIGS. 64-65, there is shown a cross-sectional view of the end effector 18 taken perpendicular to the longitudinal axis with the I-beam 32 located in the cross-section. In the present invention, a stapler is provided that has an end effector 18 with a smaller diameter, such as in the range of 5-10 mm, without significantly changing the ability of the smaller stapler of the present invention to staple tissue having the same thickness as a relatively larger stapler, that is keeping the gap width between the upper jaw 48 and the lower jaw 50 substantially the same. This is accomplished by employing circumferential staple channels 53 in the lower jaw 50 with staples 54, 100 and pushers 58 configured to function within the circumferential channels 53. The circumferential channels 53 take advantage of the longer distance transcribed by a circumferential distance within the outer perimeter of the substantially circular cross-section of the end effector 18 relative to a shorter distance transcribed by a line represented by line 7b having a length SB shown in FIG. 1B that is perpendicular to a chord representing the upper surface of the lower jaw 48. In order to maximize the length of the circumferential line segment that is located within the outer perimeter of the circular cross-section and representative of a circumferential staple channel 53, the staple channel 53 is advantageously located as close to the outer perimeter as possible. Such placement of the outermost staple channel 53 permits the inner staple line that lies closest to the I-beam 32 to be located further away from the diametrical blade line and also allows for a longer radially-outermost staple channel 53 for receiving a staple with longer legs for the secure stapling of thicker tissues. In traditional linear staples, the lower jaw 50 comprises an outer lower jaw 51 that forms a semi-cylindrical shell of substantial thickness. Inside this shell of the outer lower jaw 51, the staples and pushers are resident. One of the functions of the outer lower jaw 51 other than forming a container for the staples is to provide structural rigidity and strength to the lower jaw so that when the staples are deployed the actuation force does not crack open, deform or bend the lower jaw itself. Therefore, the outer lower jaw 51 is typically made of strong plastic or metal of a certain thickness. This thickness of the outer lower jaw 51 is reduced in the present invention as shown in FIGS. 64-65 so that the outermost staple channel 53 can be located as close to the perimeter as possible to maximize the staple leg length that can be located therein as well as maximize the distance of the innermost staple channel away from the blade line. However, the thinner outer lower jaw 51 sacrifices lower jaw 50 strength and rigidity. This weakening is solved in the present invention by forming a frame 112 that is located inside the outer lower jaw 51 in an endoskeleton-like configuration as opposed to the exoskeleton-like configuration of traditional staplers in which the outer lower jaw 51 is made as thick as possible to provide structural rigidity to the end effector. The endoskeleton-like frame 112 of the present invention may be part of or separate from the inner lower jaw 52. The frame 112 has a thickness of approximately 0.025 inches and extends along the length of the lower jaw 50. The frame 112 is made of strong plastic or metal and forms the upper surface 114 of the lower jaw 50 from which the staple channels 53 open and from which staples exit. The frame 112 forms a substantial T-shape configuration that is divided down the midline of the "T" by the central lower jaw channel 55 in which the I-beam 32 translates. The bottom portion 36 of the I-beam 32 is substantially equal in width to the width of the vertical portion of the "T" which comprises the width of two frames 112 and the width of the central lower jaw channel 55 as can be seen in FIGS. 64-65. The bottom portion 36 of the I-beam 32 is interconnected to the top portion 34 of the I-beam 32 by a middle portion 38 of the I-beam 32. The middle portion of the I-beam 32 is substantially the same thickness as the thickness of one frame 112. The T-shaped frame 112 is formed by the juxtaposition of two L-shape elements spaced apart from each other by the central lower jaw channel 55. The horizontal portions of the L-shaped elements 116A, 116B or portions that are transverse to the I-beam 32 extend all the way to the perimeter 118. In the variation shown in FIGS. 64-65, the frame 112 has angled horizontal or transverse elements 120 which form a substantially Y-shaped frame 112. Hence, the L-shaped elements 116 form obtuse angles instead of substantially right angles common to the T-shape. The angled transverse elements 120 extend all the way to the perimeter 118 as shown in FIGS. 64-65. The transverse elements 120 include a point of inflection at which the transverse elements transition from being perpendicular to the middle portion 38 of the I-beam 32 to being angled with respect to the middle portion 38. This angulation of the frame 112 opens up more space inside the lower jaw 50, in particular, adjacent to the perimeter where longer staples legs can be accommodated. In this variation, the upper jaw 48 includes a reinforcement 122 divided by the central slot 76 in the upper jaw 48. The reinforcement 122 of the upper jaw 48 includes the anvil surface 74. The anvil surface 74 is generally angled in a manner that parallels or corresponds substantially with the angle of upper surface 114 of the lower jaw 50. The gap for capturing tissue is defined between the anvil surface 74 and the upper surface 114 of the lower jaw 50. The reinforcement 122 is made of metal or plastic.

FIG. 65 illustrates the staple channels 53 formed in the configuration of the end effector 18 of FIG. 64 having the endoskeleton-like frame 112 configuration. There are shown two staple channels 53 on either side of the I-beam 32, an outermost channel 53a and an innermost channel 53b. The outermost channel 53a closely approximates the perimeter 118 and is located adjacent to the outer lower jaw 51 having a radius of curvature that is approximately the same as the radius of curvature of the perimeter 118 of the lower jaw 50. The innermost channel 53b has a radius of curvature that is larger than the radius of curvature of the outermost channel 53a. The upper surface 114 of the lower jaw 50 and the anvil surface 74 are substantially parallel to each other such that staples exiting the channels 53a, 53b will be oriented such that the staple legs are substantially perpendicular to the anvil surface 74. The angled tansverse elements 120 of the frame 112 are advantageously angled upwardly thereby maximizing the space of the inner lower jaw 52 and length of the channels 53, in particular the length of the outermost channel 53a which accommodates the use of staples with longer legs for stapling tissue across the gap between the anvil surface 74 and upper surface 114 of the lower jaw 50.

Figure 66A:
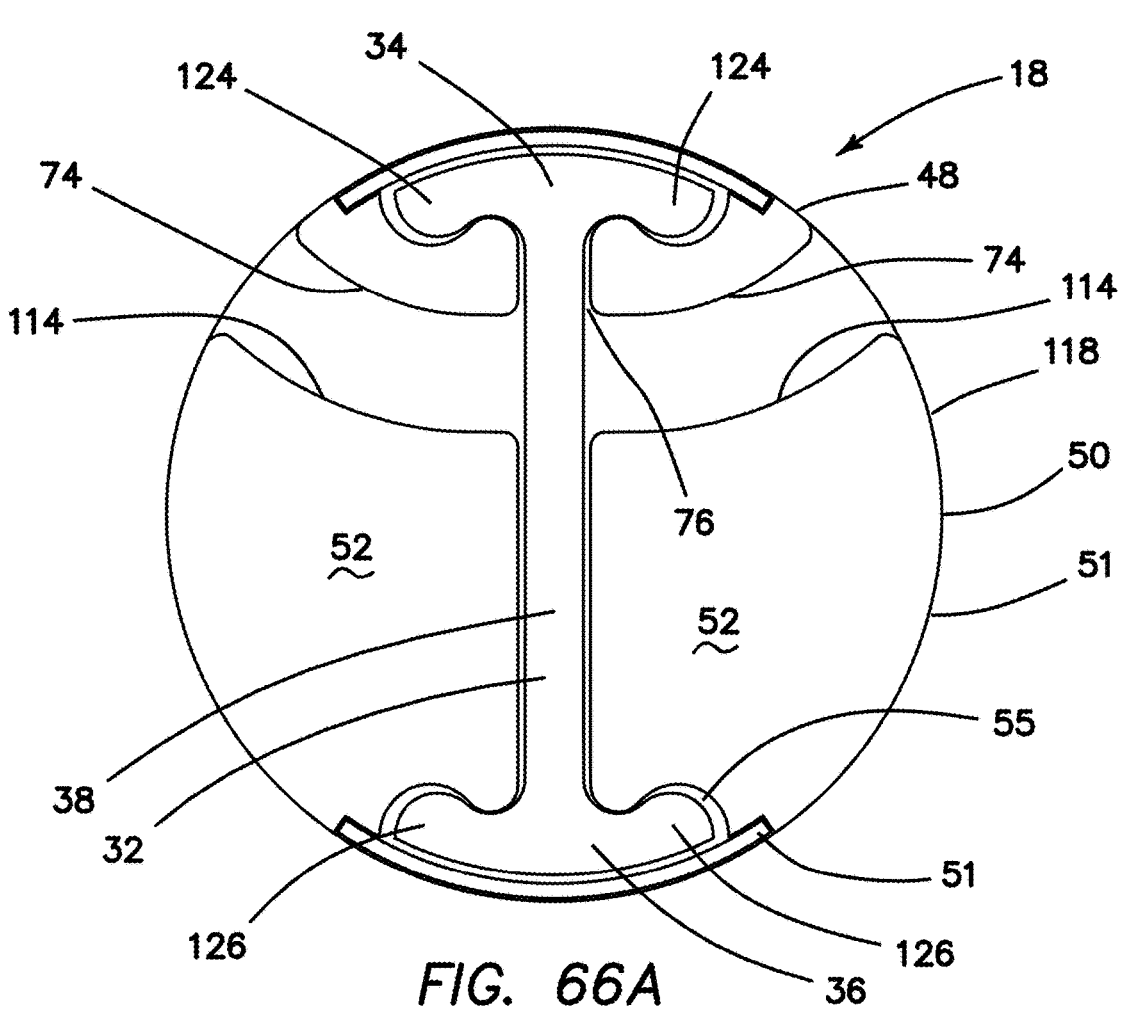
FIG. 66A is a cross-sectional end view of an end effector according to the present invention.
Figures 66B, 66C, 66D:
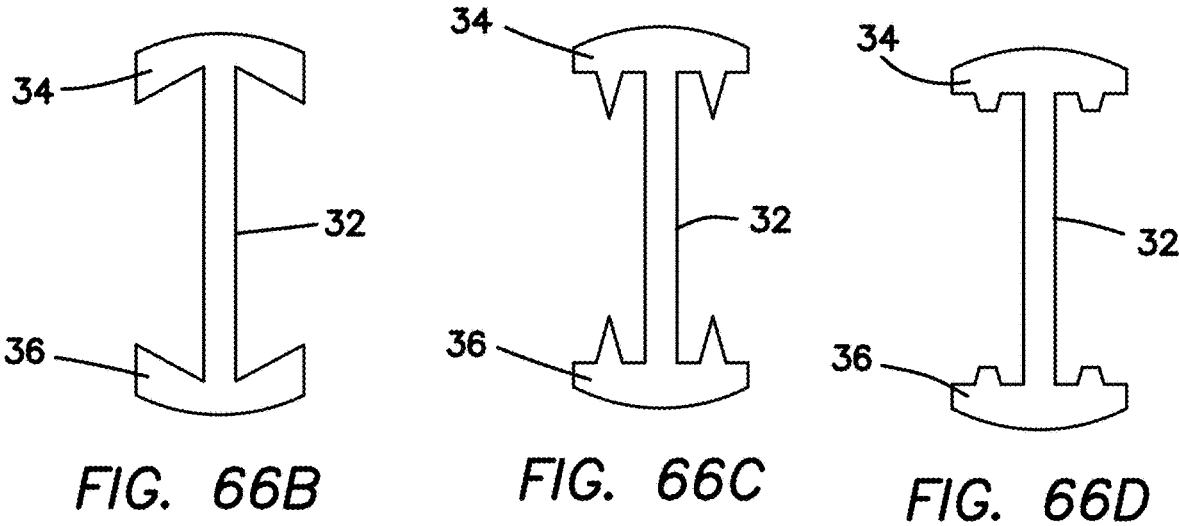
FIG. 66B is a cross-sectional end view of an I-beam according to the present invention.
FIG. 66C is a cross-sectional end view of an I-beam according to the present invention.
FIG. 66D is a cross-sectional end view of an I-beam according to the present invention.

FIG. 66A illustrates another variation of the end effector 18 that maximizes the space of the inner lower jaw 52 and length of the staple channels 53 while providing a configuration for reinforcing the end effector 18 with a thinner outer lower jaw 51. In the variation of FIG. 66A, the reinforcement for keeping the end effector 18 from bending or splaying apart is found in the configuration of the I-beam 32, in particular the configuration of the top portion 34 and bottom portion 36 of the I-beam 32. Both the top portion 34 and bottom portion 36 of the I-beam 32 have bulbous or enlarged lateral distal ends 124, 126, respectively. The top portion 34 of the I-beam 32 translates inside an upper jaw central slot 76 that is shaped to correspond with the enlarged bulbous distal ends 124. Also, the bottom portion 36 of the I-beam 32 translates inside a central lower jaw channel 55 that is shaped to correspond with the enlarged bulbous distal ends 126. These enlarged bulbous lateral distal ends 124, 126 strengthen the end effector 18 keeping it together when actuation forces are applied. Other variations of the I-beam 32 are shown in FIGS. 66B-66D. The variations of FIGS. 66B-66D illustrate top and bottom portions 34, 36 of the I-beam 32 having teeth that extend away from the outer perimeter to provide an increased thickness and lateral strength improvement. FIG. 66A illustrates a curved anvil surface 74 that is convex from the viewpoint of the gap and a curved upper surface 114 of the lower jaw 50 that is concave from the viewpoint of the gap. In the variation shown in FIG. 66A, the radius of curvature of the upper surface 114 of the lower jaw 50 is substantially the same as the radius of curvature of anvil surface 74, excluding any anvil pocket formations and curvatures. The curved upper surface 114 of the lower jaw 50 advantageously provides more space in the inner lower jaw 52 particularly near the perimeter 118 where due to the concave curvature of the upper surface 114 more space is provided to receive staples with longer legs. Also, staple legs exiting the channels 53 at the upper surface 114 are directed substantially perpendicularly against the anvil surface 74 due to the substantially matching radii of curvature of the upper surface 114 and anvil surface 74. In one variation, the radii of curvature of the upper surface 114 and anvil surface 74 also substantially equal the radius of curvature of the perimeter 118.

Figure 67:
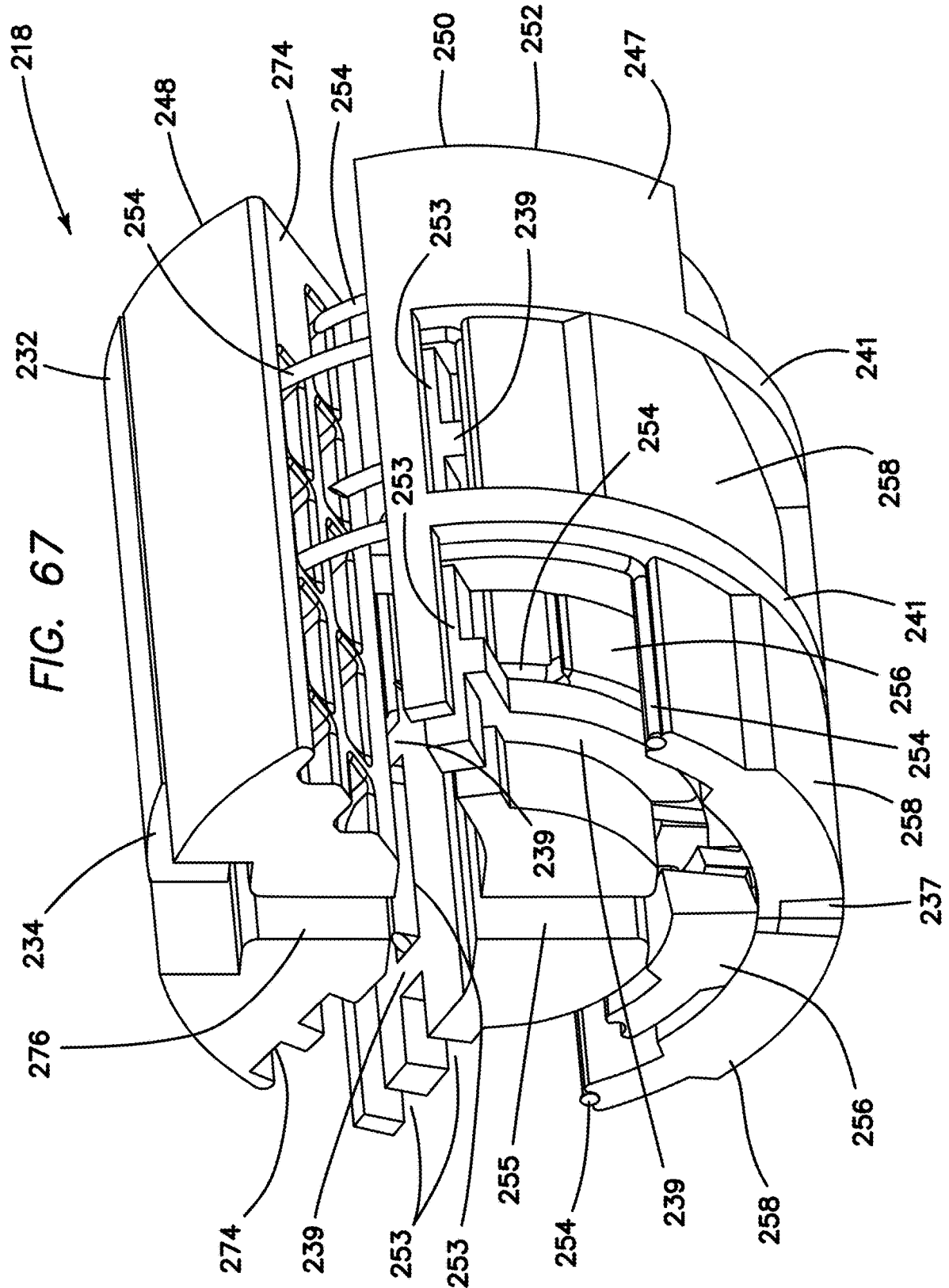
FIG. 67 is a top sectional view of an end effector according to the present invention.
Figure 68:
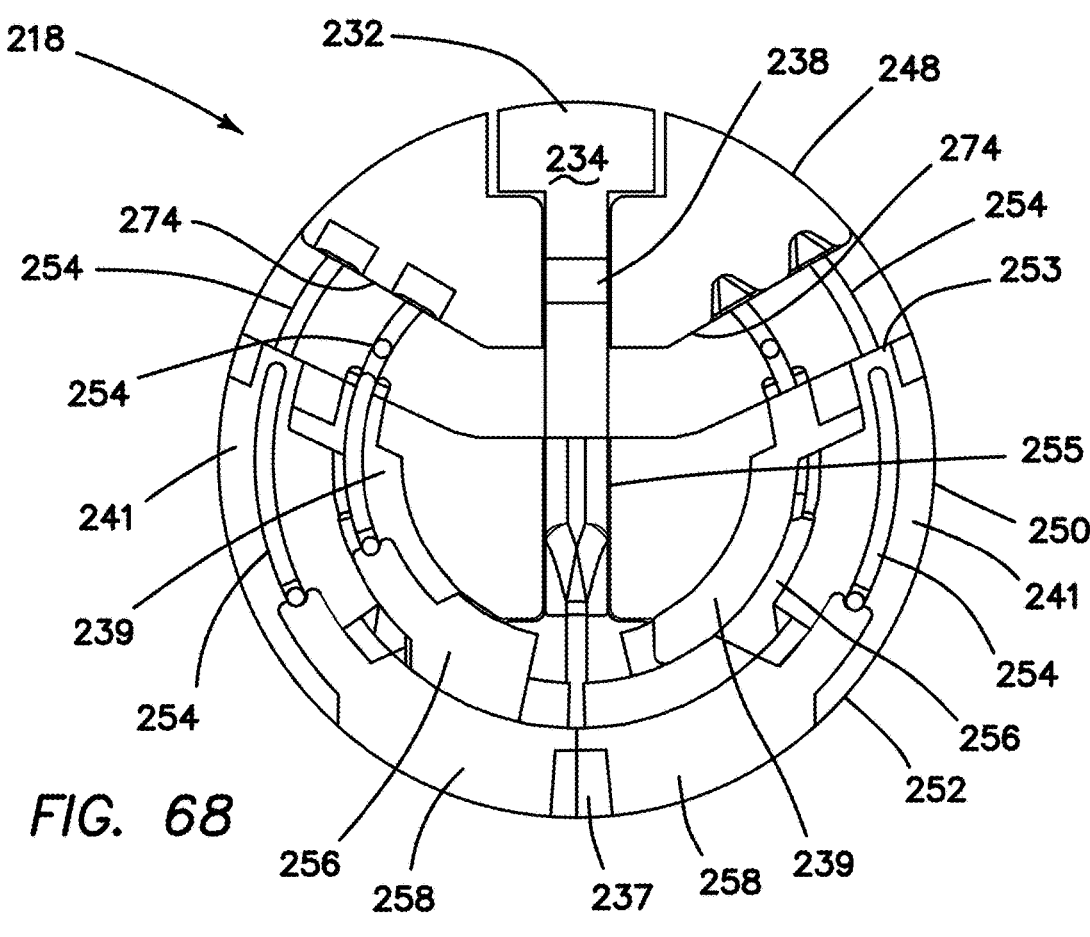
FIG. 68 is a cross-sectional end view of an end effector according to the present invention.
Figure 69:
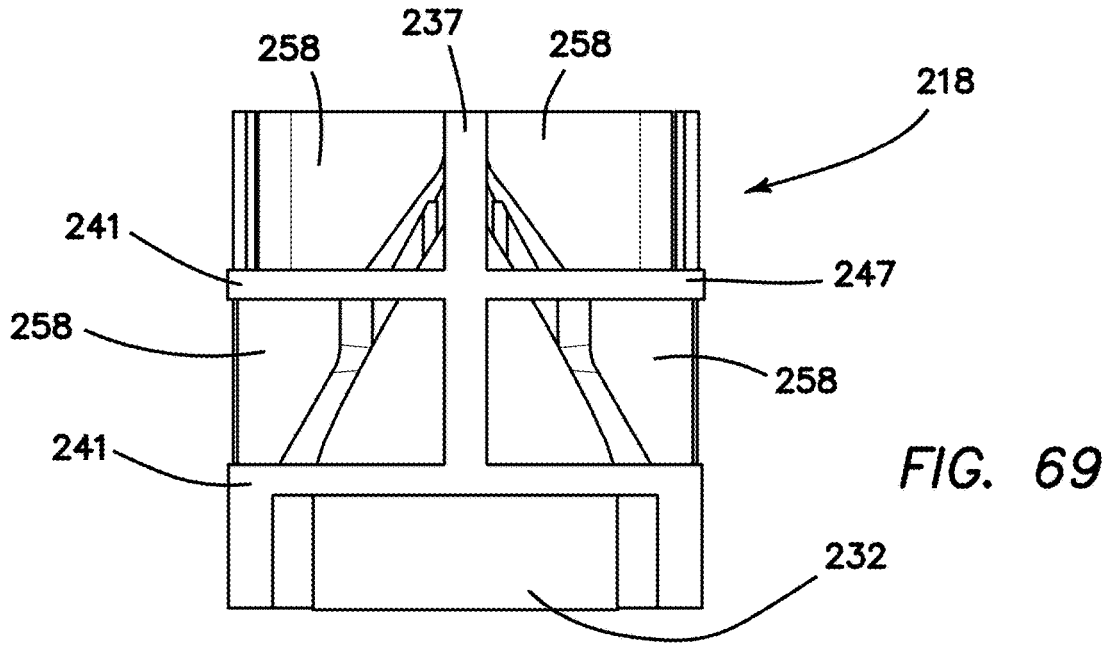
FIG. 69 is a sectional bottom view of an end effector according to the present invention.

Turning now to FIGS. 67-69, another variation of the end effector 218 will be described. The end effector 218 includes an upper jaw 248 hinged to a lower jaw 250. When the jaws 248, 250 are in a closed orientation, they form a substantially circular cross-section. The lower jaw 250 includes a staple housing or staple cartridge 252 containing a plurality of staples 254. The lower jaw 250 comprises a hollow semi-cylindrical shell or outer lower jaw (not shown) and a conformingly-shaped inner lower jaw or cartridge 252 disposed inside the outer lower jaw. The inner lower jaw 252 may or may not be removable and replaceable like a cartridge for introducing more staples 254 for continued firing. In a variation in which the inner lower jaw 252 is fixed, the entire stapler 10 is disposable after a single firing or, alternatively, the stapler cartridge assembly 14 serves as a disposable cartridge and is removed and replaced for continued firing. The inner lower jaw 252 includes a frame 247 defining a plurality of channels 253 or staple pathways configured to receive staples 254 and serve as a guide for delivering the staples 254 towards the upper jaw 248. Each channel 253 forms a top opening at the top surface of the lower jaw 250 through which a staple 254 exits the lower jaw 250. The inner lower jaw 252 includes a central channel 255 that extends longitudinally and is configured to receive a longitudinally-translating I-beam slider 232. Each channel 253 extends between the top opening and a bottom opening in the top surface of the lower jaw 250. The bottom opening is in communication with a plurality of ribs forming the frame 247. In the variation shown in FIGS. 67-69, there are two rows of staple channels 253 on either side of the central channel 255. The two rows, an inner row and an outer row, of staple channels 253 on one side of the central channel are configured such that they are staggered and not aligned with each other in order to form a sealed tissue closure. The two rows, an inner row and an outer row, of staple channels 253 on the other side of the central channel 255 are also staggered as shown. Along the longitudinal axis, the staple channels 253 comprising the inner row are longitudinally defined by a plurality of inner ribs 239 extending from the top surface. The staple channels 253 comprising the outer row are longitudinally bound and defined by a plurality of outer ribs 241 spaced apart along the length of the lower jaw 250. The outer ribs 241 are connected to a spine 237 of the frame 247 at the bottom of the lower jaw 250. Each channel 253 provides a curved pathway or arc from the top opening of the channel for guiding a curved staple 254 placed within it. In a cross-section taken perpendicular to the longitudinal axis of the end effector 218, the channels 253 define a curved pathway having a radius of curvature that substantially matches the radius of curvature of the outer lower jaw and each channel 253 forms a circumferential delivery pathway for the staple 254. In one variation, the channels 253 are concentric about the center point of a cross-section taken perpendicular to the longitudinal axis of the closed jaws 248, 250. A two-pronged staple 254 is shown residing in the channels 253. An inner pusher 256 is shown disposed inside each of the channels 253 of the inner row and an outer pusher 258 is disposed inside each of the channels 253 of the outer row.

Figures 70, 71, 72:
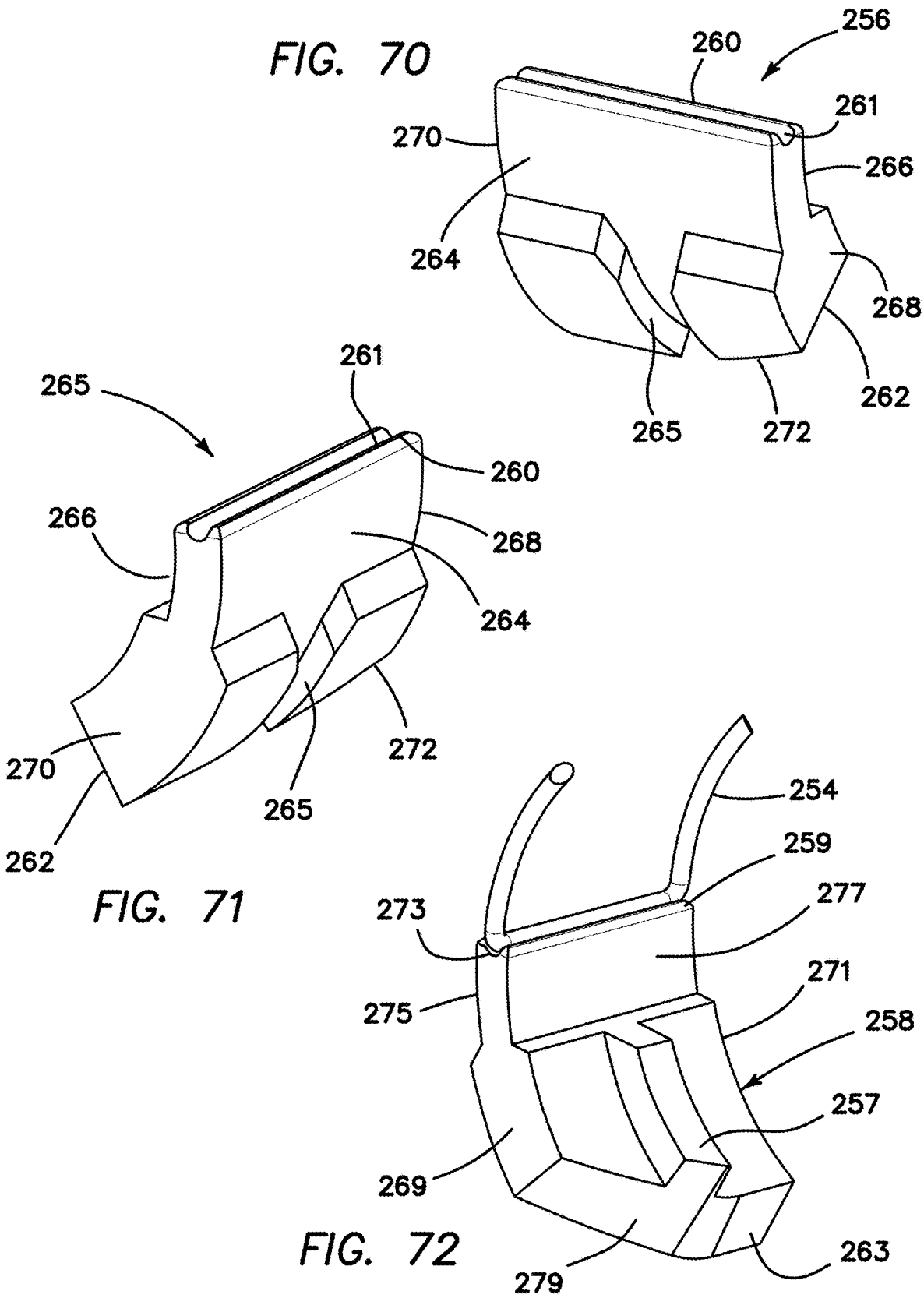
FIG. 70 is a top perspective view of an inner pusher according to the present invention.
FIG. 71 is a top perspective view of an inner pusher according to the present invention.
FIG. 72 is a top perspective view of an outer pusher and staple according to the present invention.

With reference to FIGS. 70-71, the inner pusher 256 will now be described. The inner pusher 256 is curved to conform to the curvature of the staple channels 253 in which it is disposed. The inner pusher 256 is configured to contact the leading surface of the I-beam slider 232 and in turn contact at least one staple 254. The inner pusher 256 is configured for interfacing between the I-beam slider 232 and one or more staples 254. The inner pusher 256 includes a top surface 260 and a bottom surface 262 interconnected by an outer surface 264 and an inner surface 266 and two end surfaces 268, 270. The top surface 260 is configured to contact one or more staples 254 and as such comprises a staple contacting surface. The top surface 260 of the inner pusher 256 includes a channel 261 having a curved surface adapted to cradle and stabilize the base of a staple 254. The outer surface 264 of the inner pusher 256 includes a channel 265 that is configured to receive part of an outer rib 241 which guides the upward movement of the inner pusher 256 along its curved trajectory when moved by the slider 232 preventing it from being displaced longitudinally. Between the inner surface 266 and the outer surface 264, the inner pusher 256 is narrower toward the top surface 260 and wider toward the bottom surface 262. The inner pusher 256 extends longitudinally between two end surfaces 268, 270. The bottom surface 262 includes an I-beam slider contacting surface 272 configured to contact the leading surface 244 of the I-beam slider 232. The I-beam slider contacting surface 272 is shaped to conform to the leading surface 244. If the leading surface 244 of the I-beam slider 232 is helical in shape, then the contacting surface 272 is also helical. The slider contacting surface 272 is shown to be angular or bi-angular in the FIGS. 73-76. The inner surface 266 is slightly concave and the outer surface 266 is slightly convex. Both outer and inner surfaces 264, 266 are substantially concentric with respect to each other. In one variation, the outer and inner surfaces 264, 266 are concentric with respect to the center point of a cross-section taken perpendicular the longitudinal axis of the jaws 248, 250 with the jaws 248, 250 in a closed configuration. In one variation, the outer and inner surfaces 264, 266 have a curvature that substantially matches the curvature of the channel 253 in which it resides. In one variation, the channel 253 is circumferential to a cross-section perpendicular to the longitudinal axis of the jaws 248, 250 with the jaws 248, 250 in a closed configuration and the side surfaces 64, 66 of the pusher substantially match the circumferential curvature. The end surfaces 268 and 270 are substantially parallel and perpendicular. When urged by the I-beam slider 232, each inner pusher 256 contacts a staple 254 and travels smoothly within its respective channel 253.

Figures 73, 74:
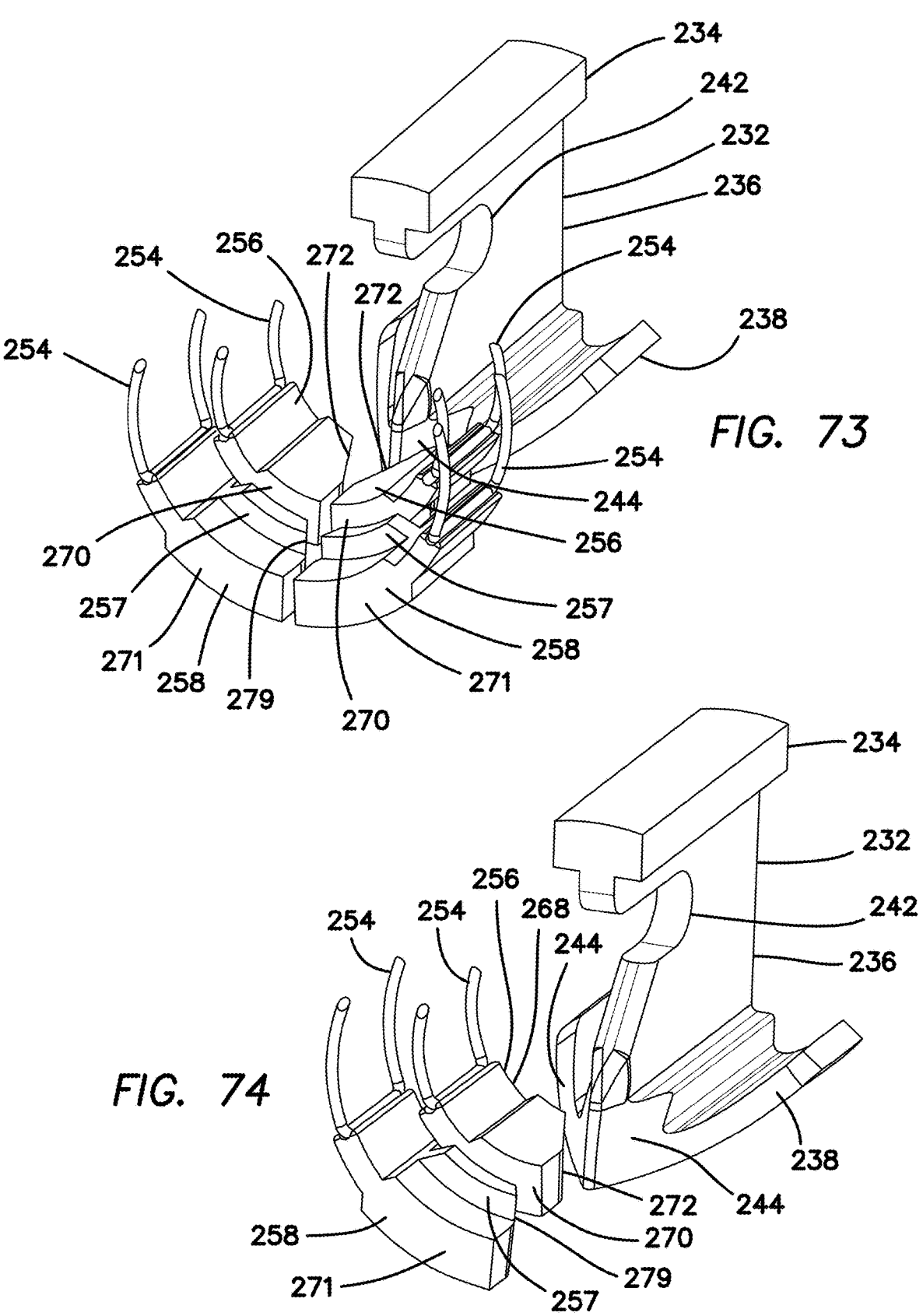
FIG. 73 is a partial sectional, top perspective view of an end effector showing an I-beam slider, two inner pushers, two outer pushers and four staples according to the present invention.
FIG. 74 is a partial sectional, top perspective view of an end effector showing an I-beam slider, an inner pusher, an outer pusher and two staples according to the present invention.
Figures 75, 76:
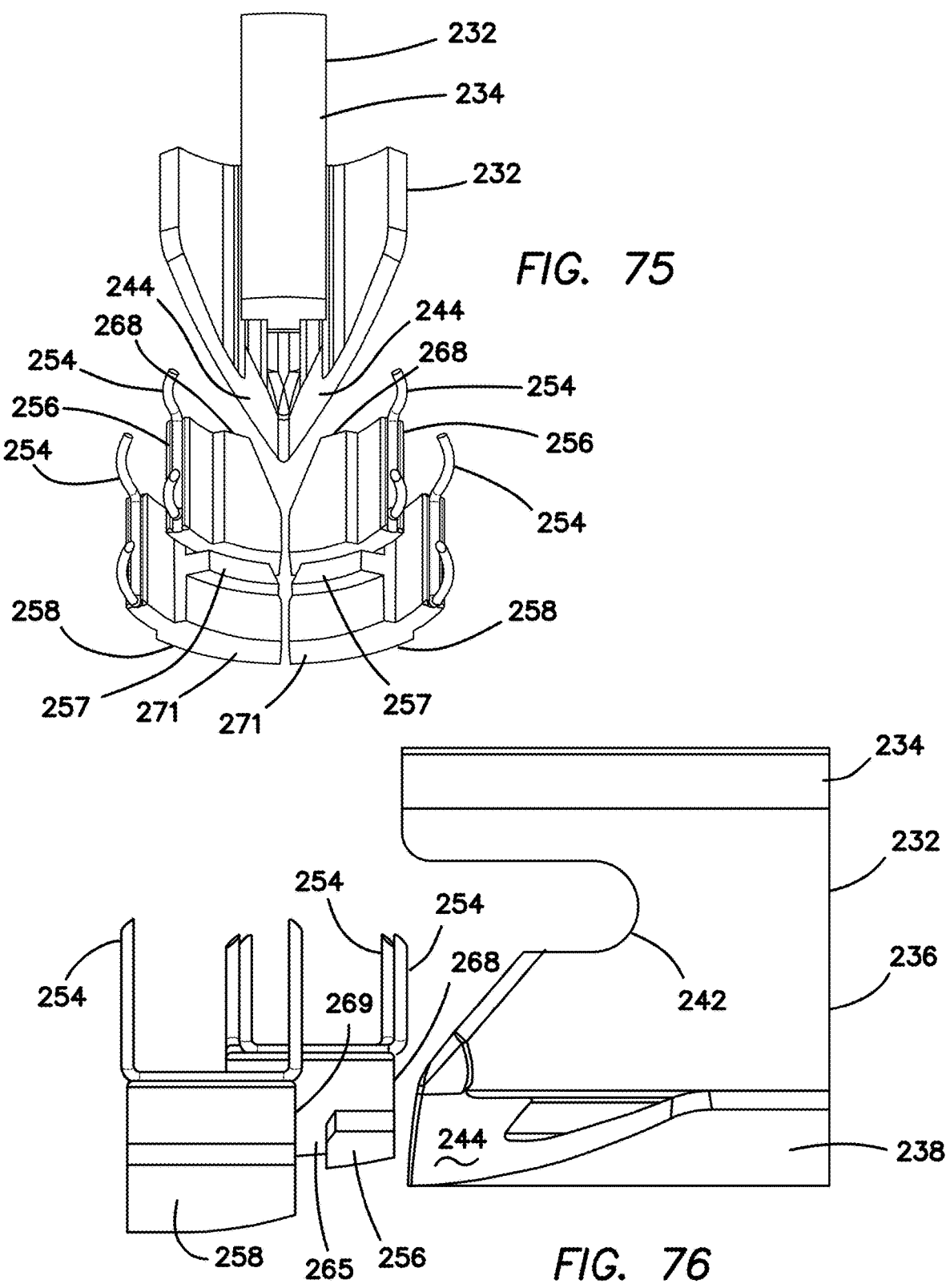
FIG. 75 is a partial sectional, top perspective view of an end effector showing an I-beam slider, two inner pushers, two outer pushers and four staples according to the present invention.
FIG. 76 is a partial sectional, side elevational view of an end effector showing an I-beam slider two inner pushers, an outer pusher and three staples according to the present invention.
Figure 77:
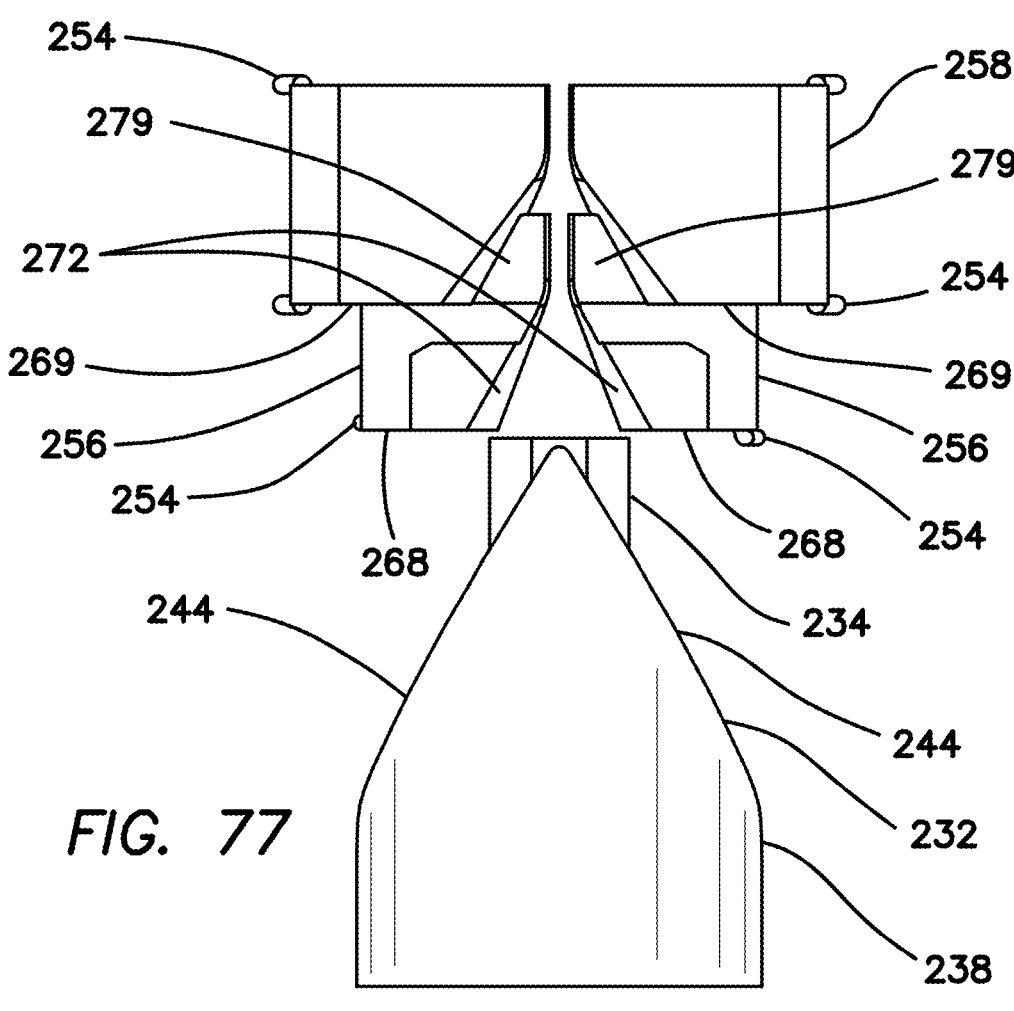
FIG. 77 is a partial sectional, bottom view of an end effector showing an I-beam slider two inner pushers, two outer pushers and four staples according to the present invention.

With reference to FIG. 72, the outer pusher 258 will be described. The outer pusher 258 is curved to conform to the curvature of the staple channels 253 in which it is disposed. The outer pusher 258 is configured to contact the leading surface of the I-beam slider 232 and in turn contact at least one staple 254. The outer pusher 258 is configured for interfacing between the I-beam slider 232 and one or more staples 254. The outer pusher 258 includes a top surface 259 and a bottom surface 263 interconnected by an outer surface 275 and an inner surface 277 and two end surfaces 269, 271. The top surface 259 is configured to contact one or more staples 254 and as such comprises a staple contacting surface. The top surface 259 of the outer pusher 258 includes a channel 273 having a curved surface adapted to cradle and stabilize the base of a staple 254. The inner surface 277 of the outer pusher 258 includes a projection 257 that is configured to abut between the end surfaces 268, 270 of adjacent inner pushers 256 as shown in FIGS. 73, 74 and 75 preventing the inner pusher 256 from being displaced longitudinally and, therefore, helping to guide the trajectory of the inner pusher 256. Between the inner surface 277 and the outer surface 275, the outer pusher 258 is narrower toward the top surface 259 and wider toward the bottom surface 263. The outer pusher 256 extends longitudinally between the two end surfaces 269, 271. The bottom surface 263 includes an I-beam slider contacting surface 279 configured to contact the leading surface 244 of the I-beam slider 232. The I-beam slider contacting surface 279 is shaped to conform to the leading surface 244. If the leading surface 244 of the I-beam slider 232 is helical in shape, then the contacting surface 279 is also helical. The slider contacting surface 279 is shown to be angular or bi-angular in the FIGS. 72-76. The inner surface 277 is slightly concave and the outer surface 275 is slightly convex. Both outer and inner surfaces 275, 277 are concentric with respect to each other. In one variation, the outer and inner surfaces 275, 277 are concentric with respect to the center point of a cross-section taken perpendicular the longitudinal axis of the jaws 248, 250 with the jaws 248, 250 in a closed configuration. In one variation, the outer and inner surfaces 275, 277 have a curvature that substantially matches the curvature of the channel 253 in which it resides. In one variation, the channel 253 is circumferential to a cross-section perpendicular to the longitudinal axis of the jaws 248, 250 with the jaws 248, 250 in a closed configuration and the outer and inner surfaces 275, 277 of the outer pusher 258 substantially match the circumferential curvature. The end surfaces 269 and 271 are substantially parallel and perpendicular. When urged by the I-beam slider 232, each outer pusher 258 contacts a staple 254 and travels smoothly within its respective channel 253.

With particular reference to FIGS. 73-75, it can be seen that the leading surface 244 of the I-beam slider 232 initially contacts the contacting surface 272 of the inner pusher 256. The opposite end surface 270 will abut the projection 257 of the outer pusher 258. In particular, at least a portion of the thickness, approximately half of the wider lower end of the inner pusher 256, of the end surface 270 will contact the projection 257 of the outer pusher 258. Also, at least a portion of the thickness, approximately half of the wider lower end of the inner pusher 256, of the end surface 270 will contact a distally located inner rib 239. As such, the application of force by the I-beam slider 232 upon the angled contacting surface 272 will direct the inner pusher 256 upwardly toward the top surface and force the staple 254 through the openings 253. The inner pusher 256 will also travel on the rail-like outer rib 241 with the outer rib 241 being located within the channel 265. Abutment of the inner pusher 256 against the inner rib 239, outer rib 241 and against the projection 257 stabilizes the position of the inner pusher 256 when in contact with the I-beam slider 232 and, when the inner pusher 256 is moved, provide a clearance for I-beam slider 232 to travel distally and into contact with an outer pusher 258. After the inner pushers 256 on either side of the central channel 255 are moved out of the way, the leading surface 244 of the I-beam slider 232 will in turn contact the contacting surface 279 of adjacent outer pushers 258 on either side of the central channel 255. Upon contact with the outer pusher 258, at least a portion of the distal end surface 271 will abut the outer rib 241 and the outer pusher 258 will be directed upwardly within the channel 253 moving the staple 254 at the top surface 259 out of the channel 253. Hence, the leading surface 244 of the I-beam slider 232 will travel along the longitudinal length of the lower jaw 250 pushing a pair of inner pushers 256 followed by a pair of outer pushers 258 sequentially and consecutively repeatedly to deploy the staples 254 across the gap between upper jaw 248 and lower jaw 250. While only a segment of the end effector 215 illustrating two inner pushers 256 and two outer pushers 258 is shown in the figures, the segment is repeated along the length of the lower jaw 250.

With continued reference to FIGS. 73-77, the I-beam slider 232 will now be described in greater detail. The I-beam slider 232 of FIGS. 73-76 is substantially similar to the I-beam slider 32 of FIGS. 7-12. The I-beam slider 232 includes a top portion 234 and bottom portion 236 interconnected by a middle portion 238. The top portion 234 includes a curved top. The middle portion 238 includes a blade 242, which would include a sharp leading edge that is shown as a blunt surface in FIGS. 73-76. At the back end, the middle portion 238 includes a portion for connecting with the extended I-beam portion 30 as shown in FIG. 6. The bottom portion 236 leads the front end of the I-beam slider 232 and includes a curved bottom with a convex outer surface and a leading surface 244 that resembles a snowplow. The leading surface 244 includes two converging surfaces that meet at a vertical line or tip. Each converging surface extends outwardly from the tip in a helical spiral fashion, that is, it not only extends upwardly, but also, spirals or curves or rotates with respect to the longitudinal axis of the I-beam slider 232 to create the helix wedge design. The front-elevational view of the I-beam is substantially in the shape of a capital letter "I" having a lower curved portion. The I-beam 232 slides longitudinally inside the end effector 218 and as such may be called a slider. The I-beam/slider 232 is configured to urge staples out of the end effector 218 via the leading surface 244.

Figure 78:
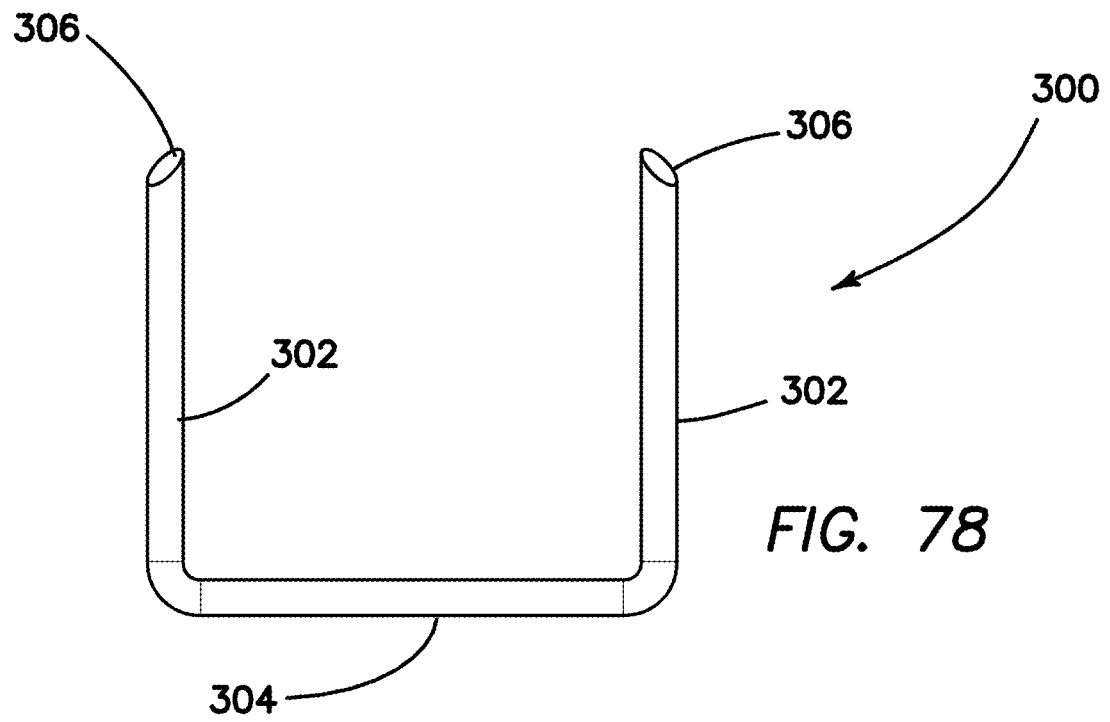
FIG. 78 is a front elevational view of a staple according to the present invention.
Figures 85, 86, 87:
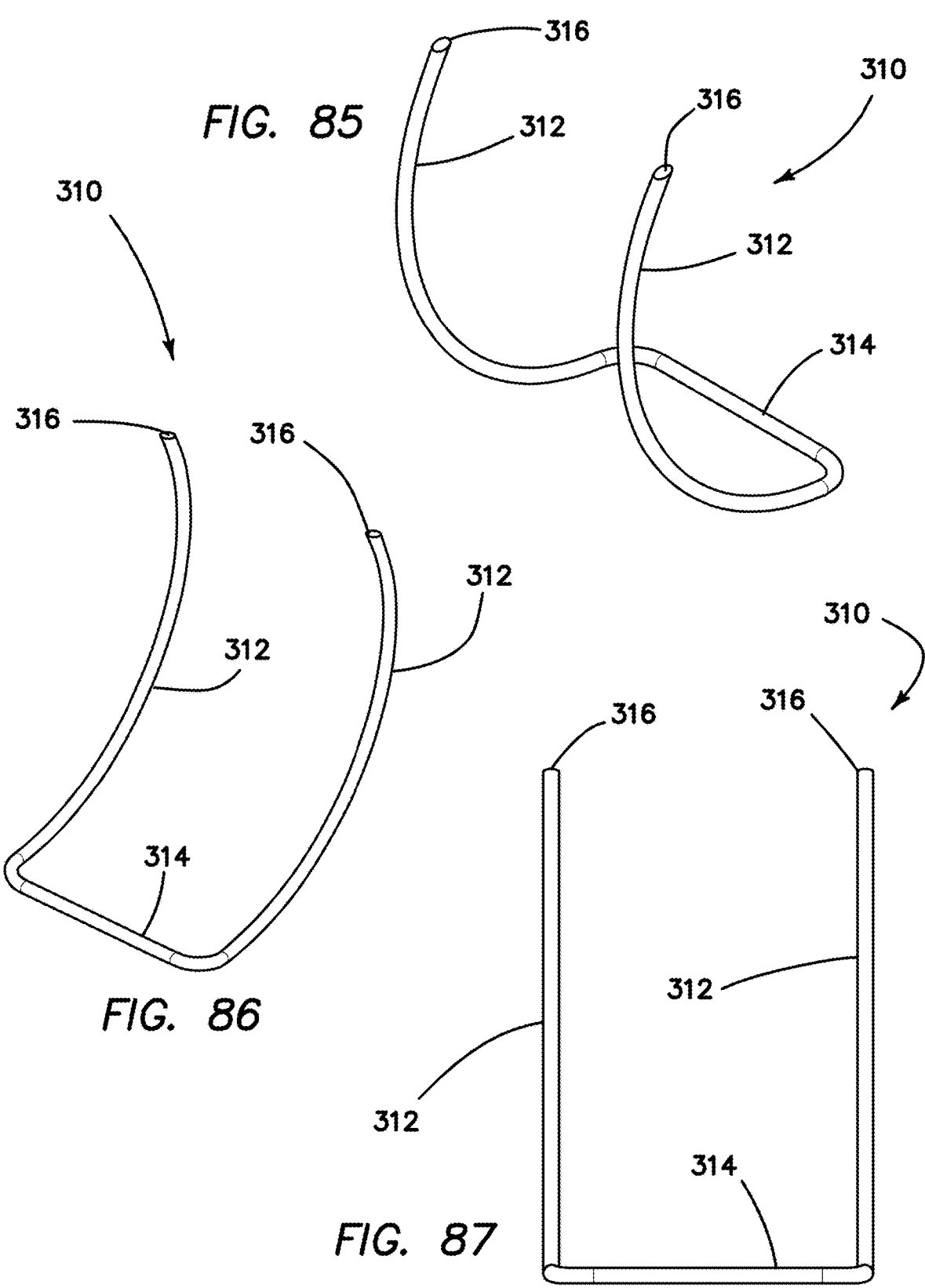
FIG. 85 is a top perspective view of a staple according to the present invention.
FIG. 86 is a top perspective view of a staple according to the present invention.
FIG. 87 is a front elevational view of a staple according to the present invention.
Figures 88, 89, 90:
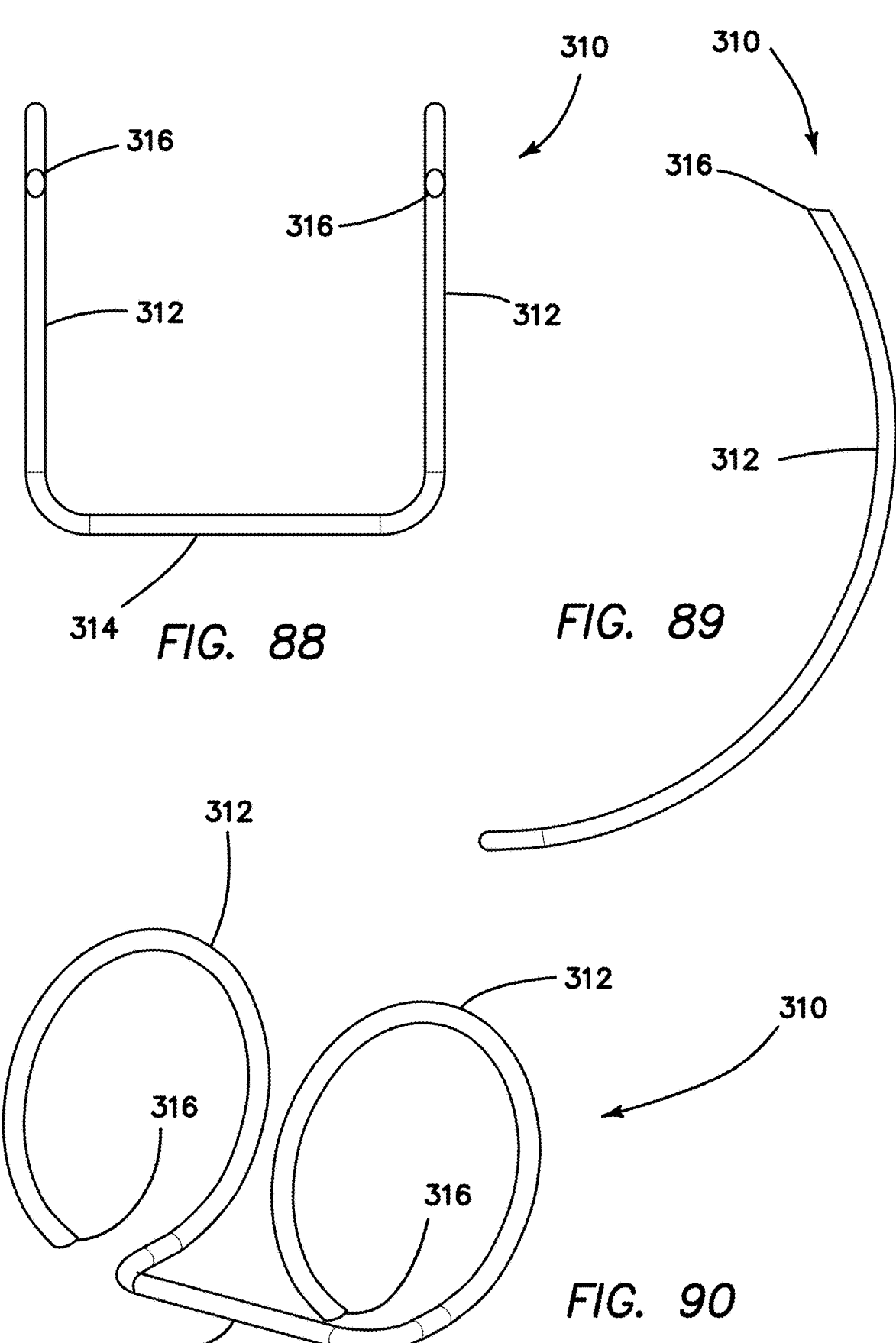
FIG. 88 is a top view of a staple according to the present invention.
FIG. 89 is a side view of a staple according to the present invention.
FIG. 90 is a top perspective view of a deformed staple according to the present invention.
Figures 91, 92, 93:
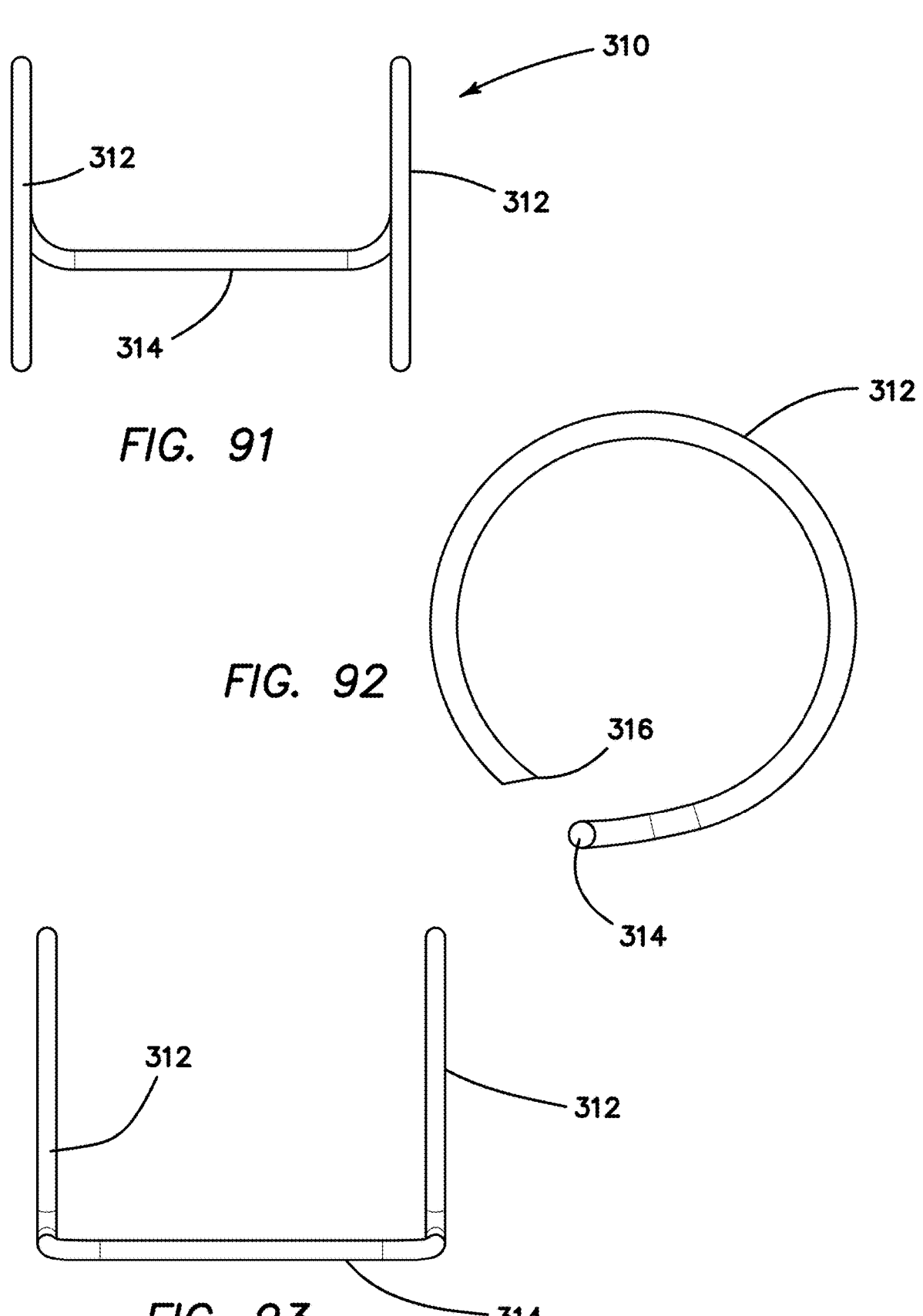
FIG. 91 is a top view of a deformed staple according to the present invention.
FIG. 92 is a side elevational view of a deformed staple according to the present invention.
FIG. 93 is a front elevation view of a deformed staple according to the present invention.

Turning now to FIGS. 78-79, a two-pronged staple 300 according to the present invention that is suitable for use with an end effector 218 described in FIGS. 67-77 as well as other embodiments found in this specification. In FIGS. 78-79, the two-pronged staple 300 is shown in its unde-formed or open configuration. The staple 300 includes two legs 302 interconnected by a base 304. The base 304 serves as a contact surface for engagement with the inner or outer pushers 256, 258. The legs 302 extend upwardly from the base 304 and curve to one side as can be clearly seen in FIG. 79. The curvature of the staple legs 302 correspond to the curvature of the circumferential channels 253 into which they are disposed and along which they travel as they are urged by the pushers 256, 258 coming sequentially into contact with the I-beam slider 232. The curvature of the staple legs 302, therefore, also substantially corresponds to the circumference of the lower jaw 250. The end of each leg 302 is angled and forms a sharp tip 306. The tip 306 may be formed in any manner and may have any geometric shape that is suitable for puncturing and penetrating tissue through which the staple 300 is delivered.

Turning now to FIGS. 80-84, there is shown the staple 300 of FIGS. 78-79 in a second or deformed configuration after complete actuation of the stapler. Deployment of the two-pronged staple 300, results in the legs 302 contacting the anvil surface of the upper jaw 248 and being deformed. The legs 302 are deflected toward each other such that the tips 306 are angled vertically downwardly toward the base 304. The legs 302 contact the anvil surface wherein anvil pockets that are aligned with the exit openings in the top surface of the lower jaw 250 may be formed to guide the proper deformation of the staple legs 302. The deformed staple 300 has a substantially B-shaped configuration and maintains a potato chip-like curvature as shown in FIG. 84. The legs 302 are deflected substantially in a longitudinal direction along the length of the end effector 218.

Turning now to FIGS. 85-89, a two-pronged staple 310 according to the present invention that is suitable for use with an end effector 218 described in FIGS. 67-77 as well as other embodiments found in this specification. In FIGS. 85-89, the two-pronged staple 310 is shown in its unde-formed or open configuration. The staple 310 includes two legs 312 interconnected by a base 314. The base 314 serves as a contact surface for engagement with the inner or outer pushers 256, 258. The legs 312 extend upwardly from the base 314 and curve to one side as can be clearly seen in FIG. 89 defining a concave side and a convex side. The curvature of the staple legs 312 correspond to the curvature of the circumferential channels 253 into which they are disposed and along which they travel as they are urged by the pushers 256, 258 coming sequentially into contact with the I-beam slider 232. The curvature of the staple legs 312, therefore, also substantially corresponds to the circumference of the lower jaw 250. The end of each leg 312 forms a sharp tip 316. The tip 316 may be formed in any manner and may have any geometric shape that is suitable for puncturing and penetrating tissue through which the staple 310 is delivered.

Turning now to FIGS. 90-93, there is shown the staple 310 of FIGS. 85-89 in a second or deformed configuration after complete actuation of the stapler. Deployment of the two-pronged staple 310, results in the legs 312 contacting the anvil surface of the upper jaw 248 and being deformed. The legs 312 are deflected toward one direction to close the pre-deformed curvature into a nearly closed circular con-figuration. The tips 306 are generally angled vertically downwardly toward the base 314. The legs 312 contact the anvil surface wherein anvil pockets that are aligned with the exit openings in the top surface of the lower jaw 250 may be formed to guide the proper deformation of the staple legs 312. Each of the legs 312 of the deformed staple 310 has a substantially circular configuration with each circular con-figuration lying in a plane that is perpendicular to the base 314. The legs 312 of staple embodiment 310 are deflected laterally to the longitudinal axis of the end effector 218.

Referring back to FIGS. 67-68, the upper jaw 248 of the end effector 218 will now be described. The upper jaw 248 is substantially semi-cylindrical in shape to conform to a cylindrical lumen of a cannula in which it is inserted. The upper jaw 248 includes a central slot 276 that extends longitudinally. The central slot 276 is conformingly shaped and configured to receive the top portion 234 of the I-beam slider 232 and at least a portion of the narrower middle portion 238 of the I-beam slider 232 such that the I-beam slider 232 is capable of longitudinal movement relative to the upper jaw 248 inside and along the central slot 276. The central slot 276 includes an open proximal end which is ramped and configured to cam against the beveled front end of the I-beam slider 232. The upper jaw 248 is spring biased in an open orientation with respect to the lower jaw 250 and as the beveled front end of the I-beam slider 232 enters the central slot 276, and in particular, the top portion 234 enters the wider upper end of the central slot 276, the upper and lower jaws 248, 250 are forced to close. Back and forth movement of the I-beam slider 232, into and out of the central slot 276 or against the proximal opening of the central slot 276, opens and closes the end effector 218 allowing the user to grasp and release tissue and reposition the stapler 10. With the end effector 218 in the closed configuration, the I-beam slider 232 is capable of further longitudinal translation within the central slot 276. Following the ejection of staples 254, the I-beam slider 232 is retracted proximally via the handle assembly 12 and as the I-beam slider 232 exits the central slot 276 the spring biased upper jaw 248 moves into an open orientation. Following the ejection of staples 254 and retraction of the I-beam slider 232, repeated forward translation of the I-beam slider 232 inside the central slot 276 is prevented by a lock-out mechanism to avoid inadvertent use of an already-fired cartridge.

Also with reference to FIGS. 67-68, the upper jaw 248 further includes an inner anvil surface 274 or plate that faces and is spaced apart from the lower jaw 250 when in the closed position. The anvil surface 274 is configured to receive the legs of a staple 254 and guide, deflect, angulate, bend, crimp or clinch the staple legs as the staple 254 is urged through tissue against the anvil surface 274. To facilitate the formation of staples 254 to secure tissue, a plurality of staple-forming pockets is shown in FIGS. 67-68 are included in the anvil surface 274. These surface formations of a typical anvil aid in the deformation of the staple as it is deployed to achieve proper staple closure. The staple-forming pockets are aligned with the exit openings of channels 253 in the lower jaw 250. The staple-forming pockets generally include two adjacent staple leg forming cups having a curved or sloped channeling surface formed around the perimeter of each of the staple forming cups. The two adjacent staple leg forming cups form a dog bone shape that facilitates the formation of consistent B-shaped staples from generally square-cornered U-shaped undeformed staples. To laterally urge the legs of a staple relative to the base of the staple as in the variation of the staple shown in FIGS. 85-93, an anvil surface or staple pocket is configured accordingly. Separate staple-forming pockets are provided at each staple forming location opposite the cartridge channels 253 of the lower jaw 250.

Figures 94, 95, 96:
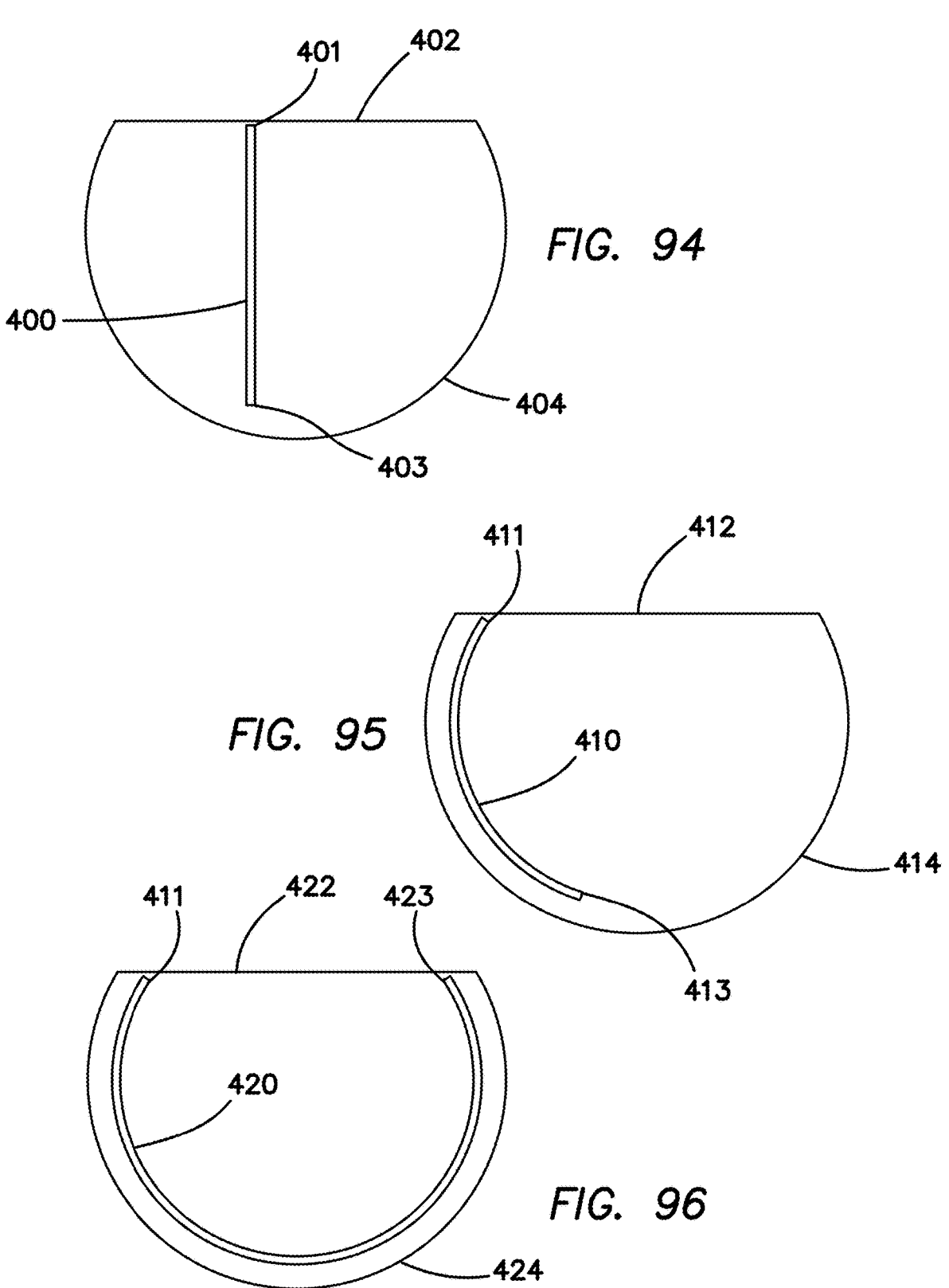
FIG. 94 is a schematic of a cross-sectional view of a lower jaw and staple.
FIG. 95 is a schematic of a cross-sectional view of a lower jaw and staple according to the present invention.
FIG. 96 is a schematic of a cross-sectional view of a lower jaw and staple according to the present invention.

As described earlier, the leg length of a staple employed in a conventional surgical stapler is generally limited by a distance perpendicular to the upper surface 402 of the lower jaw 404 which is depicted by a line segment 400 that is representative of the length of a staple leg in FIG. 94. One end 401 of the line segment 400 is proximal to the upper surface 402 of the lower jaw 404 and the other end 403 of the line segment 400 is proximal to the lower periphery of the lower jaw 404. The lower jaw 404 is depicted by a partial circle having an approximate diameter of 0.5 inches. The distance from the upper surface 402 of the lower jaw 404 to the distal most point on the circle 404 at the diameter of the lower jaw 404 is approximately 0.38. Therefore, as depicted in FIG. 94, the length of the line segment or otherwise, the length of a staple leg 400 is approximately 0.34 inches for a staple having a leg wire diameter of approximately 0.01 inches in a conventional linear stapler design. In contrast to a linear stapler of FIG. 94, a schematic of a circumferential stapler lower jaw 414 of the present invention is depicted in FIG. 95 wherein the length of a staple leg is defined by a curve 400 instead of a straight line inside the lower jaw 414. One end 411 of the staple leg 410 is near the upper surface 412 of the lower jaw 414 and the other end 413 is near the lower periphery of the lower jaw 414. The end 413 is in the same location as the end 403 of FIG. 94. The staple leg 410 of FIG. 95 is curved depicting a staple 410 residing inside a curved channel of a circumferential stapler according to the present invention. Given the same dimensions for the lower jaw diameter (approximately 0.5 inches) and the same distance from the upper surface 412 to the diametrical outermost point on the circle 414 of approximately 0.38 inches, the staple leg 410 is approximately 0.41 in length compared to a staple leg 400 having a length of only approximately 0.34. Therefore, the staple leg length is approximately 20% longer in the present invention. Hence, the advantages of the present invention are demonstrably longer staple lengths which provide the ability to staple through and hold thicker tissue segments in a stapler of the same diameter.

Turning now to FIG. 96, there is shown yet another schematic of a circumferential stapler design according to the present invention. FIG. 96 depicts a staple leg length 420 as a curve inside a schematic of a stapler lower jaw 424. The staple leg 420 has one end 421 near the upper surface 422 of the lower jaw 424 and a second end 423 also near the upper surface 422 of the lower jaw 424 for a total staple leg length of approximately 0.97 inches which is significantly longer than the staple length of FIGS. 94 and 95. The lower jaw 424 is depicted as a partial circle having a diameter of approximately 0.5 inches and having a distance from the upper surface 422 to a diametrical outermost point on the circle of approximately 0.38 inches which are the same dimensions for the lower jaw 424 as depicted in FIGS. 94 and 95. In this variation, the circumferential design takes advantage of firing along nearly the entire circumference of the lower jaw 424 in contrast to a perpendicular distance on either side of the midline as shown in FIG. 94 or along a part of the circumference as shown in FIG. 95. The staple length of FIG. 96 is approximately 285% longer than the conventional stapler depicted in FIG. 94 which illustrates the tremendous advantage in terms of a longer staple leg length afforded by designs comprising circumferential firing according to the present invention.

Conventional laparoscopic staplers are currently approximately 12 millimeters in diameter which require a larger sized cannula for insertion and, hence, a larger incision in the patient. The laparoscopic stapler 10 of the present invention with rotational firing has a diameter of approximately 0.200-0.400 inches which will advantageously fit inside smaller diameter cannulas that require smaller incisions in the patient while at the same time have capabilities of stapling the same thickness tissue as the larger staplers. The circumferential stapler offers at least a 20% reduction in size of the outer diameter of the stapler while delivering staples with the same leg length as in a larger diameter stapler having a conventional design. The smaller incision results in less pain, less bleeding, faster patient recovery times and a smaller scar visible after the operation. The stapler of the present invention is particularly well-suited for laparoscopic procedures; however, the invention is not so limited and the stapler of the present invention can be used in open surgical procedures equally effectively.

It is understood that various modifications may be made to the embodiments of the surgical stapler disclosed herein. Therefore, the above description should not be construed as limiting, but merely as exemplifications of preferred embodiments. Those skilled in the art will envision other modifications within the scope and spirit of the present disclosure.

We claim:

1. A surgical stapler comprising:
a stapler cartridge assembly extending from a proximal end to a distal end;
an end effector at the distal end of the stapler cartridge assembly, the end effector defining a longitudinal axis, the end effector comprising:
a lower jaw having an upper surface, the lower jaw comprising a plurality of staple channels arranged longitudinally along the longitudinal axis of the end effector and configured to receive staples, each staple channel having a channel opening at the upper surface through which a staple exits the lower jaw;
an upper jaw having an anvil surface, the upper jaw connected to the lower jaw such that the upper jaw is movable relative to the lower jaw between an open configuration and a closed configuration;
wherein a center point and midline are defined in a cross-section taken perpendicular to the longitudinal axis of the end effector with the jaws in a closed configuration;
wherein an inner staple line and an outer staple line are defined on each side of the midline by a plurality of the channel openings aligned in an inner row and an adjacent outer row on the upper surface;
wherein the staple channels are curved about the center point in the cross-section taken perpendicular to the longitudinal axis to provide a curved pathway for guiding curved staples located therein;
a plurality of inner pushers disposed in the lower jaw that are configured to contact and eject staples from the inner row, the inner pushers having an inner curvature configured for movement within the staple channels of the inner staple line; and
a plurality of outer pushers disposed in the lower jaw that are configured to contact and eject staples from the outer row, the outer pushers having an outer curvature configured for movement within the staple channels of the outer staple line.

2. The surgical stapler of claim 1, wherein the end effector further comprises a central channel formed in the upper jaw and the lower jaw along the midline and along the length of the end effector; the central channel being configured to receive a slider longitudinally movable inside the central channel and configured to sequentially contact the plurality of inner pushers and the plurality of outer pushers.

3. The surgical stapler of claim 2, wherein the slider comprises an I-beam profile having a top portion slidable within the central channel in the upper jaw and a bottom portion slidable within the central channel in the lower jaw, the top portion and the bottom portion interconnected by a middle portion, and the bottom portion having a leading surface configured to sequentially contact the plurality of inner pushers and the plurality of outer pushers.

4. The surgical stapler of claim 3, wherein each inner pusher comprises a bottom surface having a slider contacting surface configured to contact the leading surface of the slider.

5. The surgical stapler of claim 4, wherein the slider contacting surface is shaped to conform to the leading surface.

6. The surgical stapler of claim 1, wherein each outer pusher has an inner surface comprising a projection extending inwardly therefrom.

7. The surgical stapler of claim 6, wherein the projection is positioned between adjacent inner pushers to maintain a longitudinal position of the adjacent inner pushers relative to the longitudinal axis of the end effector.

8. The surgical stapler of claim 1, wherein each staple of the plurality of staples comprises a first leg and a second leg interconnected by a base, and wherein the first leg and the second leg extend upwardly from the base and each have a curvature corresponding to the staple channel in which each staple is received.

9. A surgical stapler comprising:
a stapler cartridge assembly extending from a proximal end to a distal end;
an end effector at the distal end of the stapler cartridge assembly, the end effector defining a longitudinal axis, the end effector comprising:
a lower jaw having an upper surface, the lower jaw comprising:
a central channel extending longitudinally;
a first inner row of staple channels on a first side of the central channel;
a first outer row of staple channels on the first side of the central channel;
a second inner row of staple channels on a second side of the central channel opposite the first side; and
a second outer row of staple channels on the second side;
an upper jaw having an anvil surface, the upper jaw connected to the lower jaw such that the upper jaw is movable relative to the lower jaw between an open configuration and a closed configuration;
a plurality of inner pushers disposed in the first inner row and the second inner row; and
a plurality of outer pushers disposed in the first outer row and the second outer row;
wherein in a cross-section taken perpendicular to the longitudinal axis of the end effector, the staple channels of the first inner row, the first outer row, the second inner row, and the second outer row are curved to provide a curved pathway for staples.

10. The surgical stapler of claim 9, wherein the first inner row of staple channels and the second inner row of staple channels have a first curvature.

11. The surgical stapler of claim 10, wherein the inner pushers are curved to conform to the first curvature.

12. The surgical stapler of claim 9, wherein the first outer row of staple channels and the second outer row of staple channels have a second curvature.

13. The surgical stapler of claim 12, wherein the outer pushers are curved to conform to the second curvature.

14. The surgical stapler of claim 9, wherein each inner pusher includes a top surface and a bottom surface interconnected by an outer surface and an inner surface and two end surfaces, wherein the top surface of the inner pusher is configured to contact a staple, and wherein the inner surface and the outer surface of the inner pusher are curved.

15. The surgical stapler of claim 9, wherein each outer pusher includes a top surface and a bottom surface interconnected by an outer surface and an inner surface and two end surfaces, wherein the top surface of the outer pusher is configured to contact a staple, and wherein the inner surface and the outer surface of the inner pusher are curved.

16. The surgical stapler of claim 9, wherein the lower jaw has an upper surface and a lower surface, and wherein the lower jaw comprises a frame comprising:

a spine extending along the lower surface;

a plurality of inner ribs extending from the upper surface; and a plurality of outer ribs extending from the spine.

17. The surgical stapler of claim 16, wherein each inner pusher has an outer surface comprising a channel configured to receive a portion of one of the plurality of outer ribs.

18. The surgical stapler of claim 16, wherein each inner pusher has a proximal end surface and a distal end surface, and wherein a portion of the distal end surface abuts one of the plurality of inner ribs.

19. The surgical stapler of claim 18, wherein each outer pusher has an inner surface comprising a projection extending inwardly therefrom, and wherein a second portion of the distal end surface of the inner pusher abuts the projection.

20. The surgical stapler of claim 16, wherein each outer pusher has a proximal end surface and a distal end surface, and wherein a portion of the distal end surface abuts one of the plurality of outer ribs.

* * * * *